(12) United States Patent
Schriemer et al.

(10) Patent No.: US 10,960,059 B2
(45) Date of Patent: Mar. 30, 2021

(54) COMPOSITIONS AND METHODS FOR TREATING GLUTEN INTOLERANCE AND DISORDERS ARISING THEREFROM

(71) Applicant: Codexis, Inc., Redwood City, CA (US)

(72) Inventors: David C. Schriemer, Chestermere (CA); Martial Rey, Paris (FR)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 15/906,972

(22) Filed: Feb. 27, 2018

(65) Prior Publication Data

US 2019/0022194 A1    Jan. 24, 2019

Related U.S. Application Data

(63) Continuation of application No. 14/741,396, filed on Jun. 16, 2015, now abandoned.

(60) Provisional application No. 62/118,396, filed on Feb. 19, 2015, provisional application No. 62/012,865, filed on Jun. 16, 2014.

(51) Int. Cl.
*A61K 38/48* (2006.01)
*A61K 36/185* (2006.01)

(52) U.S. Cl.
CPC .......... *A61K 38/488* (2013.01); *A61K 36/185* (2013.01); *A61K 38/48* (2013.01); *C12Y 304/00* (2013.01); *C12Y 304/23012* (2013.01)

(58) Field of Classification Search
None
See application file for complete search history.

(56) References Cited

U.S. PATENT DOCUMENTS

| | | |
|---|---|---|
| 5,618,564 A | 4/1997 | Kimura et al. |
| 6,190,905 B1 | 2/2001 | Dalboege et al. |
| 7,303,871 B2 | 12/2007 | Hausch et al. |
| 7,320,788 B2 | 1/2008 | Shan et al. |
| 7,628,985 B2 | 12/2009 | Shan et al. |
| 7,910,541 B2 | 3/2011 | Hausch et al. |
| 7,943,312 B2 | 5/2011 | Hausch et al. |
| 8,119,125 B2 | 2/2012 | Gass |
| 8,143,210 B2 | 3/2012 | Shan et al. |
| 8,148,105 B2 | 4/2012 | Vora et al. |
| 9,005,610 B2 | 4/2015 | Schriemer et al. |
| 9,498,520 B2 | 11/2016 | Jolly et al. |
| 9,598,684 B2 | 3/2017 | Helmerhorst et al. |
| 9,745,565 B2 | 8/2017 | Schriemer |
| 9,993,531 B2 | 6/2018 | Siegel et al. |
| 2005/0107786 A1 | 5/2005 | Canady |
| 2005/0249719 A1 | 11/2005 | Shan et al. |
| 2006/0095096 A1 | 5/2006 | DeBenedictis et al. |
| 2008/0115411 A1 | 5/2008 | Ramsey |
| 2008/0115428 A1 | 5/2008 | Schlam et al. |
| 2010/0011456 A1 | 1/2010 | Mathur et al. |
| 2010/0021752 A1 | 1/2010 | Okamura et al. |
| 2010/0042203 A1 | 2/2010 | Cottone, Jr. et al. |
| 2010/0322912 A1 | 12/2010 | Khosla et al. |
| 2011/0097266 A1 | 4/2011 | Maecke et al. |
| 2012/0156253 A1 | 6/2012 | Shan et al. |
| 2012/0225050 A1 | 9/2012 | Knight et al. |
| 2013/0045195 A1 | 2/2013 | Kumar |
| 2014/0140980 A1 | 5/2014 | Schriemer |
| 2014/0186330 A1 | 7/2014 | Schriemer et al. |
| 2015/0265686 A1 | 9/2015 | Schriemer |
| 2015/0290301 A1 | 10/2015 | Schriemer et al. |
| 2015/0352195 A1 | 12/2015 | Berner et al. |

FOREIGN PATENT DOCUMENTS

| | | |
|---|---|---|
| CN | 1557402 A | 12/2004 |
| CN | 101732504 A | 6/2010 |
| EP | 2090662 A2 | 8/2009 |
| JP | H11049697 A | 2/1999 |
| JP | 2004248654 A | 9/2004 |
| WO | WO-199942215 | 8/1999 |
| WO | WO-2008115428 | 9/2005 |
| WO | WO-2008115411 | 9/2008 |
| WO | WO-2010021752 | 2/2010 |
| WO | WO-2010042203 | 4/2010 |
| WO | WO-2012006384 | 1/2012 |
| WO | WO-2014078935 | 5/2014 |

OTHER PUBLICATIONS

Kelleher, Adhesion molecules utilized in binding of intraepithelial lymphocytes to human enterocytes, Eur. J. Immunol. 1994, pp. 1013-1016., vol. 24.
Leon, Flow cytometry of intestinal intraepithelial lymphocytes in celiac disease, J. of Immun. Methods, Jan. 2011, pp. 177-136, vol. 363.
Sollid, et al., Triggers and drivers of autoimmunity: lessons from coeliac disease, Nat Rev. Immuncl. Apr. 2013, 18 pages, vol. 13, No. 4.
Woychik et al., "Wheat Gluten Proteins, Amino Acid Composition of Proteins in Wheat Gluten", J. Agric. Food Chem., 1961 , 9(4), 307-310.
Adlassnig W., et al., "Traps of carnivorous pitcher plants as a habitat: composition of the fluid, biodiversity and mutualistic activities," 2011. Annals of Botany. 107: 181-194.
Amagase, et al., "Acid Protease in Nepenthes," The Journal of Biochemistry, (1969), 66(4):431-439.
Athauda, et al., "Enzymic and structural characterization of nepenthesin, a unique member of a novel subfamily of aspartic proteinases," Biochemical Journal (2004) 381(1):295-306.

(Continued)

*Primary Examiner* — Paul J Holland
(74) *Attorney, Agent, or Firm* — Mintz Levin Cohn Ferris Glovsky and Popeo, P.C.

(57) ABSTRACT

The invention described herein relates to methods and compositions for treatment of gluten intolerance and related conditions (e.g., celiac disease and gluten sensitivity), or inhibition of inflammation and/or immune response in the intestine due to antigenic food peptides, by administration of a pharmaceutical composition comprising one or more *Nepenthes* enzymes.

15 Claims, 18 Drawing Sheets

Specification includes a Sequence Listing.

(56) References Cited

OTHER PUBLICATIONS

Bennett, et al., "Discovery and Characterization of the Laulimalide-Microtubule Binding Mode by Mass Shift Perturbation Mapping," Chemistry & Biology, (2010), 17:725-734.
Bethune, et al., "Oral enzyme therapy for celiac sprue," Methods Enzymol., (2012), 502:241-271.
Blonder, et al., "Proteomic investigation of natural killer cell microsomes using gas-phase fractionation by mass spectrometry," Biochimica et Biophysica Acta, (2004), 1698:87-95.
Chen, Jiongjiong, et al., "Aspartic proteases gene family in rice: gene structure and expression, predicted protein features and phylogenetic relation." Gene 442.1 (2009): 108-118.
Chung, et al., "Aspartic Proteinases are Expressed in Pitchers of the Carnivorous Plant *Nepenthes Alata Blanco*," Planta, Springer Verlag, DE, vol. 214, No. 5, (Mar. 1, 2002), p. 661-667.
Clabots, et al., "Acquisition of Clostridium difficile by Hospitalized Patients: Evidence for Colonized New Admissions as a Source of Infection," J. Infectious Diseases, (1992), 166:561-567.
Dunker, et al., "Intrinsically disordered protein," J. Molecular Graphics and Modelling, (2001), 19:26-59.
Freeman, "Pearls and pitfalls in the diagnosis of adult celiac disease," Canadian Journal of Gastroenterology, vol. 2, No. 3, pp. 273-280. (Mar. 2008).
GenBank AB114914.1. GenBank 2004. p. 1-2 (2004).
GenBank AB114915.1. GenBank 2004. p. 1-2 (2004).
GenBank AFV26025.1. GenBank 2012. p. 1-2 (2012).
Gleba, Y., et al., "Viral Vectors for the Expression of Proteins in Plants," Current Opinion in Biotechnology, 18:134-141. (2007).
Good NE., et al., "Hydrogen Ion Buffers for Biological Research," 1966. Biochemistry. vol. 5, No. 2. p. 467-477.
Gottlieb, et al., "Development of drugs for celiac disease: review of endpoints for Phase 2 and 3 trials," Gastroenterology Report, vol. 3, No. 2, pp. 91-102 (Feb. 26, 2015).
Hammel, et al., "XLF Regulates Filament Architecture of the XRCC4.Ligase IV Complex," Structure, (2010), 18:1431-1442.
Hamuro, et al., "Specificity of immobilized porcine pepsin in H/D exchange compatible conditions," Rapid Commun. Mass Spectrom., (2008), 22:1041-1046.
Hatano, et al., "Proteome analysis of pitcher fluid of the carnivorous plant *Nepenthes alata*," Journal of Proteome Research (2008), 7(2):809-816.
Hatano, et al., "Proteomic analysis of secreted protein induced by a component of prey in pitcher fluid of the carnivorous plan Nepenthes alata," JPROT, (2012), 1-9.
Jentsch, J., "Enzymes from carnivorius plants (*Nepenthes*). Isolation of the protease nepenthacin," FEBS Letters, (1972), 21(3):273-276.

Junop, et al., "Crystal structure of the Xrcc4 DNA repair protein and implications for end joining," The EMBO Journal, (2000), 19(22):5962-5970.
Kadek, et al., "Expression and characterization of plant aspartic protease nepenthesin-1 from Nepenthes gracilis," Protein Expression and Purification, vol. 95, (Dec. 21, 2013), p. 121-128.
Kubota, et al., "Stability Profiles of Nepenthesin in Urea and Guanidine Hydrochloride: Comparison with Porcine Pepsin A," Biosci. Biotechnol. Biochem., (2010), 74(11):2323-2326.
Lahdeaho, et al., "Recent advances in the development of new treatment for celiac disease," Expert Opin. Biol. Ther. (Early Online) 1-12, 2012.
Mazorra-Manzano, et al., "Structure-function characterization of the recombinant aspartic proteinase A1 from *Arabidopsis thaliana*," Photchem., (2010), 71(5-6):515-523.
Mitea, et al., "Efficient degradation of gluten by a prolyl endoprotease in a gastrointestinal model: implications for coeliac disease," Gut, (2008), 57:25-32.
Rey, et al., "Nepenthesin from Monkey Cups for Hydrogen/Deuterium Exchange Mass Spectrometry," Molecular & Cellular Proteomics, vol. 12, No. 2, (Nov. 29, 2012), p. 464-472.
Rey, et al., "Addressing proteolytic efficiency in enzymatic degradation therapy for celiac disease," Scientific Reports, vol. 6, (13 pages) (Aug. 2, 2016).
Schendel, PF., "Expression of proteins in *Escherichia coli*," Current Protocols in Molecular Biology, 16.1.1-16.1.3, (1998).
Shan, et al., "Structural basis for gluten intolerance in celiac sprue", Science, (2002), 297:2275-2279.
Slysz, et al., "Hydra: software for tailored processing of H/D exchange daa from MS or tandem MS analyses," BMC Bioinformatics, (2009), 10:162, 1-14.
Stepniak, et al., "Highly efficient gluten degradation with a newly identiifed prolyl endoprotease: implications for celiac disease," AJP Gastrointest Liver Physiol, (2006), 291:G621-G629.
Takahashi, et al., "Nepenthesin, a unique member of a novel subfamily of aspartic proteinases: Enzy matic and structural characteristics," Current Protein & Peptide Science (2005) 6(6):513-525.
Takashai, Kenji, "Nepenthesin," Handbook of Proteolytic Enzymes, vols. 1 and 2, 3rd edition (Nov. 9, 2012), p. 125-128.
Tang, et al., "Preliminary study on the activities of protease in digestive juice of pitcher plant", Genomics and Applied Biology, 2010, 29(2): 293-297. Abstract Only.
Tökés, Zoltán A., et al., "Digestive enzymes secreted by the carnivorous plant *Nepenthes macferlanei* L." Planta 119.1 (1974): 39-46.
Vines, "On the Digestive Ferment of Nepenthes," Journal of Anatomy and Physiology, (1876) 11 (Pt 1):124-127.
Warwood, et al., "Guanidination chemistry for qualitative and quantitative proteomics," Rapid Commun. Mass Spectrom., (2006), 20:3245-3256.

```
N. mirabilis nep I    ----------------MASSLYSFLLALSIVYIFVAPTHSTSR-TALNHHHEPKVAG-----FQIMLEHVDSGKNLTKFELLERAVERGSRRLQR--------LEA
N. alata nep I        ----------------MASSLYSFLLALSIVYIFVAPTHSTSR-TALNHHHEPKVAG-----FQIMLEHVDSGKNLTKFELLERAVERGSRRLQR--------LEA
N. gracilis nep I     ----------------MASPLHSVVLGLAIVSAIVAPTSSTSRGTLLHHGQKRPQPG-----FQIMLEHVDSGKNLTKFQLLERAIERGSRRLQR--------LEA
N. mirabilis nep II   ----------------MASPLHSVVLGLAIVSAIVAPTSSTSRGTLLHHGQKRPQPG-----LRVVLEQVDSGMNLTKYELIKRAIKRGERRMRS--------INA
N. gracilis nep II    ----------------MASPLYSVVLGLAIVSAIVAPTSSTSRGTLLHHGQKRPQPG-----LRVDLEQVDSGKNLTKYELIKRAIKRGERRMRS--------INA
Z. mays nep I         ----------------MAFHSCTIIPASHHSSMSSSTSQMASLAVLVFLVVCATLASGAASVRVGLTRIHSDPDTTAPQFVRDALRRDMHRQRSFGRDRDRE
O. sativa nep I       ----------------------------MRGVSVVLVLIACWLCGCPVAGEAAFAG--DIRVDLTHVDAGKELPKRELIRRAMQRSKARAAALSVVRNGGGF
O. sativa nep II      ---------------MADRITVLAIALLVLILSPQMAVQGKPAAGNTASPRPKQQLGNFFKKHGSDIAGLFPRHRNGGSSGSYSGQAVPAD
O. sativa nep II      MAMMACNNTRPRKLSLPCRTRTFQALILSTAVFLAASTAVVGKEPQPPSSSGGCHYRFELTHVDANLNLTSDELMRRAYDRSRLRAAS----------L
Z. mays nep II N. mirabilis nep I    MLNGPSGVETPVYAGD---------GEYLMNLSIG--TPAQPFSAIMDTGSDLIWTQCQPC-TQCFNQSTPIFNP----QGSSSFSTLPCSSQLCQALQSPT
N. alata nep I        MLNGPSGVETPVYAGD---------GEYLMNLSIG--TPAQPFSAIMDTGSDLIWTQCQPC-TQCFNQSTPIFNP----QGSSSFSTLPCSSQLCQALQSPT
N. gracilis nep I     MLNGPSGVETSVYAGD---------GEYLMNLSIG--TPAQPFSAIMDTGSDLIWTQCQPC-TQCFNQSTPIFNP----QGSSSFSTLPCSSQLCQALSSPT
N. mirabilis nep II   MLQSSSGIETPVYAGS---------GEYLMNVAIG--TPASSLSAIMDTGSDLIWTQCEPC-TQCFSQPTPIFNP----QDSSSFSTLPCESQYCQDLPSES
N. gracilis nep II    MLQSSSGIETPVYAGD---------GEYLMNVAIG--TPDSSLSAIMDTGSDLIWTQCEPC-TQCFSQPTPIFNP----QDSSSFSTLPCESQYCQDLPSET
Z. mays nep I         LAESDGRTSTTVSARTRKDLPNGGEYLMTLAIG--TPPLPYAAVADTGSDLIWTQCAPCGTQCFEQPAPLYNP----ASTTFSVLPCNSSLSMCAGALA
O. sativa nep I       YGSIAQAREREREPGMAVRASGDLEYVLDLAVG----TPPQPITALLDTGSDLIWTQCDTC-TACLRQPDPLFSP----RMSSSYEPMRCAGQLCGDILHHS
O. sativa nep II      GGENGGGQSQDPATN---------TGMYVLSFSVG--TPPQVVTGVLDITSDFVWMQCSACATCGADAPAATSAPPFYAFLSSTIREVRCANRGCQRLVPQT
O. sativa nep II      AAYSDGRHEGRVSIPD---------ASYIITFYLGNQRPEDNISAVVDTGSDIFWTTEKECSRSKTRSMLPCCSP-------KCEQRASCGCGRSELKA
Z. mays nep II N. mirabilis nep I    ----CSNNSCQYTYGYGDGSETQGSMGTETLTFGS------------VSIPNITFGCGE-NNQGFGQNGAGLVGMGRGPLSLPSQLDVTKFSYCMTPIGSS-
N. alata nep I        ----CSNNSCQYTYGYGDGSETQGSMGTETLTFGS------------VSIPNITFGCGE-NNQGFGQNGAGLVGMGRGPLSLPSQLDVTKFSYCMTPIGSS-
N. gracilis nep I     ----CSNNFCQYTYGYGDGSETQGSMGTETLTFGS------------VSIPNITFGCGE-NNQGFGQNGAGLVGMGRGPLSLPSQLDVTKFSYCMTPIGSS-
N. mirabilis nep II   ----CYN-DCQYTYGYGDGSSTQGYMATETFTFET----------SSVPNIAFGCGE-DNQGFGQNGAGLIGMGWGPLSLPSQLGVGQFSYCMTSSGSS-
N. gracilis nep II    ----CNNNECQYTYGYGDGSTTQGYMATETFTFET----------SSVPNIAFGCGE-DNQGFGQNGAGLIGMGWGPLSLPSQLGVGQFSYCMTSYGSS-
Z. mays nep I         GAAPPPGCACMYQTYGTG-WTAGVQGSETFTFGSSA----ADQARVPGVAFGCSN-ASSSDWNG-SAGLVGLGRGSLSLVSQLGAGRFSYCLTPFQDTN
O. sativa nep I       ----CVRPDTCTYRYSYGDGTTTLGYYATERFTFASSS------GETQSVP-LGFGCGT-MNVG-SLNNASGIVGFGRDPLSLVSQLSIRRFSYCLTPYASS-
O. sativa nep II      CSADDSPCGYSYVYGGAANTTAGLLAVDAFAFAT--------VRADGVIFGCAV-ATEG---DIGGVIGLGRGELSPVSQLQIGRFSYYLAPDDAVD
O. sativa nep II      EAEKETKCTYAIIYGNANDSTAGVMYEDKLTIVAVASKAVPSSQSFKEVAIGCSTSATLKFKDPSIKGVFGLGRSATSLPRQLNFSKFSYCLSSYQEPD
Z. mays nep II        
```

FIGURE 1

```
N. mirabilis nep I    TSSTLLLGSLANS-----VTAGSPNTTLIES---SQIPTFYYITLNGLSVGSTPLPIDPSVFKLNSNNGTGGIIIDSGTTLTYFADNAYQAVRQAFISQM
N. alata nep I        NSSTLLLGSLANS-----VTAGSPNTTLIQS---SQIPTFYYITLNGLSVGSTPLPIDPSVFKLNSNNGTGGIIIDSGTTLTYFVDNAYQAVRQAFISQM
N. gracilis nep I     TPSNLLLGSLANS-----VTAGSPNTTLIQS---SQIPTFYYITLNGLSVGSTRLPIDPSAFALNSNNGTGGIIIDSGTTLTYFVNNAYQSVRQEFISQI
N. mirabilis nep II   SPSTLALGSAASG-----VPEGSPSTTLIHS---SLNPTYYYITLQGITVGGDNLGIPSSTFQLQ-DDGTGGMIIDSGTTLTYLPQDAYNAVAQAFTDQI
N. gracilis nep II    SPSTLALGSAASG-----VPEGSPSTTLIHS---SLNPTYYYITLQGITVGGDNLGIPSSTFQLQ-DDGTGGMIIDSGTTLTYLPQDAYNAVAQAFTDQI
Z. mays nep I         STSTLLLGPSAAL-----NGTGVRSTPFVASPARAPMSTYYVLNLTGISLGAKALPISPGAFSLK-PDGTGGLIIDSGTTITSLANAAYQQVRAAVKSQL
O. sativa nep I       RKSTLQFGSLADVGLYDDATGPVQTTPILQS---AQNPTFYYVAFTGVTVGARRLRIPASAFALR-PDGSGGVIIDSGTALTLFPVAVLAEVVRAFRSQL
O. sativa nep II      VGSFILFLDDDAKP----RTSRAVSTPLVAS---RASRSLYYVELAGIRVDGEDLAIPRGTFDLQ-ADGSGGVVLSITIPVTFLDAGAYKVVRQAMASKI
O. sativa nep II      LPSYLLLTAAPDMATGAVGGAAVATTALQP--NSDYKTLYFVHLQNISIGGTRFPAVS-----TKSGGNMFVDTGASFTRLEGTVFAKLVTELDRIM
Z. mays nep II N. mirabilis nep I    N--LSVVNGS-SSGFDLCFQMPSDQSN------LQIPTFVMHFDG-GDLVLPSEN--YFISPSNGLICLAMGSSSQ--GMSIFGNIQQNLLVVYDTGNS
N. alata nep I        N--LSVVNGS-SSGFDLCFQMPSDQSN------LQIPTFVMHFDG-GDLVLPSEN--YFISPSNGLICLAMGSSSQ--GMSIFGNIQQNLLVVYDTGNS
N. gracilis nep I     N--LPVVNGS-SSGFDLCFQTPSDPSN------LQIPTFVMHFDG-GDLELPSEN--YFISPSNGLICLAMGSSSQ--GMSIFGNIQQNMLVVYDTGNS
N. mirabilis nep II   N--LSPVDES-SSGLSTCFQLPSDGST------VQVPEISMQFDG-GVLNLGEEN--VLISPAEGVICLAMGSSQQGISIFGNIQQETQVLYDLQNL
N. gracilis nep II    N--LPTVDES-SSGLSTCFQQPSDGST------VQVPEISMQFDG-GVLNLGEQN--ILISPAEGVICLAMGSSSQLGISIFGNIQQETQVLYDLQNL
Z. mays nep I         VTTLPTVDGSDSTGLDLCFALPAPTSAP-----PAVLPSMTLHFDG-ADMVLPADS--YMISGS-GWCLAMRNQTDGAMSTFGNYQQQNMHILYDVREE
O. sativa nep I       R--LPFANGS-SPDDGVCFAAPAVAAGGGRMARQVAVPRMVFHFQG-ADLDLPREN--YVLEDHRRGHLCVLLGDSGDGATIGNFVQQDMRVVQLERE
O. sativa nep II      E--LRAADGS-ELGLDLCYTSESLATAK-----VPSMALVFAG-GAVMELEMGNYFYMDSTTGLECLTILPSPAGDGSLLGSLIQVGTHMIYDISGS
O. sativa nep II      KERKYVKEQPGRNNGQICYSPPSTAADE-----SSKLPDMVLHFADSANMVLPWDS--YLWKTTSKLCLAIYKSNIKKGISVLGNFQMQNTHMLLDTGNE
Z. mays nep II N. mirabilis nep I    VVSFLFAQCGAS----------- SEQ ID NO.: 5
N. alata nep I        VVSFLSAQCGAS----------- SEQ ID NO.: 6
N. gracilis nep I     VVSFASAQCGAS----------- SEQ ID NO.: 7
N. mirabilis nep II   AVSFVPTQCGAS----------- SEQ ID NO.: 8
N. gracilis nep II    AVSFVPTQCGAS----------- SEQ ID NO.: 9
Z. mays nep I         TLSFAPAKCSTL----------- SEQ ID NO.: 10
O. sativa nep I       TLSFAPVEC-------------- SEQ ID NO.: 11
O. sativa nep II      RLVFESLEQAPPPPSGSSRQSSRRRSSSAPPPLTSPAVVVIHLMLVVVYMFL SEQ ID NO.: 12
O. sativa nep II      KLSFVRADCSKVI---------- SEQ ID NO.: 13
Z. mays nep II
```

FIGURE 1 (Cont.)

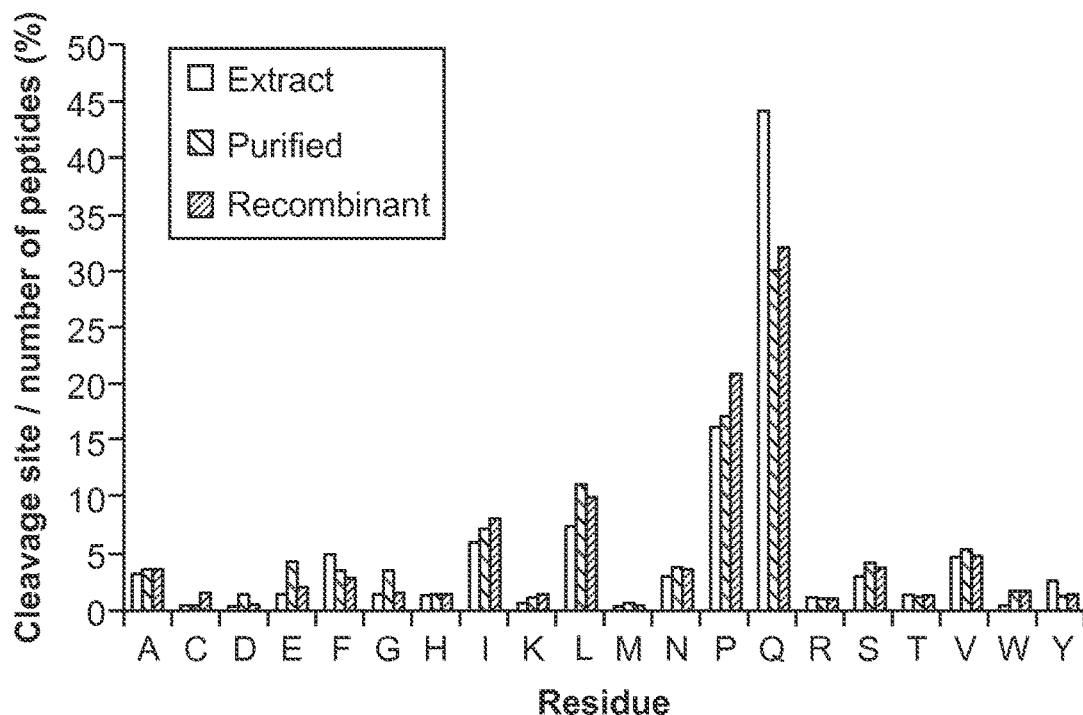
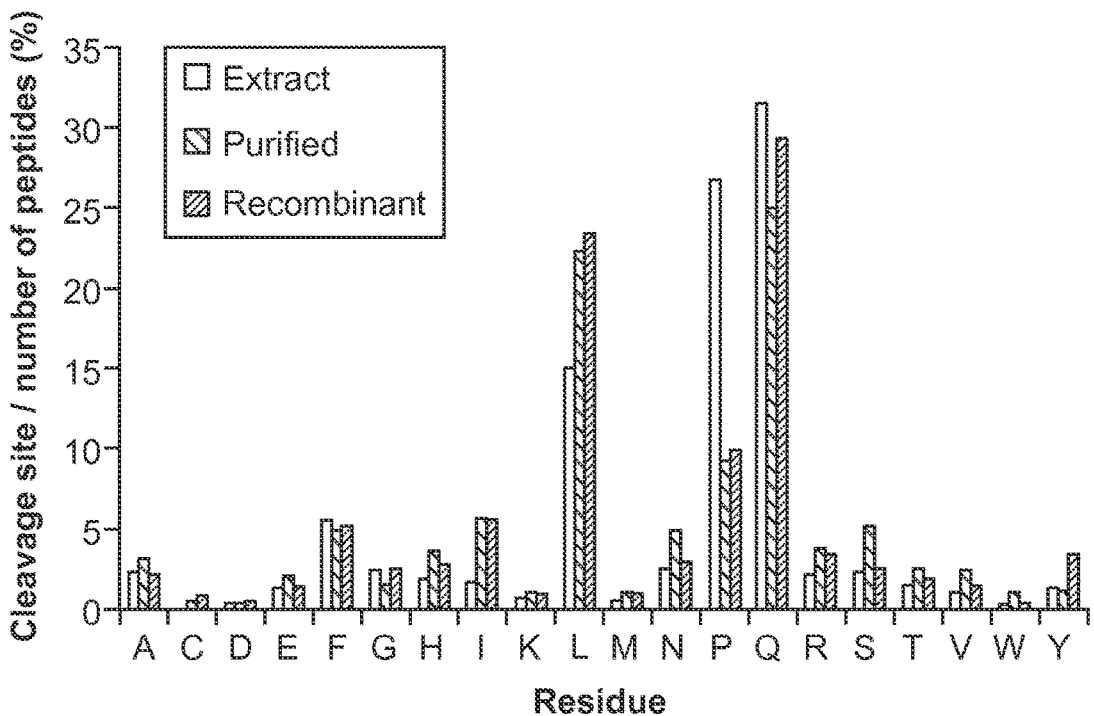
FIGURE 9

Protein sequence coverage: 61%

Matched peptides shown in *bold red*.

```
  1 MKTFLILALL AIVATTATTA VRVPVPQLQP QNPSQQQFQP QVPLVQQQQF
 51 PGQQQQFPPQ QPYPQPQFPP SQQPYLQLQP FPQPQPFPPQ LPYPQPQSFP
101 PQQPYPQQQF QYLQPQQFIS QQQAQQQQQ  QQQSQQQQQI LQQILQQQLI
151 PCRDVVLQQH NIAHASSQVL QQSTYQLLQQ LCCQQLLQIP EQSQCQAIHN
201 VAHAIIMHQQ QQQQPQFQQ  LQQQQQQQQ  LQQQQQQQQ  QFSSQVSFQQ
251 PQQQYPSSQV SFQPSQLNPQ AQSSVQPQQL PQPASIRNLA LQTLPAMCNV
301 YIPPHCSTTI APFGISGTN
```

FIGURE 15B

| Query | Start - End | Observed | Mr(expt) | Mr(calc) | ppm | M | Score | Expect | Rank | U | Peptide |
|---|---|---|---|---|---|---|---|---|---|---|---|
| 60 | 21 - 26 | 333.7181 | 665.4216 | 665.4225 | -1.21 | 0 | 38 | 0.0011 | 1 | | A.VRVPVP.Q |
| 61 | 21 - 26 | 333.7184 | 665.4222 | 665.4225 | -0.31 | 0 | 30 | 0.0011 | 1 | | A.VRVPVP.Q |
| 179 | 21 - 27 | 397.7472 | 793.4798 | 793.4810 | -1.49 | 0 | 28 | 0.0018 | 1 | | A.VRVPVPQ.L |
| 180 | 21 - 27 | 397.7476 | 793.4806 | 793.4810 | -0.49 | 0 | 32 | 0.00064 | 1 | | A.VRVPVPQ.L |
| 488 | 21 - 28 | 454.2898 | 906.5650 | 906.5651 | -0.051 | 0 | 38 | 0.00016 | 1 | | A.VRVPVPQL.Q |
| 821 | 21 - 30 | 566.8456 | 1131.6762 | 1131.6764 | -0.17 | 0 | 35 | 0.00031 | 1 | | A.VRVPVPQLQP.Q |
| 822 | 21 - 30 | 566.8456 | 1131.6766 | 1131.6764 | 0.19 | 0 | 37 | 0.00021 | 1 | | A.VRVPVPQLQP.Q |
| 823 | 21 - 30 | 566.8456 | 1131.6766 | 1131.6764 | 0.19 | 0 | 37 | 0.0002 | 1 | | A.VRVPVPQLQP.Q |
| 1126 | 21 - 31 | 630.8743 | 1259.7340 | 1259.7350 | -0.77 | 0 | 38 | 0.0011 | 1 | | A.VRVPVPQLQPQ.N |
| 1445 | 21 - 33 | 491.2839 | 1470.8299 | 1470.8307 | -0.57 | 0 | 34 | 0.0037 | 1 | | A.VRVPVPQLQPQNP.S |
| 1446 | 21 - 33 | 736.4225 | 1470.8304 | 1470.8307 | -0.17 | 0 | 37 | 0.00029 | 1 | | A.VRVPVPQLQPQNP.S |
| 1447 | 21 - 33 | 491.2841 | 1470.8305 | 1470.8307 | -0.16 | 0 | 34 | 0.004 | 1 | | A.VRVPVPQLQPQNP.S |
| 1448 | 21 - 33 | 736.4227 | 1470.8308 | 1470.8307 | 0.098 | 0 | 38 | 0.00016 | 1 | | A.VRVPVPQLQPQNP.S |
| 1449 | 21 - 33 | 736.4230 | 1470.8314 | 1470.8307 | 0.51 | 0 | 43 | 5.4e-005 | 1 | | A.VRVPVPQLQPQNP.S |
| 1450 | 21 - 33 | 736.4232 | 1470.8318 | 1470.8307 | 0.78 | 0 | 37 | 0.00021 | 1 | | A.VRVPVPQLQPQNP.S |
| 1946 | 21 - 38 | 680.7040 | 2039.0902 | 2039.0912 | -0.52 | 0 | 30 | 0.0012 | 1 | | A.VRVPVPQLQPQNPSQQQP.Q |
| 1947 | 21 - 38 | 680.7043 | 2039.0911 | 2039.0912 | -0.078 | 0 | 25 | 0.0039 | 1 | | A.VRVPVPQLQPQNPSQQQP.Q |
| 1948 | 21 - 38 | 680.7045 | 2039.0917 | 2039.0912 | 0.26 | 0 | 30 | 0.001 | 1 | | A.VRVPVPQLQPQNPSQQQP.Q |
| 1949 | 21 - 38 | 680.7047 | 2039.0923 | 2039.0912 | 0.51 | 0 | 32 | 0.00075 | 1 | | A.VRVPVPQLQPQNPSQQQP.Q |
| 1950 | 21 - 38 | 1020.5538 | 2039.0928 | 2039.0912 | 0.69 | 0 | 27 | 0.0032 | 1 | | A.VRVPVPQLQPQNPSQQQP.Q |
| 1951 | 21 - 38 | 1020.5545 | 2039.0944 | 2039.0912 | 1.58 | 0 | 65 | 0.0036 | 1 | | A.VRVPVPQLQPQNPSQQQP.Q |
| 1952 | 21 - 38 | 1020.5551 | 2039.0956 | 2039.0912 | 2.17 | 0 | 28 | 0.01 | 1 | | A.VRVPVPQLQPQNPSQQQP.Q |
| 222 | 27 - 33 | 413.7157 | 823.4168 | 823.4168 | 0.049 | 0 | 34 | 0.0049 | 1 | | P.QLQPQNP.S |
| 1381 | 27 - 38 | 696.8469 | 1391.6792 | 1391.6793 | -0.064 | 0 | 22 | 0.0086 | 1 | | P.QLQPQNPSQQQP.Q |
| 926 | 29 - 38 | 576.2768 | 1150.5386 | 1150.5367 | 1.78 | 0 | 36 | 0.00033 | 1 | | L.QPQNPSQQQP.Q |
| 927 | 29 - 38 | 576.2771 | 1150.5396 | 1150.5367 | 2.56 | 0 | 35 | 0.00059 | 1 | | L.QPQNPSQQQP.Q |
| 928 | 29 - 38 | 576.2772 | 1150.5398 | 1150.5367 | 2.74 | 0 | 43 | 9.3e-005 | 1 | | L.QPQNPSQQQP.Q |
| 929 | 29 - 38 | 576.2775 | 1150.5404 | 1150.5367 | 3.26 | 0 | 24 | 0.0066 | 1 | | L.QPQNPSQQQP.Q |
| 434 | 31 - 38 | 463.7203 | 925.4260 | 925.4254 | 0.75 | 0 | 42 | 0.00017 | 1 | | P.QNPSQQQP.Q |
| 435 | 31 - 38 | 463.7204 | 925.4262 | 925.4254 | 0.97 | 0 | 34 | 0.00095 | 1 | | P.QNPSQQQP.Q |
| 4 | 39 - 43 | 300.6529 | 599.2912 | 599.2915 | -0.40 | 0 | 17 | 0.018 | 1 | | P.QEQVP.L |
| 5 | 39 - 43 | 300.6532 | 599.2918 | 599.2915 | 0.60 | 0 | 21 | 0.0083 | 1 | | P.QEQVP.L |
| 6 | 39 - 43 | 300.6533 | 599.2920 | 599.2915 | 0.33 | 0 | 16 | 0.029 | 1 | | P.QEQVP.L |
| 7 | 39 - 43 | 300.6533 | 599.2920 | 599.2915 | 0.33 | 0 | 28 | 0.01 | 1 | | P.QEQVP.L |
| 89 | 39 - 44 | 357.1949 | 712.3740 | 712.3755 | -2.11 | 0 | 26 | 0.0023 | 1 | | P.QEQVPL.Y |
| 137 | 42 - 48 | 406.2371 | 810.4596 | 810.4600 | -0.39 | 0 | 26 | 0.003 | 1 | | Q.VPLVQQQ.Q |
| 263 | 44 - 50 | 445.7408 | 889.4654 | 889.4658 | -0.37 | 0 | 16 | 0.03 | 1 | | P.LVQQQQF.P |
| 384 | 44 - 51 | 494.2657 | 986.5168 | 986.5185 | -1.71 | 0 | 16 | 0.023 | 1 | | P.LVQQQQFP.G |

FIGURE 15B (cont.)

| Query | Start – End | Observed | Mr(expt) | Mr(calc) | ppm | M | Score | Expect | Rank | U | Peptide |
|---|---|---|---|---|---|---|---|---|---|---|---|
| 585 | 44 – 51 | 494.2664 | 986.5182 | 986.5185 | -0.29 | 0 | 23 | 0.0055 | 1 | | P.LVQQQQFP.G |
| 586 | 44 – 51 | 494.2665 | 986.5184 | 986.5185 | -0.092 | 0 | 24 | 0.0042 | 1 | | P.LVQQQQFP.G |
| 1886 | 44 – 59 | 633.3234 | 1896.9484 | 1896.9483 | 0.052 | 0 | 30 | 0.0012 | 1 | | P.LVQQQQFPGQQQQFPP.Q |
| 1887 | 44 – 59 | 633.3239 | 1896.9499 | 1896.9483 | 0.84 | 0 | 16 | 0.021 | 1 | | P.LVQQQQFPGQQQQFPP.Q |
| 164 | 46 – 51 | 388.1900 | 774.3654 | 774.3661 | -0.79 | 0 | 20 | 0.022 | 1 | | V.QQQQFP.G |
| 165 | 46 – 51 | 388.1901 | 774.3656 | 774.3661 | -0.53 | 0 | 22 | 0.013 | 1 | | V.QQQQFP.G |
| 167 | 46 – 51 | 388.1903 | 774.3660 | 774.3661 | -0.013 | 0 | 22 | 0.016 | 1 | | V.QQQQFP.G |
| 49 | 47 – 51 | 324.1609 | 646.3072 | 646.3075 | -0.36 | 0 | 19 | 0.047 | 1 | | Q.QQQFP.G |
| 50 | 47 – 51 | 324.1609 | 646.3072 | 646.3075 | -0.36 | 0 | 18 | 0.056 | 1 | | Q.QQQFP.G |
| 51 | 47 – 51 | 324.1609 | 646.3072 | 646.3075 | -0.36 | 0 | 21 | 0.029 | 1 | | Q.QQQFP.G |
| 1199 | 49 – 59 | 651.3184 | 1300.6222 | 1300.6201 | 1.69 | 0 | 17 | 0.024 | 1 | | Q.QFPGQQQQFPP.Q |
| 324 | 54 – 60 | 436.7163 | 871.4180 | 871.4188 | -0.89 | 0 | 14 | 0.16 | 2 | | Q.QQQFPPQ.Q |
| 542 | 55 – 62 | 485.2424 | 968.4702 | 968.4716 | -1.38 | 0 | 20 | 0.058 | 5 | | Q.QQFPPQQP.Y |
| 543 | 55 – 62 | 485.2426 | 968.4706 | 968.4716 | -0.97 | 0 | 14 | 0.24 | 7 | | Q.QQFPPQQP.Y |
| 545 | 55 – 62 | 485.2428 | 968.4710 | 968.4716 | -0.56 | 0 | 20 | 0.069 | 6 | | Q.QQFPPQQP.Y |
| 33 | 60 – 64 | 316.6554 | 631.2962 | 631.2966 | -0.51 | 0 | 21 | 0.044 | 1 | | P.QQFKP.Q |
| 34 | 60 – 64 | 316.6555 | 631.2964 | 631.2966 | -0.19 | 0 | 25 | 0.021 | 1 | | P.QQPYP.Q |
| 140 | 60 – 65 | 380.6855 | 759.3564 | 759.3551 | 1.71 | 0 | 17 | 0.053 | 1 | | P.QQPYPQ.P |
| 302 | 60 – 66 | 429.2106 | 856.4066 | 856.4079 | -1.48 | 0 | 15 | 0.11 | 1 | | P.QQPYPQP.Q |
| 303 | 60 – 66 | 429.2112 | 856.4078 | 856.4079 | -0.076 | 0 | 23 | 0.019 | 2 | | P.QQPYPQP.Q |
| 798 | 60 – 68 | 541.7669 | 1081.5192 | 1081.5193 | -0.0083 | 0 | 33 | 0.0016 | 1 | | P.QQPYPQPQP.F |
| 1077 | 60 – 69 | 615.3012 | 1228.5878 | 1228.5877 | 0.14 | 0 | 26 | 0.0056 | 1 | | P.QQPYPQPQPF.P |
| 1350 | 60 – 71 | 707.3434 | 1412.6722 | 1412.6725 | -0.16 | 0 | 40 | 0.00034 | 1 | | P.QQPYPQPQPFPS.Q |
| 1802 | 60 – 74 | 883.9276 | 1765.8406 | 1765.8424 | -0.99 | 0 | 28 | 0.0027 | 1 | | P.QQPYPQPQPFPSQQP.Y |
| 935 | 65 – 74 | 577.2856 | 1152.5566 | 1152.5564 | 0.23 | 0 | 17 | 0.067 | 2 | | P.QPQPFPSQQP.Y |
| 437 | 67 – 74 | 464.7300 | 927.4454 | 927.4450 | 0.44 | 0 | 28 | 0.0045 | 1 | | P.QPFPSQQP.Y |
| 438 | 67 – 74 | 464.7302 | 927.4458 | 927.4450 | 0.87 | 0 | 30 | 0.0026 | 1 | | P.QPFPSQQP.Y |
| 1594 | 72 – 84 | 528.6124 | 1582.8154 | 1582.8144 | 0.63 | 0 | 23 | 0.0046 | 1 | | S.QQPYLQLQPFPQP.Q |
| 1597 | 72 – 84 | 792.4166 | 1582.8186 | 1582.8144 | 2.70 | 0 | 19 | 0.012 | 1 | | S.QQPYLQLQPFPQP.Q |
| 1416 | 73 – 84 | 728.3838 | 1454.7530 | 1454.7558 | -1.89 | 0 | 16 | 0.046 | 1 | | Q.QPYLQLQPFPQP.Q |
| 1079 | 75 – 84 | 615.8306 | 1229.6466 | 1229.6445 | 1.78 | 0 | 41 | 0.00011 | 1 | | P.YLQLQPFPQP.Q |
| 1080 | 75 – 84 | 615.8311 | 1229.6476 | 1229.6445 | 2.60 | 0 | 29 | 0.0018 | 1 | | P.YLQLQPFPQP.Q |
| 764 | 76 – 84 | 534.2983 | 1066.5820 | 1066.5811 | 0.86 | 0 | 33 | 0.0007 | 1 | | Y.LQLQPFPQP.Q |
| 227 | 78 – 84 | 413.7264 | 825.4382 | 825.4385 | -0.30 | 0 | 33 | 0.00083 | 1 | | Q.LQPFPQP.Q |
| 228 | 78 – 84 | 413.7272 | 825.4398 | 825.4385 | 1.64 | 0 | 34 | 0.00078 | 1 | | Q.LQPFPQP.Q |
| 88 | 79 – 84 | 357.1844 | 712.3542 | 712.3544 | -0.26 | 0 | 21 | 0.051 | 1 | | L.QPFPQP.Q |
| 1155 | 79 – 89 | 640.3262 | 1278.6378 | 1278.6397 | -1.47 | 0 | 39 | 0.0003 | 1 | U | L.QPFPQPQPFPP.Q |
| 1156 | 79 – 89 | 640.3282 | 1278.6418 | 1278.6397 | 1.66 | 0 | 31 | 0.0018 | 1 | U | L.QPFPQPQPFPP.Q |
| 1307 | 81 – 92 | 696.8708 | 1391.7270 | 1391.7238 | 2.34 | 0 | 14 | 0.077 | 1 | U | P.FPQPQPFPPQLP.Y |
| 271 | 90 – 96 | 421.7240 | 841.4334 | 841.4334 | 0.063 | 0 | 20 | 0.03 | 1 | | P.QLPYPQP.Q |
| 272 | 90 – 96 | 421.7242 | 841.4338 | 841.4334 | 0.54 | 0 | 20 | 0.025 | 1 | | P.QLPYPQP.Q |
| 1327 | 90 – 101 | 699.8577 | 1397.7008 | 1397.6980 | 2.07 | 0 | 16 | 0.042 | 1 | | P.QLPYPQPQSFPP.Q |
| 356 | 102 – 108 | 444.7143 | 887.4140 | 887.4137 | 0.36 | 0 | 36 | 0.00035 | 1 | | P.QQPYPQQ.Q |
| 857 | 102 – 110 | 557.2696 | 1112.5246 | 1112.5251 | -0.38 | 0 | 48 | 2.6e-005 | 1 | | P.QQPYPQQQP.Q |
| 858 | 102 – 110 | 557.2698 | 1112.5250 | 1112.5251 | -0.020 | 0 | 54 | 5e-006 | 1 | | P.QQPYPQQQP.Q |
| 577 | 103 – 110 | 493.2389 | 984.4632 | 984.4665 | -3.39 | 0 | 25 | 0.0085 | 2 | | Q.QPYPQQQP.Q |
| 578 | 103 – 110 | 493.2394 | 984.4642 | 984.4665 | -2.28 | 0 | 22 | 0.014 | 3 | | Q.QPYPQQQP.Q |
| 52 | 111 – 115 | 324.6718 | 647.3290 | 647.3279 | 1.83 | 0 | 15 | 0.065 | 1 | U | P.QYLQP.Q |
| 506 | 116 – 123 | 478.7443 | 955.4740 | 955.4723 | 1.82 | 0 | 14 | 0.076 | 1 | | P.QQPISQQQ.A |
| 507 | 116 – 123 | 478.7444 | 955.4742 | 955.4723 | 2.03 | 0 | 29 | 0.0032 | 1 | | P.QQPISQQQ.A |
| 681 | 116 – 124 | 514.2623 | 1026.5100 | 1026.5094 | 0.62 | 0 | 30 | 0.0013 | 1 | | P.QQPISQQQA.Q |
| 682 | 116 – 124 | 514.2626 | 1026.5106 | 1026.5094 | 1.20 | 0 | 33 | 0.00082 | 1 | | P.QQPISQQQA.Q |
| 1347 | 116 – 127 | 706.3503 | 1410.6860 | 1410.6852 | 0.54 | 0 | 21 | 0.015 | 1 | | P.QQPISQQQAQQ.Q |
| 2068 | 116 – 138 | 940.7863 | 2819.3371 | 2819.3295 | 2.68 | 0 | 22 | 0.009 | 1 | | P.QQPISQQQAQQQQQQQQQQQQ.Q |
| 851 | 138 – 146 | 556.3278 | 1110.6410 | 1110.6397 | 1.22 | 0 | 14 | 0.13 | 1 | | Q.QQILQQILQ.Q |
| 301 | 139 – 145 | 428.2692 | 854.5238 | 854.5225 | 1.53 | 0 | 24 | 0.004 | 1 | | Q.QILQQIL.Q |
| 687 | 227 – 234 | 514.7601 | 1027.5056 | 1027.5047 | 0.95 | 0 | 16 | 0.077 | 1 | | P.QQQGLQQQ.Q |
| 1314 | 232 – 242 | 698.8342 | 1395.6538 | 1395.6491 | 3.40 | 0 | 16 | 0.039 | 1 | | L.QQQQQQQQQP.S |
| 1464 | 232 – 243 | 742.3493 | 1482.6840 | 1482.6811 | 1.96 | 0 | 17 | 0.052 | 1 | | L.QQQQQQQQQPS.S |
| 1140 | 233 – 242 | 634.8032 | 1267.5918 | 1267.5905 | 1.04 | 0 | 13 | 0.055 | 1 | | Q.QQQQQQQQP.S |
| 419 | 244 – 251 | 460.7264 | 919.4382 | 919.4400 | -1.86 | 0 | 32 | 0.00068 | 1 | | S.SQVSFQQP.Q |
| 420 | 244 – 251 | 460.7265 | 919.4384 | 919.4400 | -1.64 | 0 | 48 | 1.8e-005 | 1 | | S.SQVSFQQP.Q |
| 391 | 248 – 254 | 452.2192 | 902.4238 | 902.4246 | -0.87 | 0 | 22 | 0.0058 | 1 | | S.FQQFQQQ.Y |
| 533 | 252 – 259 | 483.2206 | 964.4266 | 964.4250 | 1.69 | 0 | 18 | 0.018 | 1 | | P.QQQYPSSQ.V |
| 534 | 252 – 259 | 483.2208 | 964.4270 | 964.4250 | 2.10 | 0 | 24 | 0.0042 | 1 | | P.QQQYPSSQ.V |
| 535 | 252 – 259 | 483.2208 | 964.4270 | 964.4250 | 2.10 | 0 | 17 | 0.021 | 1 | | P.QQQYPSSQ.V |
| 1520 | 252 – 264 | 762.3596 | 1522.7046 | 1522.7052 | -0.38 | 0 | 14 | 0.11 | 1 | U | P.QQQYPSSQVSFQP.S |
| 1646 | 252 – 265 | 805.8761 | 1609.7376 | 1609.7373 | 0.24 | 0 | 36 | 0.00099 | 1 | U | P.QQQYPSSQVSFQPS.Q |
| 1962 | 252 – 269 | 688.3322 | 2061.9748 | 2061.9756 | -0.39 | 0 | 46 | 5.1e-005 | 1 | U | P.QQQYPSSQVSFQPSQLNP.Q |
| 867 | 260 – 269 | 558.7892 | 1115.5618 | 1115.5611 | 0.65 | 0 | 27 | 0.002 | 1 | U | P.VSFQPSQLNP.Q |
| 1586 | 263 – 277 | 789.8979 | 1577.7812 | 1577.7798 | 0.93 | 0 | 28 | 0.0026 | 1 | U | P.QPSQLNPQAQGSVQP.Q |
| 1261 | 265 – 277 | 677.3416 | 1352.6686 | 1352.6684 | 0.15 | 0 | 36 | 0.00036 | 1 | U | P.SQLNPQAQGSVQP.Q |
| 1138 | 266 – 277 | 633.8250 | 1265.6354 | 1265.6364 | -0.76 | 0 | 80 | 1.5e-008 | 1 | U | S.QLNPQAQGSVQP.Q |
| 674 | 268 – 277 | 513.2538 | 1024.4930 | 1024.4935 | -0.71 | 0 | 54 | 8e-006 | 1 | | L.NPQAQGSVQP.Q |
| 410 | 269 – 277 | 456.2332 | 910.4518 | 910.4509 | 1.10 | 0 | 42 | 0.00011 | 1 | | N.PQAQGSVQP.Q |
| 202 | 270 – 277 | 407.7069 | 813.3992 | 813.3981 | 1.43 | 0 | 15 | 0.094 | 1 | | P.QAQGSVQP.Q |
| 203 | 270 – 277 | 407.7071 | 813.3996 | 813.3981 | 1.92 | 0 | 39 | 0.00038 | 1 | | P.QAQGSVQP.Q |

Atty Docket No. 107572-0251

| Query | Start - End | Observed | Mr(expt) | Mr(calc) | ppm | M | Score | Expect | Rank | U | Peptide |
|---|---|---|---|---|---|---|---|---|---|---|---|
| 204 | 270 - 277 | 407.7072 | 813.3998 | 813.3981 | 2.16 | 0 | 26 | 0.006 | 1 | | P.QAQGSVQP.Q |
| 205 | 270 - 277 | 407.7072 | 813.3998 | 813.3981 | 2.16 | 0 | 37 | 0.00047 | 1 | | P.QAQGSVQP.Q |
| 206 | 270 - 277 | 407.7072 | 813.3998 | 813.3981 | 2.16 | 0 | 38 | 0.00038 | 1 | | P.QAQGSVQP.Q |
| 17 | 278 - 282 | 307.1691 | 612.3236 | 612.3231 | 0.86 | 0 | 15 | 0.11 | 1 | | P.QQLPQ.F |
| 141 | 278 - 283 | 380.7031 | 759.3916 | 759.3915 | 0.14 | 0 | 24 | 0.0099 | 1 | | P.QQLPQF.A |
| 143 | 282 - 287 | 382.2074 | 762.4002 | 762.4024 | -2.85 | 0 | 37 | 0.0002 | 1 | | P.QFAEIR.N |
| 331 | 282 - 288 | 439.2299 | 876.4452 | 876.4453 | -0.11 | 0 | 32 | 0.00068 | 1 | | P.QFAEIRN.L |
| 601 | 282 - 289 | 495.7718 | 989.5290 | 989.5294 | -0.36 | 0 | 37 | 0.00019 | 1 | | P.QFAEIRNL.A |
| 602 | 282 - 289 | 495.7720 | 989.5294 | 989.5294 | 0.044 | 0 | 28 | 0.0017 | 1 | | P.QFAEIRNL.A |
| 705 | 286 - 294 | 521.3239 | 1040.6332 | 1040.6342 | -0.92 | 0 | 36 | 0.00024 | 1 | | R.IRNLALQTL.P |
| 319 | 288 - 295 | 435.2585 | 868.5024 | 868.5018 | 0.74 | 0 | 21 | 0.0072 | 1 | | R.NLALQTLP.A |
| 320 | 288 - 295 | 435.2585 | 868.5024 | 868.5018 | 0.74 | 0 | 33 | 0.00051 | 1 | | R.NLALQTLP.A |
| 41 | 290 - 295 | 321.6943 | 641.3740 | 641.3748 | -1.20 | 0 | 25 | 0.0032 | 1 | | L.ALQTLP.A |

FIGURE 16

```
NVEN     1   MQAKFFTFVILSSVFYFNYPLAE  SIQARLANKPKG              53
                                    **
NVEN    54                                                     113
                  *              *           ^ * *
NVEN   114                         IAYFYGNASLQGANATINIWRPNLRNPNGDFSLIQ   173
                                ** *
NVEN   174   IWISAGSGSSLNTIEAGWQVYPGRTGDSQPRFFIYWTADGYTSTGCYDLTCPGFVQTNNY   233
                        ^       *
NVEN   234   YAIGMALQPSVYGGQQYELMESIQRDPATGNGWIYLWGTVVGIWFASIYNSITNGADTVE   293
                       ^              ^
NVEN   194   WGGEIYDSSGTGGFHTTTQMGSGHFPTEGYGKASYVRDL   332
                   * *    /           *        ^          *
NVEN         333   QCVDFYGNVISPTANSFQGIAPAPNCYNYQFQQGSSELYLFYGGPGCQ    380
```

^ Similar; * Non-similar differences

[SP] - [DUF␣␣␣(␣␣-␣␣␣)] - linker - DUF239 (156-387)

Evidence for polymorphisms:
21/380 = 5.5% Total
14/380 = 3.7% non-similar differences

SEQUENCE LISTING

<160> NUMBER OF SEQ ID NOS: 150

<210> SEQ ID NO 1
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gln Ala Lys Phe Phe Thr Phe Val Ile Leu Ser Ser Val Phe Tyr
1               5                   10                  15

Phe Asn Tyr Pro Leu Ala Glu Ala Arg Ser Ile Gln Ala Arg Leu Ala
            20                  25                  30

Asn Lys Pro Lys Gly Thr Ile Lys Thr Ile Lys Gly Asp Asp Gly Glu
        35                  40                  45

Val Val Asp Cys Val Asp Ile Tyr Lys Gln Pro Ala Phe Asp His Pro
    50                  55                  60

Leu Leu Lys Asn His Thr Leu Gln Met Gln Pro Ser Ser Tyr Ala Ser
65                  70                  75                  80

Lys Val Gly Glu Tyr Asn Lys Leu Glu Gln Pro Trp His Lys Asn Gly
                85                  90                  95

Glu Cys Pro Lys Gly Ser Ile Pro Ile Arg Arg Gln Val Ile Thr Gly
            100                 105                 110

Leu Pro Val Val Lys Lys Gln Phe Pro Asn Leu Lys Phe Ala Pro Pro
        115                 120                 125

Ser Ala Asn Thr Asn His Gln Tyr Ala Val Ile Ala Tyr Phe Tyr Gly
    130                 135                 140

Asn Ala Ser Leu Gln Gly Ala Asn Ala Thr Ile Asn Ile Trp Glu Pro
145                 150                 155                 160

Asn Leu Lys Asn Pro Asn Gly Asp Phe Ser Leu Thr Gln Ile Trp Ile
                165                 170                 175

Ser Ala Gly Ser Gly Ser Ser Leu Asn Thr Ile Glu Ala Gly Trp Gln
            180                 185                 190

Val Tyr Pro Gly Arg Thr Gly Asp Ser Gln Pro Arg Phe Phe Ile Tyr
        195                 200                 205

Trp Thr Ala Asp Gly Tyr Thr Ser Thr Gly Cys Tyr Asp Leu Thr Cys
    210                 215                 220

Pro Gly Phe Val Gln Thr Asn Asn Tyr Tyr Ala Ile Gly Met Ala Leu

```
                225                 230                 235                 240
        Gln Pro Ser Val Tyr Gly Gly Gln Gln Tyr Glu Leu Asn Glu Ser Ile
                        245                 250                 255

Gln Arg Asp Pro Ala Thr Gly Asn Trp Trp Leu Tyr Leu Trp Gly Thr
                    260                 265                 270

Val Val Gly Tyr Trp Pro Ala Ser Ile Tyr Asn Ser Ile Thr Asn Gly
                        275                 280                 285

Ala Asp Thr Val Glu Trp Gly Glu Ile Tyr Asp Ser Ser Gly Thr
                290                 295                 300

Gly Gly Phe His Thr Thr Thr Gln Met Gly Ser Gly His Phe Pro Thr
        305                 310                 315                 320

Glu Gly Tyr Gly Lys Ala Ser Tyr Val Arg Asp Leu Gln Cys Val Asp
                        325                 330                 335

Thr Tyr Gly Asn Val Ile Ser Pro Thr Ala Asn Ser Phe Gln Gly Ile
                    340                 345                 350

Ala Pro Ala Pro Asn Cys Tyr Asn Tyr Gln Phe Gln Gln Gly Ser Ser
                    355                 360                 365

Glu Leu Tyr Leu Phe Tyr Gly Gly Pro Gly Cys Gln
                370                 375                 380

<210> SEQ ID NO 2
<211> LENGTH: 1480
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1448)..(1449)
<223> OTHER INFORMATION: a, c, t, g, unknown or other

<400> SEQUENCE: 2
acatggggac ggcctaatta gtaatctcaa gtttgatgtt taaaaggctt caactatgca      60
agctaagttt ttcacatttg ttatactttc ctctgtattt tatttcaact atcctttggc     120
tgaagcaaga tcgattcaag caagattagc caataaacca agggtactat caaaaccat     180 aaagggagat gatggagagg tggttgattg tgttgatata tataagcaac cagcttttga     240
ccacccactt ttaaaaaatc acactttaca gatgcaaccc agttcatacg catccaaggt     300
cggtgaatac aataagcttg aacaaccatg gcataaaaat ggtgagtgcc ctaaaggttc     360
aatcccaatt agaaggcaag ttatcactgg tctccccgtc gtgaaaaaac aatttcctaa     420
cttgaaattt gccccaccaa gtgcaaatac aaaccaccag tatgctgtca ttgcatactt     480
ttacggcaat gcatcattgc aaggagcaaa tgcaaccatt aacatatggg agcccaattt     540
gaaaaaccct aacggggact tcagtcttac tcaaatttgg atctctgctg cagtggatc     600 cagcttgaat accattgagg caggatggca agtgtatcca ggaagaacag gtgactcaca     660
gccaagattt ttcatatatt ggacagccga tggttatact tcgacgggtt gctatgattt     720
aacatgccca ggatttgtgc aaactaacaa ctattatgcc attggtatgg cgttacaacc     780
ctctgtgtac ggcggacaac aatatgagtt aaacgaatcc atacaaaggg acccagcgac     840
cggaaactgg tggctctacc tgtggggac tgttgtcgga tactggccgg cgtcgatata     900
caactccata actaacggtg ccgataccgt agaatgggga ggagagattt acgactcgtc     960
cggaaccggt ggattccaca cgacaactca gatgggaagc ggtcattttc cgaccgaagg    1020
ttatggaaaa gcaagctacg tacgtgatct tcaatgcgta gatacctacg ggaatgtcat    1080
```

```
atctccgacg gcgaacagct tccagggaat agctcctgcg ccgaattgtt ataactatca    1140
gtttcagcaa ggcagctctg aactgtatct cttttacggt ggccctggat gccagtgaat    1200
gaactataat attgcaggcc tctgataata agaggggggag agagagagag aggggggcag   1260
```
```
gaactataat attgcaggcc tctgataata agaggggggag agagagagag aggggggcag    1260
ctggctagcc tataaataag tccacacact gtagctttgt gtttctttga caataatgca    1320
gcggtcatga aggatgttga acgcactagg gcttttcctt ccgttcactt ctgatttgaa    1380
tggatcgaga agacagcatt gaactgtatg acctaaattt ttttctattt attttgatat    1440
caatgggnna aaaaaaaaaa aaaaaaaaa aaaaaaaaa                            1480
```

```
<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ala Lys Phe Phe Thr Phe Val Ile Leu Ser Ser Val Phe Tyr Phe
1               5                   10                  15

Asn Tyr Pro Leu Ala Glu Ala
            20

<210> SEQ ID NO 4
<211> LENGTH: 1234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
acgtcaagaa cagctctcaa tcaccgtcac gaagccaaag taacgggctt tcagataatg     60
cttgaacatg ttgattcggg caaaaactta accaaattcc agctcttaga acgtgctatc    120
gaaaggggta gtcgtagatt gcagaggctc gaagccatgt taaatggccc ctccggtgtg    180
gaaacttccg tctacgccgg agatggcgaa tatctgatga acttatcgat tggaactccg    240
gcacaacctt tctccgcaat catggatacc ggtagcgatc ttatctggac gcagtgccag    300
ccttgcactc agtgtttaa tcaatcaacg cccatattta atcctcaagg atcatcctcc    360
ttctccaccc tcccttgctc aagccaactc tgtcaagccc tttcaagccc gacatgctct    420
aataatttct gccaatacac ctacgggtat ggggacgggt ccgaaaccca aggatccatg    480
ggcactgaga ctctcacttt cgggtcggtt tccatcccta atatcacatt cggctgcggg    540
gaaaacaacc aagggtttgg gcaaggaaac ggggcaggct tggttgggat gggtcggggc    600
cctctgtcgc ttccttctca actcgtcgtg accaaattct cttactgcat gaccccatt    660 ggtagctcaa cccctagcac tcttctattg ggatcactgg ctaattctgt caccgccggt    720
agtcctaata caaccctaat ccaaagctct caaataccaa cttttctatta tattactctc    780 aacgggttga gtgttggttc aactcgcttg cccattgatc cgagtgcttt tgcacttaat    840
agcaataatg gaacaggagg gataataata gactctggaa cgacacttac ttacttcgtt    900
aacgcttatc aatctgtaag gcaagagttc atctcccaga ttaatctacc cgtcgtaaat    960
ggttcctcct ccggctttga tctgtgcttc cagacgcctt ctgatccgtc aaacctgcag   1020
atacccacct ttgtgatgca ttttgacggt ggagatttgg agttgcccag tgagaattat   1080
```

```
ttcatctccc caagcaacgg gctgatttgc ttggcgatgg ggagttcgtc gcagggatg    1140 tccatttttg ggaatattca gcagcaaaac atgctagtcg tttacgacac cggaaattcg    1200
gtggtttcat tcgcttctgc tcaatgtggt gcgt                                1234
```

<210> SEQ ID NO 5
<211> LENGTH: 437
<212> TYPE: PRT
<213> ORGANISM: Nepenthes mirabilis

<400> SEQUENCE: 5

```
Met Ala Ser Ser Leu Tyr Ser Phe Leu Leu Ala Leu Ser Ile Val Tyr
1               5                   10                  15

Ile Phe Val Ala Pro Thr His Ser Thr Ser Arg Thr Ala Leu Asn His
            20                  25                  30

His His Glu Pro Lys Val Ala Gly Phe Gln Ile Met Leu Glu His Val
        35                  40                  45

Asp Ser Gly Lys Asn Leu Thr Lys Phe Glu Leu Leu Glu Arg Ala Val
    50                  55                  60

Glu Arg Gly Ser Arg Arg Leu Gln Arg Leu Glu Ala Met Leu Asn Gly
65                  70                  75                  80

Pro Ser Gly Val Glu Thr Pro Val Tyr Ala Gly Asp Gly Glu Tyr Leu
                85                  90                  95

Met Asn Leu Ser Ile Gly Thr Pro Ala Gln Pro Phe Ser Ala Ile Met
            100                 105                 110

Asp Thr Gly Ser Asp Leu Ile Trp Thr Gln Cys Gln Pro Cys Thr Gln
        115                 120                 125

Cys Phe Asn Gln Ser Thr Pro Ile Phe Asn Pro Gln Gly Ser Ser Ser
    130                 135                 140

Phe Ser Thr Leu Pro Cys Ser Ser Gln Leu Cys Gln Ala Leu Gln Ser
145                 150                 155                 160

Pro Thr Cys Ser Asn Asn Ser Cys Gln Tyr Thr Tyr Gly Tyr Gly Asp
                165                 170                 175

Gly Ser Glu Thr Gln Gly Ser Met Gly Thr Glu Thr Leu Thr Phe Gly
            180                 185                 190

Ser Val Ser Ile Pro Asn Ile Thr Phe Gly Cys Gly Glu Asn Asn Gln
        195                 200                 205

Gly Phe Gly Gln Gly Asn Gly Ala Gly Leu Val Gly Met Gly Arg Gly
    210                 215                 220

Pro Leu Ser Leu Pro Ser Gln Leu Asp Val Thr Lys Phe Ser Tyr Cys
225                 230                 235                 240

Met Thr Pro Ile Gly Ser Ser Thr Ser Thr Leu Leu Gly Ser
                245                 250                 255

Leu Ala Asn Ser Val Thr Ala Gly Ser Pro Asn Thr Thr Leu Ile Glu
            260                 265                 270

Ser Ser Gln Ile Pro Thr Phe Tyr Tyr Ile Thr Leu Asn Gly Leu Ser
        275                 280                 285

Val Gly Ser Thr Pro Leu Pro Ile Asp Pro Ser Val Phe Lys Leu Asn
    290                 295                 300

Ser Asn Asn Gly Thr Gly Gly Ile Ile Ile Asp Ser Gly Thr Thr Leu
305                 310                 315                 320

Thr Tyr Phe Ala Asp Asn Ala Tyr Gln Ala Val Arg Gln Ala Phe Ile
                325                 330                 335

Ser Gln Met Asn Leu Ser Val Val Asn Gly Ser Ser Ser Gly Phe Asp
            340                 345                 350
```

```
Leu Cys Phe Gln Met Pro Ser Asp Gln Ser Asn Leu Gln Ile Pro Thr
            355                 360                 365

Phe Val Met His Phe Asp Gly Gly Asp Leu Val Leu Pro Ser Glu Asn
370                 375                 380

Tyr Phe Ile Ser Pro Ser Asn Gly Leu Ile Cys Leu Ala Met Gly Ser
385                 390                 395                 400

Ser Ser Gln Gly Met Ser Ile Phe Gly Asn Ile Gln Gln Gln Asn Leu
            405                 410                 415

Leu Val Val Tyr Asp Thr Gly Asn Ser Val Val Ser Phe Leu Phe Ala
            420                 425                 430

Gln Cys Gly Ala Ser
            435

<210> SEQ ID NO 6
<211> LENGTH: 437
<212> TYPE: PRT
<213> ORGANISM: Nepenthes alata

<400> SEQUENCE: 6

Met Ala Ser Ser Leu Tyr Ser Phe Leu Leu Ala Leu Ser Ile Val Tyr
1               5                   10                  15

Ile Phe Val Ala Pro Thr His Ser Thr Ser Arg Thr Ala Leu Asn His
                20                  25                  30

His His Glu Pro Lys Val Ala Gly Phe Gln Ile Met Leu Glu His Val
            35                  40                  45

Asp Ser Gly Lys Asn Leu Thr Lys Phe Glu Leu Leu Glu Arg Ala Val
        50                  55                  60

Glu Arg Gly Ser Arg Arg Leu Gln Arg Leu Glu Ala Met Leu Asn Gly
65                  70                  75                  80

Pro Ser Gly Val Glu Thr Pro Val Tyr Ala Gly Asp Gly Glu Tyr Leu
                85                  90                  95

Met Asn Leu Ser Ile Gly Thr Pro Ala Gln Pro Phe Ser Ala Ile Met
            100                 105                 110

Asp Thr Gly Ser Asp Leu Ile Trp Thr Gln Cys Gln Pro Cys Thr Gln
        115                 120                 125

Cys Phe Asn Gln Ser Thr Pro Ile Phe Asn Pro Gln Gly Ser Ser Ser
    130                 135                 140

Phe Ser Thr Leu Pro Cys Ser Ser Gln Leu Cys Gln Ala Leu Gln Ser
145                 150                 155                 160

Pro Thr Cys Ser Asn Asn Ser Cys Gln Tyr Thr Tyr Gly Tyr Gly Asp
                165                 170                 175

Gly Ser Glu Thr Gln Gly Ser Met Gly Thr Glu Thr Leu Thr Phe Gly
            180                 185                 190

Ser Val Ser Ile Pro Asn Ile Thr Phe Gly Cys Gly Glu Asn Asn Gln
        195                 200                 205

Gly Phe Gly Gln Gly Asn Gly Ala Gly Leu Val Gly Met Gly Arg Gly
    210                 215                 220

Pro Leu Ser Leu Pro Ser Gln Leu Asp Val Thr Lys Phe Ser Tyr Cys
225                 230                 235                 240

Met Thr Pro Ile Gly Ser Ser Asn Ser Ser Thr Leu Leu Leu Gly Ser
                245                 250                 255

Leu Ala Asn Ser Val Thr Ala Gly Ser Pro Asn Thr Thr Leu Ile Gln
            260                 265                 270

Ser Ser Gln Ile Pro Thr Phe Tyr Tyr Ile Thr Leu Asn Gly Leu Ser
```

```
            275                 280                 285
Val Gly Ser Thr Pro Leu Pro Ile Asp Pro Ser Val Phe Lys Leu Asn
    290                 295                 300

Ser Asn Asn Gly Thr Gly Gly Ile Ile Ile Asp Ser Gly Thr Thr Leu
305                 310                 315                 320

Thr Tyr Phe Val Asp Asn Ala Tyr Gln Ala Val Arg Gln Ala Phe Ile
                325                 330                 335

Ser Gln Met Asn Leu Ser Val Val Asn Gly Ser Ser Ser Gly Phe Asp
                340                 345                 350

Leu Cys Phe Gln Met Pro Ser Asp Gln Ser Asn Leu Gln Ile Pro Thr
            355                 360                 365

Phe Val Met His Phe Asp Gly Asp Leu Val Leu Pro Ser Glu Asn
    370                 375                 380

Tyr Phe Ile Ser Pro Ser Asn Gly Leu Ile Cys Leu Ala Met Gly Ser
385                 390                 395                 400

Ser Ser Gln Gly Met Ser Ile Phe Gly Asn Ile Gln Gln Gln Asn Leu
                405                 410                 415

Leu Val Val Tyr Asp Thr Gly Asn Ser Val Val Ser Phe Leu Ser Ala
                420                 425                 430

Gln Cys Gly Ala Ser
            435

<210> SEQ ID NO 7
<211> LENGTH: 437
<212> TYPE: PRT
<213> ORGANISM: Nepenthes gracilis

<400> SEQUENCE: 7

Met Ala Ser Ser Leu Tyr Ser Phe Leu Leu Ala Leu Ser Ile Val Tyr
1               5                   10                  15

Ile Phe Val Ala Pro Thr His Ser Thr Ser Arg Thr Ala Leu Asn His
                20                  25                  30

Arg His Glu Ala Lys Val Thr Gly Phe Gln Ile Met Leu Glu His Val
            35                  40                  45

Asp Ser Gly Lys Asn Leu Thr Lys Phe Gln Leu Leu Glu Arg Ala Ile
        50                  55                  60

Glu Arg Gly Ser Arg Arg Leu Gln Arg Leu Glu Ala Met Leu Asn Gly
65                  70                  75                  80

Pro Ser Gly Val Glu Thr Ser Val Tyr Ala Gly Asp Gly Glu Tyr Leu
                85                  90                  95

Met Asn Leu Ser Ile Gly Thr Pro Ala Gln Pro Phe Ser Ala Ile Met
                100                 105                 110

Asp Thr Gly Ser Asp Leu Ile Trp Thr Gln Cys Gln Pro Cys Thr Gln
            115                 120                 125

Cys Phe Asn Gln Ser Thr Pro Ile Phe Asn Pro Gln Gly Ser Ser Ser
130                 135                 140

Phe Ser Thr Leu Pro Cys Ser Ser Gln Leu Cys Gln Ala Leu Ser Ser
145                 150                 155                 160

Pro Thr Cys Ser Asn Asn Phe Cys Gln Tyr Thr Tyr Gly Tyr Gly Asp
                165                 170                 175

Gly Ser Glu Thr Gln Gly Ser Met Gly Thr Glu Thr Leu Thr Phe Gly
            180                 185                 190

Ser Val Ser Ile Pro Asn Ile Thr Phe Gly Cys Gly Glu Asn Asn Gln
        195                 200                 205
```

Gly Phe Gly Gln Gly Asn Gly Ala Gly Leu Val Gly Met Gly Arg Gly
    210                 215                 220

Pro Leu Ser Leu Pro Ser Gln Leu Asp Val Thr Lys Phe Ser Tyr Cys
225                 230                 235                 240

Met Thr Pro Ile Gly Ser Ser Thr Pro Ser Asn Leu Leu Gly Ser
            245                 250                 255

Leu Ala Asn Ser Val Thr Ala Gly Ser Pro Asn Thr Thr Leu Ile Gln
            260                 265                 270

Ser Ser Gln Ile Pro Thr Phe Tyr Tyr Ile Thr Leu Asn Gly Leu Ser
        275                 280                 285

Val Gly Ser Thr Arg Leu Pro Ile Asp Pro Ser Ala Phe Ala Leu Asn
    290                 295                 300

Ser Asn Asn Gly Thr Gly Gly Ile Ile Ile Asp Ser Gly Thr Thr Leu
305                 310                 315                 320

Thr Tyr Phe Val Asn Asn Ala Tyr Gln Ser Val Arg Gln Glu Phe Ile
                325                 330                 335

Ser Gln Ile Asn Leu Pro Val Val Asn Gly Ser Ser Gly Phe Asp
            340                 345                 350

Leu Cys Phe Gln Thr Pro Ser Asp Pro Ser Asn Leu Gln Ile Pro Thr
        355                 360                 365

Phe Val Met His Phe Asp Gly Gly Asp Leu Glu Leu Pro Ser Glu Asn
    370                 375                 380

Tyr Phe Ile Ser Pro Ser Asn Gly Leu Ile Cys Leu Ala Met Gly Ser
385                 390                 395                 400

Ser Ser Gln Gly Met Ser Ile Phe Gly Asn Ile Gln Gln Gln Asn Met
                405                 410                 415

Leu Val Val Tyr Asp Thr Gly Asn Ser Val Val Ser Phe Ala Ser Ala
            420                 425                 430

Gln Cys Gly Ala Ser
        435

<210> SEQ ID NO 8
<211> LENGTH: 437
<212> TYPE: PRT
<213> ORGANISM: Nepenthes mirabilis

<400> SEQUENCE: 8

Met Ala Ser Pro Leu His Ser Val Val Leu Gly Leu Ala Ile Val Ser
1               5                   10                  15

Ala Ile Val Ala Pro Thr Ser Ser Thr Ser Arg Gly Thr Leu Leu His
            20                  25                  30

His Gly Gln Lys Arg Pro Gln Pro Gly Leu Arg Val Val Leu Glu Gln
        35                  40                  45

Val Asp Ser Gly Met Asn Leu Thr Lys Tyr Glu Leu Ile Lys Arg Ala
    50                  55                  60

Ile Lys Arg Gly Glu Arg Arg Met Arg Ser Ile Asn Ala Met Leu Gln
65                  70                  75                  80

Ser Ser Ser Gly Ile Glu Thr Pro Val Tyr Ala Gly Ser Gly Glu Tyr
                85                  90                  95

Leu Met Asn Val Ala Ile Gly Thr Pro Ala Ser Ser Leu Ser Ala Ile
            100                 105                 110

Met Asp Thr Gly Ser Asp Leu Ile Trp Thr Gln Cys Glu Pro Cys Thr
        115                 120                 125

Gln Cys Phe Ser Gln Pro Thr Pro Ile Phe Asn Pro Gln Asp Ser Ser
    130                 135                 140

-continued

```
Ser Phe Ser Thr Leu Pro Cys Glu Ser Gln Tyr Cys Gln Asp Leu Pro
145                 150                 155                 160

Ser Glu Ser Cys Tyr Asn Asp Cys Gln Tyr Thr Tyr Gly Tyr Gly Asp
                165                 170                 175

Gly Ser Ser Thr Gln Gly Tyr Met Ala Thr Glu Thr Phe Thr Phe Glu
            180                 185                 190

Thr Ser Ser Val Pro Asn Ile Ala Phe Gly Cys Gly Glu Asp Asn Gln
            195                 200                 205

Gly Phe Gly Gln Gly Asn Gly Ala Gly Leu Ile Gly Met Gly Trp Gly
        210                 215                 220

Pro Leu Ser Leu Pro Ser Gln Leu Gly Val Gly Gln Phe Ser Tyr Cys
225                 230                 235                 240

Met Thr Ser Ser Gly Ser Ser Ser Pro Ser Thr Leu Ala Leu Gly Ser
                245                 250                 255

Ala Ala Ser Gly Val Pro Glu Gly Ser Pro Ser Thr Thr Leu Ile His
            260                 265                 270

Ser Ser Leu Asn Pro Thr Tyr Tyr Tyr Ile Thr Leu Gln Gly Ile Thr
        275                 280                 285

Val Gly Gly Asp Asn Leu Gly Ile Pro Ser Ser Thr Phe Gln Leu Gln
290                 295                 300

Asp Asp Gly Thr Gly Gly Met Ile Ile Asp Ser Gly Thr Thr Leu Thr
305                 310                 315                 320

Tyr Leu Pro Gln Asp Ala Tyr Asn Ala Val Ala Gln Ala Phe Thr Asp
                325                 330                 335

Gln Ile Asn Leu Ser Pro Val Asp Glu Ser Ser Ser Gly Leu Ser Thr
            340                 345                 350

Cys Phe Gln Leu Pro Ser Asp Gly Ser Thr Val Gln Val Pro Glu Ile
        355                 360                 365

Ser Met Gln Phe Asp Gly Gly Val Leu Asn Leu Gly Glu Glu Asn Val
370                 375                 380

Leu Ile Ser Pro Ala Glu Gly Val Ile Cys Leu Ala Met Gly Ser Ser
385                 390                 395                 400

Ser Gln Gln Gly Ile Ser Ile Phe Gly Asn Ile Gln Gln Gln Glu Thr
                405                 410                 415

Gln Val Leu Tyr Asp Leu Gln Asn Leu Ala Val Ser Phe Val Pro Thr
            420                 425                 430

Gln Cys Gly Ala Ser
        435

<210> SEQ ID NO 9
<211> LENGTH: 438
<212> TYPE: PRT
<213> ORGANISM: Nepenthes gracilis

<400> SEQUENCE: 9

Met Ala Ser Pro Leu Tyr Ser Val Val Leu Gly Leu Ala Ile Val Ser
1               5                   10                  15

Ala Ile Val Ala Pro Thr Ser Ser Thr Ser Arg Gly Thr Leu Leu His
            20                  25                  30

His Gly Gln Lys Arg Pro Gln Pro Gly Leu Arg Val Asp Leu Glu Gln
        35                  40                  45

Val Asp Ser Gly Lys Asn Leu Thr Lys Tyr Glu Leu Ile Lys Arg Ala
50                  55                  60

Ile Lys Arg Gly Glu Arg Arg Met Arg Ser Ile Asn Ala Met Leu Gln
```

```
            65                  70                  75                  80

Ser Ser Ser Gly Ile Glu Thr Pro Val Tyr Ala Gly Asp Gly Glu Tyr
                        85                  90                  95

Leu Met Asn Val Ala Ile Gly Thr Pro Asp Ser Ser Phe Ser Ala Ile
                       100                 105                 110

Met Asp Thr Gly Ser Asp Leu Ile Trp Thr Gln Cys Glu Pro Cys Thr
                       115                 120                 125

Gln Cys Phe Ser Gln Pro Thr Pro Ile Phe Asn Pro Gln Asp Ser Ser
                       130                 135                 140

Ser Phe Ser Thr Leu Pro Cys Glu Ser Gln Tyr Cys Gln Asp Leu Pro
        145                 150                 155                 160

Ser Glu Thr Cys Asn Asn Glu Cys Gln Tyr Thr Tyr Gly Tyr Tyr Gly
                            165                 170                 175

Asp Gly Ser Thr Thr Gln Gly Tyr Met Ala Thr Glu Thr Phe Thr Phe
                       180                 185                 190

Glu Thr Ser Ser Val Pro Asn Ile Ala Phe Gly Cys Gly Glu Asp Asn
                       195                 200                 205

Gln Gly Phe Gly Gln Gly Asn Gly Ala Gly Leu Ile Gly Met Gly Trp
                       210                 215                 220

Gly Pro Leu Ser Leu Pro Ser Gln Leu Gly Val Gly Gln Phe Ser Tyr
        225                 230                 235                 240

Cys Met Thr Ser Tyr Gly Ser Ser Pro Ser Thr Leu Ala Leu Gly
                            245                 250                 255

Ser Ala Ala Ser Gly Val Pro Glu Gly Ser Pro Ser Thr Thr Leu Ile
                       260                 265                 270

His Ser Ser Leu Asn Pro Thr Tyr Tyr Tyr Ile Thr Leu Gln Gly Ile
                       275                 280                 285

Thr Val Gly Gly Asp Asn Leu Gly Ile Pro Ser Ser Thr Phe Gln Leu
                       290                 295                 300

Gln Asp Asp Gly Thr Gly Gly Met Ile Ile Asp Ser Gly Thr Thr Leu
        305                 310                 315                 320

Thr Tyr Leu Pro Gln Asp Ala Tyr Asn Ala Val Ala Gln Ala Phe Thr
                       325                 330                 335

Asp Gln Ile Asn Leu Pro Thr Val Asp Glu Ser Ser Gly Leu Ser
                       340                 345                 350

Thr Cys Phe Gln Gln Pro Ser Asp Gly Ser Thr Val Gln Val Pro Glu
                       355                 360                 365

Ile Ser Met Gln Phe Asp Gly Gly Val Leu Asn Leu Gly Glu Gln Asn
                       370                 375                 380

Ile Leu Ile Ser Pro Ala Glu Gly Val Ile Cys Leu Ala Met Gly Ser
        385                 390                 395                 400

Ser Ser Gln Leu Gly Ile Ser Ile Phe Gly Asn Ile Gln Gln Gln Glu
                       405                 410                 415

Thr Gln Val Leu Tyr Asp Leu Gln Asn Leu Ala Val Ser Phe Val Pro
                       420                 425                 430

Thr Gln Cys Gly Ala Ser
                       435

<210> SEQ ID NO 10
<211> LENGTH: 472
<212> TYPE: PRT
<213> ORGANISM: Zea mays

<400> SEQUENCE: 10
```

-continued

```
Met Ala Phe His Ser Cys Thr Ile Ile Pro Ala Ser His His Ser Ser
1               5                   10                  15

Met Ser Ser Ser Thr Ser Gln Met Ala Ser Leu Ala Val Leu Val Phe
            20                  25                  30

Leu Val Val Cys Ala Thr Leu Ala Ser Gly Ala Ala Ser Val Arg Val
            35                  40                  45

Gly Leu Thr Arg Ile His Ser Asp Pro Asp Thr Thr Ala Pro Gln Phe
        50                  55                  60

Val Arg Asp Ala Leu Arg Arg Asp Met His Arg Gln Arg Ser Arg Ser
65                  70                  75                  80

Phe Gly Arg Asp Arg Asp Arg Glu Leu Ala Glu Ser Asp Gly Arg Thr
                85                  90                  95

Ser Thr Thr Val Ser Ala Arg Thr Arg Lys Asp Leu Pro Asn Gly Gly
                100                 105                 110

Glu Tyr Leu Met Thr Leu Ala Ile Gly Thr Pro Pro Leu Pro Tyr Ala
            115                 120                 125

Ala Val Ala Asp Thr Gly Ser Asp Leu Ile Trp Thr Gln Cys Ala Pro
        130                 135                 140

Cys Gly Thr Gln Cys Phe Glu Gln Pro Ala Pro Leu Tyr Asn Pro Ala
145                 150                 155                 160

Ser Ser Thr Thr Phe Ser Val Leu Pro Cys Asn Ser Ser Leu Ser Met
                165                 170                 175

Cys Ala Gly Ala Leu Ala Gly Ala Ala Pro Pro Pro Gly Cys Ala Cys
            180                 185                 190

Met Tyr Tyr Gln Thr Tyr Gly Thr Gly Trp Thr Ala Gly Val Gln Gly
            195                 200                 205

Ser Glu Thr Phe Thr Phe Gly Ser Ser Ala Ala Asp Gln Ala Arg Val
        210                 215                 220

Pro Gly Val Ala Phe Gly Cys Ser Asn Ala Ser Ser Ser Asp Trp Asn
225                 230                 235                 240

Gly Ser Ala Gly Leu Val Gly Leu Gly Arg Gly Ser Leu Ser Leu Val
                245                 250                 255

Ser Gln Leu Gly Ala Gly Arg Phe Ser Tyr Cys Leu Thr Pro Phe Gln
            260                 265                 270

Asp Thr Asn Ser Thr Ser Thr Leu Leu Leu Gly Pro Ser Ala Ala Leu
        275                 280                 285

Asn Gly Thr Gly Val Arg Ser Thr Pro Phe Val Ala Ser Pro Ala Arg
    290                 295                 300

Ala Pro Met Ser Thr Tyr Tyr Tyr Leu Asn Leu Thr Gly Ile Ser Leu
305                 310                 315                 320

Gly Ala Lys Ala Leu Pro Ile Ser Pro Gly Ala Phe Ser Leu Lys Pro
                325                 330                 335

Asp Gly Thr Gly Gly Leu Ile Ile Asp Ser Gly Thr Ile Thr Ser
            340                 345                 350

Leu Ala Asn Ala Ala Tyr Gln Gln Val Arg Ala Ala Val Lys Ser Gln
        355                 360                 365

Leu Val Thr Thr Leu Pro Thr Val Asp Gly Ser Asp Ser Thr Gly Leu
    370                 375                 380

Asp Leu Cys Phe Ala Leu Pro Ala Pro Thr Ser Ala Pro Pro Ala Val
385                 390                 395                 400

Leu Pro Ser Met Thr Leu His Phe Asp Gly Ala Asp Met Val Leu Pro
                405                 410                 415

Ala Asp Ser Tyr Met Ile Ser Gly Ser Gly Val Trp Cys Leu Ala Met
```

```
                420             425             430
Arg Asn Gln Thr Asp Gly Ala Met Ser Thr Phe Gly Asn Tyr Gln Gln
            435             440             445

Gln Asn Met His Ile Leu Tyr Asp Val Arg Glu Glu Thr Leu Ser Phe
450             455             460

Ala Pro Ala Lys Cys Ser Thr Leu
465             470

<210> SEQ ID NO 11
<211> LENGTH: 453
<212> TYPE: PRT
<213> ORGANISM: Oryza sativa

<400> SEQUENCE: 11

Met Arg Gly Val Ser Val Leu Val Leu Ile Ala Cys Trp Leu Cys
1               5                   10                  15

Gly Cys Pro Val Ala Gly Glu Ala Ala Phe Ala Gly Asp Ile Arg Val
                20                  25                  30

Asp Leu Thr His Val Asp Ala Gly Lys Glu Leu Pro Lys Arg Glu Leu
            35                  40                  45

Ile Arg Arg Ala Met Gln Arg Ser Lys Ala Arg Ala Ala Leu Ser
50                  55                  60

Val Val Arg Asn Gly Gly Phe Tyr Gly Ser Ile Ala Gln Ala Arg
65                  70                  75                  80

Glu Arg Glu Arg Glu Pro Gly Met Ala Val Arg Ala Ser Gly Asp Leu
                85                  90                  95

Glu Tyr Val Leu Asp Leu Ala Val Gly Thr Pro Pro Gln Pro Ile Thr
            100                 105                 110

Ala Leu Leu Asp Thr Gly Ser Asp Leu Ile Trp Thr Gln Cys Asp Thr
            115                 120                 125

Cys Thr Ala Cys Leu Arg Gln Pro Asp Pro Leu Phe Ser Pro Arg Met
130                 135                 140

Ser Ser Ser Tyr Glu Pro Met Arg Cys Ala Gly Gln Leu Cys Gly Asp
145                 150                 155                 160

Ile Leu His His Ser Cys Val Arg Pro Asp Thr Cys Thr Tyr Arg Tyr
                165                 170                 175

Ser Tyr Gly Asp Gly Thr Thr Thr Leu Gly Tyr Tyr Ala Thr Glu Arg
            180                 185                 190

Phe Thr Phe Ala Ser Ser Ser Gly Glu Thr Gln Ser Val Pro Leu Gly
        195                 200                 205

Phe Gly Cys Gly Thr Met Asn Val Gly Ser Leu Asn Asn Ala Ser Gly
    210                 215                 220

Ile Val Gly Phe Gly Arg Asp Pro Leu Ser Leu Val Ser Gln Leu Ser
225                 230                 235                 240

Ile Arg Arg Phe Ser Tyr Cys Leu Thr Pro Tyr Ala Ser Ser Arg Lys
                245                 250                 255

Ser Thr Leu Gln Phe Gly Ser Leu Ala Asp Val Gly Leu Tyr Asp Asp
            260                 265                 270

Ala Thr Gly Pro Val Gln Thr Thr Pro Ile Leu Gln Ser Ala Gln Asn
        275                 280                 285

Pro Thr Phe Tyr Tyr Val Ala Phe Thr Gly Val Thr Val Gly Ala Arg
    290                 295                 300

Arg Leu Arg Ile Pro Ala Ser Ala Phe Ala Leu Arg Pro Asp Gly Ser
305                 310                 315                 320
```

```
Gly Gly Val Ile Ile Asp Ser Gly Thr Ala Leu Thr Leu Phe Pro Val
                325                 330                 335

Ala Val Leu Ala Glu Val Val Arg Ala Phe Arg Ser Gln Leu Arg Leu
        340                 345                 350

Pro Phe Ala Asn Gly Ser Ser Pro Asp Asp Gly Val Cys Phe Ala Ala
            355                 360                 365

Pro Ala Val Ala Ala Gly Gly Arg Met Ala Arg Gln Val Ala Val
    370                 375                 380

Pro Arg Met Val Phe His Phe Gln Gly Ala Asp Leu Asp Leu Pro Arg
385                 390                 395                 400

Glu Asn Tyr Val Leu Glu Asp His Arg Arg Gly His Leu Cys Val Leu
                405                 410                 415

Leu Gly Asp Ser Gly Asp Asp Gly Ala Thr Ile Gly Asn Phe Val Gln
                420                 425                 430

Gln Asp Met Arg Val Val Tyr Asp Leu Glu Arg Glu Thr Leu Ser Phe
            435                 440                 445

Ala Pro Val Glu Cys
    450

<210> SEQ ID NO 12
<211> LENGTH: 486
<212> TYPE: PRT
<213> ORGANISM: Oryza sativa

<400> SEQUENCE: 12

Met Ala Asp Arg Ile Thr Val Leu Ala Ile Ala Leu Leu Val Leu Ile
1               5                   10                  15

Leu Ser Pro Gln Met Ala Val Gln Gly Lys Pro Ala Ala Gly Asn Thr
                20                  25                  30

Ala Ser Pro Arg Pro Lys Gln Gln Leu Gly Asn Phe Phe Lys Lys
            35                  40                  45

His Gly Ser Asp Ile Ala Gly Leu Phe Pro Arg His Arg Asn Gly Gly
    50                  55                  60

Ser Ser Gly Ser Tyr Ser Gly Gln Ala Val Pro Ala Asp Gly Gly Glu
65                  70                  75                  80

Asn Gly Gly Gly Gln Ser Gln Asp Pro Ala Thr Asn Thr Gly Met
                85                  90                  95

Tyr Val Leu Ser Phe Ser Val Gly Thr Pro Pro Gln Val Thr Gly
                100                 105                 110

Val Leu Asp Ile Thr Ser Asp Phe Val Trp Met Gln Cys Ser Ala Cys
            115                 120                 125

Ala Thr Cys Gly Ala Asp Ala Pro Ala Ala Thr Ser Ala Pro Pro Phe
130                 135                 140

Tyr Ala Phe Leu Ser Ser Thr Ile Arg Glu Val Arg Cys Ala Asn Arg
145                 150                 155                 160

Gly Cys Gln Arg Leu Val Pro Gln Thr Cys Ser Ala Asp Asp Ser Pro
                165                 170                 175

Cys Gly Tyr Ser Tyr Val Tyr Gly Gly Gly Ala Ala Asn Thr Thr Ala
            180                 185                 190

Gly Leu Leu Ala Val Asp Ala Phe Ala Phe Ala Thr Arg Ala Asp
        195                 200                 205

Gly Val Ile Phe Gly Cys Ala Val Ala Thr Glu Gly Asp Ile Gly Gly
    210                 215                 220

Val Ile Gly Leu Gly Arg Gly Glu Leu Ser Pro Val Ser Gln Leu Gln
225                 230                 235                 240
```

-continued

Ile Gly Arg Phe Ser Tyr Tyr Leu Ala Pro Asp Asp Ala Val Asp Val
            245                 250                 255

Gly Ser Phe Ile Leu Phe Leu Asp Asp Ala Lys Pro Arg Thr Ser Arg
        260                 265                 270

Ala Val Ser Thr Pro Leu Val Ala Ser Arg Ala Ser Arg Ser Leu Tyr
    275                 280                 285

Tyr Val Glu Leu Ala Gly Ile Arg Val Asp Gly Glu Asp Leu Ala Ile
290                 295                 300

Pro Arg Gly Thr Phe Asp Leu Gln Ala Asp Gly Ser Gly Val Val
305                 310                 315                 320

Leu Ser Ile Thr Ile Pro Val Thr Phe Leu Asp Ala Gly Ala Tyr Lys
                325                 330                 335

Val Val Arg Gln Ala Met Ala Ser Lys Ile Glu Leu Arg Ala Ala Asp
            340                 345                 350

Gly Ser Glu Leu Gly Leu Asp Leu Cys Tyr Thr Ser Glu Ser Leu Ala
        355                 360                 365

Thr Ala Lys Val Pro Ser Met Ala Leu Val Phe Ala Gly Gly Ala Val
    370                 375                 380

Met Glu Leu Glu Met Gly Asn Tyr Phe Tyr Met Asp Ser Thr Thr Gly
385                 390                 395                 400

Leu Glu Cys Leu Thr Ile Leu Pro Ser Pro Ala Gly Asp Gly Ser Leu
                405                 410                 415

Leu Gly Ser Leu Ile Gln Val Gly Thr His Met Ile Tyr Asp Ile Ser
            420                 425                 430

Gly Ser Arg Leu Val Phe Glu Ser Leu Glu Gln Ala Pro Pro Pro
        435                 440                 445

Ser Gly Ser Ser Arg Gln Ser Ser Arg Arg Ser Ser Ser Ala Pro
    450                 455                 460

Pro Pro Leu Thr Ser Pro Ala Val Val Ile His Leu Met Leu Val
465                 470                 475                 480

Val Val Tyr Met Phe Leu
            485

<210> SEQ ID NO 13
<211> LENGTH: 471
<212> TYPE: PRT
<213> ORGANISM: Zea mays

<400> SEQUENCE: 13

Met Ala Met Met Ala Cys Asn Asn Thr Arg Pro Arg Lys Leu Ser Leu
1               5                   10                  15

Pro Cys Arg Thr Arg Thr Phe Gln Ala Leu Ile Leu Ser Thr Ala Val
            20                  25                  30

Phe Leu Ala Ala Ser Thr Ala Val Val Gly Lys Glu Pro Gln Pro
        35                  40                  45

Pro Ser Ser Ser Gly Gly Gly Cys His Tyr Arg Phe Glu Leu Thr His
    50                  55                  60

Val Asp Ala Asn Leu Asn Leu Thr Ser Asp Glu Leu Met Arg Arg Ala
65                  70                  75                  80

Tyr Asp Arg Ser Arg Leu Arg Ala Ala Ser Leu Ala Ala Tyr Ser Asp
                85                  90                  95

Gly Arg His Glu Gly Arg Val Ser Ile Pro Asp Ala Ser Tyr Ile Ile
            100                 105                 110

Thr Phe Tyr Leu Gly Asn Gln Arg Pro Glu Asp Asn Ile Ser Ala Val 115                 120                 125
Val Asp Thr Gly Ser Asp Ile Phe Trp Thr Thr Glu Lys Glu Cys Ser
130                 135                 140
Arg Ser Lys Thr Arg Ser Met Leu Pro Cys Cys Ser Pro Lys Cys Glu
145                 150                 155                 160
Gln Arg Ala Ser Cys Gly Cys Gly Arg Ser Glu Leu Lys Ala Glu Ala
                165                 170                 175
Glu Lys Glu Thr Lys Cys Thr Tyr Ala Ile Ile Tyr Gly Gly Asn Ala
                180                 185                 190
Asn Asp Ser Thr Ala Gly Val Met Tyr Glu Asp Lys Leu Thr Ile Val
                195                 200                 205
Ala Val Ala Ser Lys Ala Val Pro Ser Ser Gln Ser Phe Lys Glu Val
210                 215                 220
Ala Ile Gly Cys Ser Thr Ser Ala Thr Leu Lys Phe Lys Asp Pro Ser
225                 230                 235                 240
Ile Lys Gly Val Phe Gly Leu Gly Arg Ser Ala Thr Ser Leu Pro Arg
                245                 250                 255
Gln Leu Asn Phe Ser Lys Phe Ser Tyr Cys Leu Ser Ser Tyr Gln Glu
                260                 265                 270
Pro Asp Leu Pro Ser Tyr Leu Leu Leu Thr Ala Ala Pro Asp Met Ala
                275                 280                 285
Thr Gly Ala Val Gly Gly Gly Ala Ala Val Ala Thr Ala Leu Gln
290                 295                 300
Pro Asn Ser Asp Tyr Lys Thr Leu Tyr Phe Val His Leu Gln Asn Ile
305                 310                 315                 320
Ser Ile Gly Gly Thr Arg Phe Pro Ala Val Ser Thr Lys Ser Gly Gly
                325                 330                 335
Asn Met Phe Val Asp Thr Gly Ala Ser Phe Thr Arg Leu Glu Gly Thr
                340                 345                 350
Val Phe Ala Lys Leu Val Thr Glu Leu Asp Arg Ile Met Lys Glu Arg
                355                 360                 365
Lys Tyr Val Lys Glu Gln Pro Gly Arg Asn Asn Gly Gln Ile Cys Tyr
                370                 375                 380
Ser Pro Pro Ser Thr Ala Ala Asp Glu Ser Ser Lys Leu Pro Asp Met
385                 390                 395                 400
Val Leu His Phe Ala Asp Ser Ala Asn Met Val Leu Pro Trp Asp Ser
                405                 410                 415
Tyr Leu Trp Lys Thr Thr Ser Lys Leu Cys Leu Ala Ile Tyr Lys Ser
                420                 425                 430
Asn Ile Lys Gly Gly Ile Ser Val Leu Gly Asn Phe Gln Met Gln Asn
                435                 440                 445
Thr His Met Leu Leu Asp Thr Gly Asn Glu Lys Leu Ser Phe Val Arg
                450                 455                 460
Ala Asp Cys Ser Lys Val Ile
465                 470

<210> SEQ ID NO 14
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atggcctcac cactatactc tgtggtactt ggcttagcaa tagtttctgc cattgttgca      60
ccaacaagct ccacctcaag aggaacccct cttcatcatg gtcagaaaag gccacaaccc     120
ggccttcgtg ttgatctcga gcaggtcgat tcgggcaaga atttgaccaa atacgagctc     180
atcaaacgtg ctatcaagcg tggggagagg aggatgcgaa gcattaatgc tatgttgcag     240
agctcctccg gtattgaaac tcctgtttat gcgggagacg tgaatatct  aatgaacgta     300
gcaattggta ctccggatag ttcttttctcg gccattatgg ataccggcag tgatctcatt    360
tggacgcaat gcgagccatg tacgcagtgc ttcagtcaac ctacgcccat tttcaaccca    420
caggactcgt cttccttctc taccccttcct tgcgagagcc agtattgcca agatcttccg    480
agcgaaacct gcaataataa tgaatgccaa tatacatacg gatacggaga cggttccaca    540
acccaaggtt atatggcaac cgagaccttc actttcgaga cgagctccgt gccgaatatc    600
gcgttcggtt gcggggaaga caaccaggga ttcgggcaag gcaacggggc tggcctgatc    660
gggatgggtt ggggcccgtt atcgcttcct tctcaactcg gcgtgggtca gttctcttac    720
tgcatgacct cctatggaag ctcctcaccc agcactctcg cacttggatc cgcagccagt    780
ggagtgcctg aaggctcccc gagtacgacc ctcatccata gttctttgaa tccaacgtac    840
tattatatta cgctccaagg tataacggtt ggtggcgata atttgggtat tccatcgagt    900
actttttcaac ttcaagacga tggaactggc gggatgataa ttgactccgg acaacgctc    960
acttatcttc cacaagacgc ttacaatgcg gtagcacaag cgttcactga ccagataaat   1020
ctccccaccg tcgatgaatc ctcgagcggc ctcagtacgt gcttccagca accgtccgac   1080
ggatcaaccg tgcaagttcc ggagatttca atgcagtttg atggtggggt gctgaactta   1140
ggggaacaga atatattgat ctctccagct gaagggtgta tatgcttggc gatgggaagt   1200
tcatcgcagc tggaaatttc cattttggg aatatccagc agcaagaaac gcaggtgctc    1260
tatgaccttc agaatttggc cgtgtcgttc gttcctactc agtgtggtgc gtcgtag       1317
```

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Leu Gln Leu Gln Pro Phe Pro Gln Pro Gln Leu Pro Tyr Pro Gln Pro
1               5                   10                  15
Gln Leu Pro Tyr Pro Gln Pro Gln Leu Pro Tyr Pro Gln Pro Gln Pro
            20                  25                  30
Phe

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gly Gln Gln Gln Pro Phe Pro Pro Gln Gln Pro Tyr Pro Gln Pro
1               5                   10                  15
Gln Pro Phe

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Gln Gln Gln Pro Pro Phe Ser Gln Gln Gln Gln Ser Pro Phe Ser
1               5                   10                  15

Gln Gln Gln Gln
            20

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Tyr Tyr Pro Thr Ser Pro Gln Gln
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Gly Gln Gly Gln Gln
1               5

<210> SEQ ID NO 20
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Ser Ser Ser Gly Ile Glu Thr Pro Val Tyr Ala Gly Asp Gly Glu
1               5                   10                  15

Tyr Leu Met Asn Val Ala Ile Gly Thr Pro Asp Ser Ser Phe Ser Ala
            20                  25                  30

Ile Met Asp Thr Gly Ser Asp Leu Ile Trp Thr Gln Cys Glu Pro Cys
        35                  40                  45

Thr Gln Cys Phe Ser Gln Pro Thr Pro Ile Phe Asn Pro Gln Asp Ser
    50                  55                  60

Ser Ser Phe Ser Thr Leu Pro Cys Glu Ser Gln Tyr Cys Gln Asp Leu
65                  70                  75                  80

Pro Ser Glu Thr Cys Asn Asn Asn Glu Cys Gln Tyr Thr Tyr Gly Tyr
                85                  90                  95

Gly Asp Gly Ser Thr Thr Gln Gly Tyr Met Ala Thr Glu Thr Phe Thr
            100                 105                 110

Phe Glu Thr Ser Ser Val Pro Asn Ile Ala Phe Gly Cys Gly Glu Asp
        115                 120                 125

Asn Gln Gly Phe Gly Gln Gly Asn Gly Ala Gly Leu Ile Gly Met Gly
            130                 135                 140

Trp Gly Pro Leu Ser Leu Pro Ser Gln Leu Gly Val Gly Gln Phe Ser
145                 150                 155                 160

Tyr Cys Met Thr Ser Tyr Gly Ser Ser Pro Ser Thr Leu Ala Leu
                165                 170                 175

Gly Ser Ala Ala Ser Gly Val Pro Glu Gly Ser Pro Ser Thr Thr Leu
                180                 185                 190

Ile His Ser Ser Leu Asn Pro Thr Tyr Tyr Ile Thr Leu Gln Gly
                195                 200                 205

Ile Thr Val Gly Gly Asp Asn Leu Gly Ile Pro Ser Ser Thr Phe Gln
                210                 215                 220

Leu Gln Asp Asp Gly Thr Gly Gly Met Ile Ile Asp Ser Gly Thr Thr
225                 230                 235                 240

Leu Thr Tyr Leu Pro Gln Asp Ala Tyr Asn Ala Val Ala Gln Ala Phe
                245                 250                 255

Thr Asp Gln Ile Asn Leu Pro Thr Val Asp Glu Ser Ser Ser Gly Leu
                260                 265                 270

Ser Thr Cys Phe Gln Gln Pro Ser Asp Gly Ser Thr Val Gln Val Pro
                275                 280                 285

Glu Ile Ser Met Gln Phe Asp Gly Gly Val Leu Asn Leu Gly Glu Gln
                290                 295                 300

Asn Ile Leu Ile Ser Pro Ala Glu Gly Val Ile Cys Leu Ala Met Gly
305                 310                 315                 320

Ser Ser Ser Gln Leu Gly Ile Ser Ile Phe Gly Asn Ile Gln Gln Gln
                325                 330                 335

Glu Thr Gln Val Leu Tyr Asp Leu Gln Asn Leu Ala Val Ser Phe Val
                340                 345                 350

Pro Thr Gln Cys Gly Ala Ser
                355

<210> SEQ ID NO 21
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asn Gly Pro Ser Gly Val Glu Thr Ser Val Tyr Ala Gly Asp Gly Glu
1               5                   10                  15

Tyr Leu Met Asn Leu Ser Ile Gly Thr Pro Ala Gln Pro Phe Ser Ala
                20                  25                  30

Ile Met Asp Thr Gly Ser Asp Leu Ile Trp Thr Gln Cys Gln Pro Cys
            35                  40                  45

Thr Gln Cys Phe Asn Gln Ser Thr Pro Ile Phe Asn Pro Gln Gly Ser
        50                  55                  60

Ser Ser Phe Ser Thr Leu Pro Cys Ser Ser Gln Leu Cys Gln Ala Leu
65                  70                  75                  80

Ser Ser Pro Thr Cys Ser Asn Asn Phe Cys Gln Tyr Thr Tyr Gly Tyr
                85                  90                  95

Gly Asp Gly Ser Glu Thr Gln Gly Ser Met Gly Thr Glu Thr Leu Thr
                100                 105                 110

Phe Gly Ser Val Ser Ile Pro Asn Ile Thr Phe Gly Cys Gly Glu Asn

```
            115                 120                 125
Asn Gln Gly Phe Gly Gln Gly Asn Gly Ala Gly Leu Val Gly Met Gly
        130                 135                 140

Arg Gly Pro Leu Ser Leu Pro Ser Gln Leu Asp Val Thr Lys Phe Ser
145                 150                 155                 160

Tyr Cys Met Thr Pro Ile Gly Ser Ser Thr Pro Ser Asn Leu Leu Leu
                165                 170                 175

Gly Ser Leu Ala Asn Ser Val Thr Ala Gly Ser Pro Asn Thr Thr Leu
            180                 185                 190

Ile Gln Ser Ser Gln Ile Pro Thr Phe Tyr Tyr Ile Thr Leu Asn Gly
        195                 200                 205

Leu Ser Val Gly Ser Thr Arg Leu Pro Ile Asp Pro Ser Ala Phe Ala
    210                 215                 220

Leu Asn Ser Asn Asn Gly Thr Gly Gly Ile Ile Asp Ser Gly Thr
225                 230                 235                 240

Thr Leu Thr Tyr Phe Val Asn Asn Ala Tyr Gln Ser Val Arg Gln Glu
                245                 250                 255

Phe Ile Ser Gln Ile Asn Leu Pro Val Val Asn Gly Ser Ser Ser Gly
            260                 265                 270

Phe Asp Leu Cys Phe Gln Thr Pro Ser Asp Pro Ser Asn Leu Gln Ile
        275                 280                 285

Pro Thr Phe Val Met His Phe Asp Gly Gly Asp Leu Glu Leu Pro Ser
    290                 295                 300

Glu Asn Tyr Phe Ile Ser Pro Ser Asn Gly Leu Ile Cys Leu Ala Met
305                 310                 315                 320

Gly Ser Ser Ser Gln Gly Met Ser Ile Phe Gly Asn Ile Gln Gln Gln
                325                 330                 335

Asn Met Leu Val Val Tyr Asp Thr Gly Asn Ser Val Val Ser Phe Ala
            340                 345                 350

Ser Ala Gln Cys Gly Ala Ser
        355

<210> SEQ ID NO 22
<211> LENGTH: 319
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Pro Gln Asn
                20                  25                  30

Pro Ser Gln Gln Gln Pro Gln Glu Gln Val Pro Leu Val Gln Gln Gln
            35                  40                  45

Gln Phe Pro Gly Gln Gln Gln Phe Pro Pro Gln Pro Tyr Pro
        50                  55                  60

Gln Pro Gln Pro Phe Pro Ser Gln Gln Pro Tyr Leu Gln Leu Gln Pro
65                  70                  75                  80

Phe Pro Gln Pro Gln Pro Phe Pro Pro Gln Leu Pro Tyr Pro Gln Pro
                85                  90                  95

Gln Ser Phe Pro Pro Gln Gln Pro Tyr Pro Gln Gln Pro Gln Tyr
            100                 105                 110
```

```
Leu Gln Pro Gln Gln Pro Ile Ser Gln Gln Ala Gln Gln Gln
            115                 120                 125

Gln Gln Gln Gln Gln Gln Gln Gln Gln Ile Leu Gln Gln Ile
        130                 135                 140

Leu Gln Gln Gln Leu Ile Pro Cys Arg Asp Val Val Leu Gln Gln His
145                 150                 155                 160

Asn Ile Ala His Ala Ser Ser Gln Val Leu Gln Gln Ser Thr Tyr Gln
                165                 170                 175

Leu Leu Gln Gln Leu Cys Cys Gln Gln Leu Leu Gln Ile Pro Glu Gln
            180                 185                 190

Ser Gln Cys Gln Ala Ile His Asn Val Ala His Ala Ile Ile Met His
            195                 200                 205

Gln Gln Gln Gln Gln Gln Glu Gln Lys Gln Gln Leu Gln Gln Gln
        210                 215                 220

Gln Gln Gln Gln Gln Gln Leu Gln Gln Gln Gln Gln Gln Gln Gln
225                 230                 235                 240

Gln Pro Ser Ser Gln Val Ser Phe Gln Gln Pro Gln Gln Tyr Pro
                245                 250                 255

Ser Ser Gln Val Ser Phe Gln Pro Ser Gln Leu Asn Pro Gln Ala Gln
            260                 265                 270

Gly Ser Val Gln Pro Gln Gln Leu Pro Gln Phe Ala Glu Ile Arg Asn
            275                 280                 285

Leu Ala Leu Gln Thr Leu Pro Ala Met Cys Asn Val Tyr Ile Pro Pro
            290                 295                 300

His Cys Ser Thr Thr Ile Ala Pro Phe Gly Ile Ser Gly Thr Asn
305                 310                 315

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Val Arg Val Pro Val Pro Gln
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Val Arg Val Pro Val Pro Gln
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Val Arg Val Pro Val Pro Gln Leu
```

```
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Val Arg Val Pro Val Pro Gln Leu
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Val Arg Val Pro Val Pro Gln Leu Gln
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Val Arg Val Pro Val Pro Gln Leu Gln Pro Gln
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Val Arg Val Pro Val Pro Gln Leu Gln Pro Gln
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Val Arg Val Pro Val Pro Gln Leu Gln Pro Gln
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 31

Ala Val Arg Val Pro Val Pro Gln Leu Gln Pro Gln Asn
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Val Arg Val Pro Val Pro Gln Leu Gln Pro Gln Asn Pro Ser
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Val Arg Val Pro Val Pro Gln Leu Gln Pro Gln Asn Pro Ser
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Val Arg Val Pro Val Pro Gln Leu Gln Pro Gln Asn Pro Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Val Arg Val Pro Val Pro Gln Leu Gln Pro Gln Asn Pro Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Val Arg Val Pro Val Pro Gln Leu Gln Pro Gln Asn Pro Ser
1               5                   10                  15

<210> SEQ ID NO 37
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Val Arg Val Pro Val Pro Gln Leu Gln Pro Gln Asn Pro Ser
1               5                   10                  15

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Val Arg Val Pro Val Pro Gln Leu Gln Pro Gln Asn Pro Ser Gln
1               5                   10                  15

Gln Gln Pro Gln
            20

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Val Arg Val Pro Val Pro Gln Leu Gln Pro Gln Asn Pro Ser Gln
1               5                   10                  15

Gln Gln Pro Gln
            20

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Val Arg Val Pro Val Pro Gln Leu Gln Pro Gln Asn Pro Ser Gln
1               5                   10                  15

Gln Gln Pro Gln
            20

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Val Arg Val Pro Val Pro Gln Leu Gln Pro Gln Asn Pro Ser Gln
1               5                   10                  15

Gln Gln Pro Gln
            20
```

```
<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Val Arg Val Pro Val Pro Gln Leu Gln Pro Gln Asn Pro Ser Gln
1               5                   10                  15

Gln Gln Pro Gln
            20

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Val Arg Val Pro Val Pro Gln Leu Gln Pro Gln Asn Pro Ser Gln
1               5                   10                  15

Gln Gln Pro Gln
            20

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Val Arg Val Pro Val Pro Gln Leu Gln Pro Gln Asn Pro Ser Gln
1               5                   10                  15

Gln Gln Pro Gln
            20

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Gln Leu Gln Pro Gln Asn Pro Ser
1               5

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Pro Gln Leu Gln Pro Gln Asn Pro Ser Gln Gln Gln Pro Gln
1               5                   10
```

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Gln Pro Gln Asn Pro Ser Gln Gln Gln Pro Gln
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Gln Pro Gln Asn Pro Ser Gln Gln Gln Pro Gln
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Gln Pro Gln Asn Pro Ser Gln Gln Gln Pro Gln
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Gln Pro Gln Asn Pro Ser Gln Gln Gln Pro Gln
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Pro Gln Asn Pro Ser Gln Gln Gln Pro Gln
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Gln Asn Pro Ser Gln Gln Gln Pro Gln
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Gln Glu Gln Val Pro Leu
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Gln Glu Gln Val Pro Leu
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Gln Glu Gln Val Pro Leu
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Pro Gln Glu Gln Val Pro Leu
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Pro Gln Glu Gln Val Pro Leu Val
1               5

<210> SEQ ID NO 58
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Val Pro Leu Val Gln Gln Gln Gln
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Leu Val Gln Gln Gln Gln Phe Pro
1               5

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Pro Leu Val Gln Gln Gln Gln Phe Pro Gly
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Leu Val Gln Gln Gln Gln Phe Pro Gly
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Leu Val Gln Gln Gln Gln Phe Pro Gly
1               5                   10

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Pro Leu Val Gln Gln Gln Gln Phe Pro Gly Gln Gln Gln Gln Phe Pro
```

```
1               5                   10                  15
Pro Gln

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro Leu Val Gln Gln Gln Gln Phe Pro Gly Gln Gln Gln Gln Phe Pro
1               5                   10                  15

Pro Gln

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Val Gln Gln Gln Gln Phe Pro Gly
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Gln Gln Gln Gln Phe Pro Gly
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Gln Gln Gln Gln Phe Pro Gly
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Gln Gln Phe Pro Gly
1               5

<210> SEQ ID NO 69
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Gln Gln Phe Pro Gly
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Gln Gln Phe Pro Gly
1               5

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gln Phe Pro Gly Gln Gln Gln Gln Phe Pro Pro Gln
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Gln Gln Gln Phe Pro Pro Gln Gln
1               5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gln Gln Phe Pro Pro Gln Gln Pro Tyr
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Gln Phe Pro Pro Gln Gln Pro Tyr
```

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Gln Gln Phe Pro Pro Gln Gln Pro Tyr
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Pro Gln Gln Pro Tyr Pro Gln
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Pro Gln Gln Pro Tyr Pro Gln
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Pro Gln Gln Pro Tyr Pro Gln Pro
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Pro Gln Gln Pro Tyr Pro Gln Pro Gln
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Pro Gln Gln Pro Tyr Pro Gln Pro Gln
1               5

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Pro Gln Gln Pro Tyr Pro Gln Pro Gln Pro Phe
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Pro Gln Gln Pro Tyr Pro Gln Pro Gln Pro Phe Pro
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Pro Gln Gln Pro Tyr Pro Gln Pro Gln Pro Phe Pro Ser Gln
1               5                   10

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Pro Gln Gln Pro Tyr Pro Gln Pro Gln Pro Phe Pro Ser Gln Gln Pro
1               5                   10                  15

Tyr

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Pro Gln Pro Gln Pro Phe Pro Ser Gln Gln Pro Tyr
1               5                   10

```
<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Pro Gln Pro Phe Pro Ser Gln Gln Pro Tyr
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Pro Gln Pro Phe Pro Ser Gln Gln Pro Tyr
1               5                   10

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Gln Gln Pro Tyr Leu Gln Leu Gln Pro Phe Pro Gln Pro Gln
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Gln Gln Pro Tyr Leu Gln Leu Gln Pro Phe Pro Gln Pro Gln
1               5                   10                  15

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Gln Pro Tyr Leu Gln Leu Gln Pro Phe Pro Gln Pro Gln
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 91

Pro Tyr Leu Gln Leu Gln Pro Phe Pro Gln Pro Gln
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Pro Tyr Leu Gln Leu Gln Pro Phe Pro Gln Pro Gln
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Tyr Leu Gln Leu Gln Pro Phe Pro Gln Pro Gln
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Leu Gln Pro Phe Pro Gln Pro Gln
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Leu Gln Pro Phe Pro Gln Pro Gln
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Gln Pro Phe Pro Gln Pro Gln
1               5

<210> SEQ ID NO 97
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 97

Leu Gln Pro Phe Pro Gln Pro Gln Phe Pro Pro Gln
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Gln Pro Phe Pro Gln Pro Gln Phe Pro Pro Gln
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Pro Phe Pro Gln Pro Gln Pro Phe Pro Pro Gln Leu Pro Tyr
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Pro Gln Leu Pro Tyr Pro Gln Pro Gln
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Pro Gln Leu Pro Tyr Pro Gln Pro Gln
1               5

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Pro Gln Leu Pro Tyr Pro Gln Pro Gln Ser Phe Pro Pro Gln
1               5                   10
```

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Pro Gln Gln Pro Tyr Pro Gln Gln Gln
1               5

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Pro Gln Gln Pro Tyr Pro Gln Gln Gln Pro Gln
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Pro Gln Gln Pro Tyr Pro Gln Gln Gln Pro Gln
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Gln Pro Tyr Pro Gln Gln Gln Pro Gln
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Gln Pro Tyr Pro Gln Gln Gln Pro Gln
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 108

Pro Gln Tyr Leu Gln Pro Gln
1               5

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Pro Gln Gln Pro Ile Ser Gln Gln Gln Ala
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Pro Gln Gln Pro Ile Ser Gln Gln Gln Ala
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Pro Gln Gln Pro Ile Ser Gln Gln Gln Ala Gln
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Pro Gln Gln Pro Ile Ser Gln Gln Gln Ala Gln
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Pro Gln Gln Pro Ile Ser Gln Gln Gln Ala Gln Gln Gln Gln
1               5                   10

<210> SEQ ID NO 114
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Pro Gln Gln Pro Ile Ser Gln Gln Gln Ala Gln Gln Gln Gln Gln
1               5                   10                  15

Gln Gln Gln Gln Gln Gln Gln Gln Gln
            20                  25

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Gln Gln Ile Leu Gln Gln Ile Leu Gln Gln
1               5                   10

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Gln Ile Leu Gln Gln Ile Leu Gln
1               5

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Gln Gln Gln Leu Gln Gln Gln Gln
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Gln Gln Gln Gln Gln Gln Gln Gln Gln Gln Pro Ser
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 119

Leu Gln Gln Gln Gln Gln Gln Gln Gln Gln Pro Ser Ser
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Gln Gln Gln Gln Gln Gln Gln Gln Gln Pro Ser
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Ser Gln Val Ser Phe Gln Gln Pro Gln
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Ser Gln Val Ser Phe Gln Gln Pro Gln
1               5                   10

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Phe Gln Gln Pro Gln Gln Gln Tyr
1               5

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Pro Gln Gln Gln Tyr Pro Ser Ser Gln Val
1               5                   10

<210> SEQ ID NO 125
<211> LENGTH: 10
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 125

Pro Gln Gln Gln Tyr Pro Ser Ser Gln Val
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Pro Gln Gln Gln Tyr Pro Ser Ser Gln Val
1               5                   10

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Pro Gln Gln Gln Tyr Pro Ser Ser Gln Val Ser Phe Gln Pro Ser
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Pro Gln Gln Gln Tyr Pro Ser Ser Gln Val Ser Phe Gln Pro Ser Gln
1               5                   10                  15

<210> SEQ ID NO 129
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Pro Gln Gln Gln Tyr Pro Ser Ser Gln Val Ser Phe Gln Pro Ser Gln
1               5                   10                  15

Leu Asn Pro Gln
            20

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

-continued

Gln Val Ser Phe Gln Pro Ser Gln Leu Asn Pro Gln
1               5                   10

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Phe Gln Pro Ser Gln Leu Asn Pro Gln Ala Gln Gly Ser Val Gln Pro
1               5                   10                  15

Gln

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Pro Ser Gln Leu Asn Pro Gln Ala Gln Gly Ser Val Gln Pro Gln
1               5                   10                  15

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Gln Leu Asn Pro Gln Ala Gln Gly Ser Val Gln Pro Gln
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Leu Asn Pro Gln Ala Gln Gly Ser Val Gln Pro Gln
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asn Pro Gln Ala Gln Gly Ser Val Gln Pro Gln
1               5                   10

<210> SEQ ID NO 136
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Pro Gln Ala Gln Gly Ser Val Gln Pro Gln
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Pro Gln Ala Gln Gly Ser Val Gln Pro Gln
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Pro Gln Ala Gln Gly Ser Val Gln Pro Gln
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Pro Gln Ala Gln Gly Ser Val Gln Pro Gln
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Pro Gln Ala Gln Gly Ser Val Gln Pro Gln
1               5                   10

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Pro Gln Gln Leu Pro Gln Phe
```

```
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Pro Gln Gln Leu Pro Gln Phe Ala
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Pro Gln Phe Ala Glu Ile Arg Asn
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Pro Gln Phe Ala Glu Ile Arg Asn Leu
1               5

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Pro Gln Phe Ala Glu Ile Arg Asn Leu Ala
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Pro Gln Phe Ala Glu Ile Arg Asn Leu Ala
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 147

Glu Ile Arg Asn Leu Ala Leu Gln Thr Leu Pro
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Asn Leu Ala Leu Gln Thr Leu Pro Ala
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Asn Leu Ala Leu Gln Thr Leu Pro Ala
1               5                   10

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Leu Ala Leu Gln Thr Leu Pro Ala
1               5
```

COMPOSITIONS AND METHODS FOR TREATING GLUTEN INTOLERANCE AND DISORDERS ARISING THEREFROM

CROSS-REFERENCE TO RELATED APPLICATIONS

This application claims priority to U.S. patent application Ser. No. 14/741,396, which claims priority to U.S. Provisional Application Nos. 62/012,865, filed Jun. 16, 2014, and 62/118,396, filed Feb. 19, 2015. The content of each prior application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 24, 2015, is named 107572-0251 SL.txt and is 87,775 bytes in size.

FIELD OF THE INVENTION

Provided herein are compositions and methods for the treatment of gluten intolerance and related conditions, such as celiac disease or gluten sensitivity. Further provided herein are compositions and methods for attenuating or preventing intraepithelial lymphocyte (IEL) infiltration induced by the presence of food protein antigens in the intestine. Such food protein antigens include difficult to digest proline rich foods such as proteins found in wheat, barley, rye, etc. that contain gluten. Gluten, in particular, is partially hydrolyzed in the gastrointestinal tract and can lead to IEL infiltration and production of antibodies including endomysial IgA and anti-tissue transglutaminase. The compositions and methods of this invention provide for reduced amounts of such food protein antigens in the intestine which, in turn, reduces the amount of IEL infiltration of the intestine.

BACKGROUND OF THE INVENTION

Several diseases are mediated by reactions to antigenic food proteins in susceptible individuals. For example, ingestion of wheat, barley, and rye, which contain antigenic food proteins (e.g., gluten) may cause abnormal autoimmune responses, such as celiac disease, wheat allergy and dermatitis herpetiformis, in gluten intolerant individuals. Gluten is a mixture of glutamine- and proline-rich glutenin and prolamin protein molecules.

Celiac disease is an autoimmune disorder affecting the small intestine. Most of the individuals having the abnormal autoimmune responses characteristic of celiac disease express the human leukocyte antigen (HLA) DQ2 or DQ8 molecules. Symptoms of the disease are caused by a reaction to gluten proteins, and may also include other storage proteins in the grain products consumed (e.g. serpins, purinins). Clinically, the disease is detectable in part through the quantitation of antibodies specific for gluten and tissue transglutaminase (tTG). The autoimmune responses result in the development of small intestinal mucosal villous atrophy with crypt hyperplasia and mucosal inflammation. Symptoms of celiac disease can vary from individual to individual, and may include one or more of fatigue, chronic diarrhea, constipation, malabsorption of nutrients, weight loss, abdominal distension, anemia, as well as a substantially enhanced risk for the development of osteoporosis and intestinal malignancies (lymphoma and carcinoma).

Type I diabetes is a risk factor for celiac disease. Autism is also associated with celiac disease, and a gluten-free diet may help alleviate some symptoms of autism. Similarly, it is believed that some people with attention deficit hyperactivity disorder exhibit fewer symptoms when gluten is removed from their diets. Other conditions that may benefit from elimination of dietary gluten include rheumatoid arthritis and fibromyalgia.

Treatment for gluten intolerance, especially celiac disease, commonly involves a lifelong, strict gluten-free diet. However, gluten-free diet is inconvenient, restrictive, and gluten is difficult to avoid. Therefore, effective alternative treatments of gluten intolerance and celiac disease are needed.

SUMMARY OF THE INVENTION

This invention relates to the discovery that administration of a pharmaceutical composition comprising one or more *Nepenthes* enzymes as described herein, in combination with a potentially antigenic food protein, results in a decrease in immune response to the antigenic food protein after ingestion, including a decrease in infiltration and/or production of intraepithelial lymphocytes in the intestine. Intraepithelial lymphocytes are T cells that are interspersed between epithelial cells of the large and small intestine. An increased T cell count is an early indicator of inflammation and is potentially associated with gluten intolerance, including celiac disease.

The toxic properties of gluten proteins (e.g., gliadins and glutenins) are believed to be largely due to proline- and glutamine-rich peptides that are produced during incomplete degradation of the proteins by human digestive enzymes (including pepsin). Gastric and pancreatic endoproteases are unable to cleave these toxic or immunogenic peptide byproducts of incomplete degradation, at least in part due to the fact that such enzymes lack specificity for proline and/or glutamine. The peptides are believed to cause numerous intestinal symptoms in sensitive individuals, including intraepithelial lymphocytosis, villous atrophy, and/or inflammation. Other proteins present in wheat may also be implicated in the autoimmune response, including serpins, purinins, alpha-amylase/protease inhibitors, globulins, and farinins.

T cells are a first responder to antigenic insult (i.e., presence of toxic food peptides) in a sensitive individual. T cells react quickly to antigen insult and cause inflammation and, in some cases, degradation of the intestine. A reduction in T cells in the intestine thus indicates a decreased immune response, and is a potential indicator of reduced or eliminated symptoms associated with immunogenic food (e.g., gluten) consumption in sensitive individuals.

Without being bound by theory, it is believed that contacting gluten (or other antigenic protein) with a pharmaceutical composition as described herein breaks down the protein into small polypeptide fragments that reduces or eliminates an immune response (i.e., are not toxic or are less toxic).

It is contemplated that a pharmaceutical composition as described herein can be used to degrade dietary proteins, particularly proline- and/or glutamine-rich proteins, that are not effectively degraded by digestive tract enzymes. It is further contemplated that such degradation would increase absorption of the proteins and/or decrease immunogenicity. Such a result may have beneficial effects on the symptoms of intestinal diseases and disorders (e.g., celiac disease, gluten intolerance, irritable bowel syndrome, colitis, Crohn's disease, food allergies and the like). In one embodiment, administration of the pharmaceutical composition improves nutrient absorption.

The pitcher secretions of *Nepenthes*, a carnivorous pitcher plant commonly known as monkey cups in tropical regions, include a number of proteases. Concentrated *Nepenthes* pitcher fluid has high specificity for proline- and glutamine-rich gluten peptides. U.S. Patent Application Publication Nos. 2014/0186330 and 2014/0140980, incorporated herein by reference in their entireties, describe the activity and specificity of concentrated *Nepenthes* pitcher fluid and recombinant *Nepenthes* enzymes. The pitcher fluid is acidic, and the enzymes therein are generally most active at acidic pH.

Nepenthesin (EC 3.4.23.12) is an aspartic protease that can be isolated or concentrated from *Nepenthes* pitcher secretions, as well as a variety of other plant sources. Tökés et al., Digestive Enzymes Secreted by the Carnivorous Plant *Nepenthes* macferlanei L., Planta (Berl.) 119, 39-46 (1974). It has been found that the activity of nepenthesin is higher than that of pepsin (EC 3.4.23.1), an enzyme present in the stomach of humans that is partly responsible for degrading food proteins into peptides. Nepenthesin has two known isotypes: nepenthesin I (known to have two variants: nepenthesin Ia and nepenthesin Ib) and nepenthesin II.

In one aspect, this invention relates to the discovery of a novel prolyl endopeptidase, neprosin, which possesses a high proteolytic activity for cleaving proline-rich proteins and oligopeptides (such as gluten proteins). Neprosin can be isolated or concentrated from the pitcher secretions of *Nepenthes*, is active at a broad pH range, and is especially active at low pH (e.g., about 3 to 5). The neprosin protein sequence is not homologous to any other known protein in the genomic databases. Neprosin can efficiently cleave peptides on the carboxy (C)-terminal side of proline. This cleavage appears to be highly specific.

Neprosin, nepenthesin I, and nepenthesin II, alone or in combination, are able to cleave toxic food peptides into smaller, non-toxic peptides. Because the enzymes are active at a broad acidic pH range, digestion by the enzymes can initiate in the acidic environment of the stomach.

This invention is further based on the discovery that such enzyme compositions are capable of degrading food protein antigens to a level where the immune response in the intestine, as measured by IEL infiltration, is attenuated or eliminated when used in combination with food. IEL infiltration due to the presence of peptidic food antigen(s) is an early biological indicator of sensitivity to food antigen (e.g., gluten). Accordingly, in one aspect, this invention is directed to a method for attenuating or preventing an immune response to food protein antigens in the intestine of a mammal, which method comprises administering to the mammal an effective amount of a pharmaceutical composition comprising at least one *Nepenthes* enzyme. In one embodiment, the at least one *Nepenthes* enzyme is nepenthesin I, nepenthesin II, neprosin, a variant thereof, or a mixture thereof. In one embodiment, the amount of the pharmaceutical composition is effective to attenuate or prevent IEL infiltration of the intestine due to the presence of the peptidic food antigen(s). In one embodiment, the IEL infiltration is due to incomplete digestion of a potentially antigenic food protein by endogenous gastric and/or intestinal enzymes. In one embodiment, the composition is administered to the mammal prior to ingestion of a potentially antigenic food or protein. In one embodiment, the composition is administered to the mammal with ingestion of a potentially antigenic food or protein. In one embodiment, the composition is administered to the mammal after ingestion of a potentially antigenic food or protein. In one embodiment, the composition is administered to the mammal irrespective of consumption of a potentially antigenic food or protein. In one embodiment, the potentially antigenic protein is gluten. In one embodiment, the potentially antigenic protein is one or more wheat proteins.

In one embodiment, intestinal inflammation is characterized by infiltration and/or proliferation of IELs in the intestine. Accordingly, in one aspect, this invention is directed to a method for attenuating or preventing intestinal inflammation due to the presence of peptidic food antigen(s) in the intestine of a mammal, which method comprises administering to the mammal an effective amount of a pharmaceutical composition comprising at least one *Nepenthes* enzyme. In one embodiment, the at least one *Nepenthes* enzyme is nepenthesin I, nepenthesin II, neprosin, a variant thereof, or a mixture thereof. In one embodiment, the amount of the pharmaceutical composition is effective to attenuate or prevent intestinal inflammation due to the presence of the peptidic food antigen(s). In one embodiment, the intestinal inflammation is due to incomplete digestion of a potentially antigenic food protein by endogenous gastric and/or intestinal enzymes. In one embodiment, the composition is administered to the mammal prior to ingestion of a potentially antigenic food or protein. In one embodiment, the composition is administered to the mammal with ingestion of a potentially antigenic food or protein. In one embodiment, the composition is administered to the mammal after ingestion of a potentially antigenic food or protein. In one embodiment, the composition is administered to the mammal irrespective of consumption of a potentially antigenic food or protein. In one embodiment, the potentially antigenic protein is gluten. In one embodiment, the potentially antigenic protein is one or more wheat proteins.

In one aspect, this invention is directed to a method for attenuating or preventing intraepithelial lymphocytosis due to the presence of peptidic food antigen(s) in an intestine of a mammal, which method comprises administering to the mammal an effective amount of a pharmaceutical composition comprising at least one *Nepenthes* enzyme. In one embodiment, the at least one *Nepenthes* enzyme is nepenthesin I, nepenthesin II, neprosin, a variant thereof, or a mixture thereof. In one embodiment, the amount of the pharmaceutical composition is effective to inhibit intraepithelial lymphocytosis in the intestine. In one embodiment, the composition is administered to the mammal prior to ingestion of a potentially antigenic food or protein. In one embodiment, the composition is administered to the mammal with ingestion of a potentially antigenic food or protein. In one embodiment, the composition is administered to the mammal after ingestion of a potentially antigenic food. In one embodiment, the composition is administered to the mammal irrespective of consumption of a potentially antigenic food or protein. In one embodiment, the potentially antigenic protein is gluten. In one embodiment, the potentially antigenic protein is one or more wheat proteins.

In one embodiment, the effective amount of the pharmaceutical composition is between about 1 mg and about 1 g. In one embodiment, the effective amount of the pharmaceutical composition depends on the amount of potentially antigenic protein consumed.

In one embodiment, this invention is directed to treating and/or ameliorating at least one symptom associated with an immune response to the presence of gluten or other antigenic protein in the intestine of a patient. Symptoms include, without limitation, "foggy mind", depression, anxiety, ADHD-like behavior, abdominal pain, bloating, diarrhea, constipation, headaches, migraines, bone or joint pain, chronic fatigue, small intestine damage, development of tissue transglutaminase (tTG) antibodies, severe acne, vomiting, weight loss, irritability, iron-deficiency anemia, arthritis, tingling numbness in the extremities, infertility, and canker sores of the mouth.

In one aspect, this invention is directed to a method for attenuating or preventing villous atrophy due to the presence of peptidic food antigen(s) in an intestine of a mammal, which method comprises administering to the mammal an effective amount of a pharmaceutical composition comprising at least one *Nepenthes* enzyme. In one embodiment, the at least one *Nepenthes* enzyme is nepenthesin I, nepenthesin II, neprosin, a variant thereof, or a mixture thereof. In one embodiment, the potentially antigenic protein is degraded by the pharmaceutical composition so as to inhibit villous atrophy in the intestine. In one embodiment, the potentially antigenic protein is gluten. In one embodiment, the potentially antigenic protein is one or more wheat proteins.

In one aspect, this invention is directed to a method for reducing T cell response to a peptidic food antigen, the method comprising contacting the peptidic food antigen with an effective amount of a pharmaceutical composition comprising at least one *Nepenthes* enzyme. In one embodiment, the at least one *Nepenthes* enzyme is nepenthesin I, nepenthesin II, neprosin, a variant thereof, or a mixture thereof, under conditions wherein said antigen is degraded so as to reduce T cell response to the antigen. In one embodiment, T cell response in an intestine of a mammal is reduced. In one embodiment, the antigen is contacted with the pharmaceutical composition in the stomach of a mammal. In one embodiment, the antigen is contacted with the pharmaceutical composition ex vivo. In one embodiment, the antigen is gluten. In one embodiment, the antigen is an immunotoxic gluten protein.

In one aspect, this invention is directed to a method for attenuating or preventing a manifestation of celiac disease arising from the presence of partially hydrolyzed wheat protein in an intestine of a patient having celiac disease, comprising administering to the patient an effective amount of a pharmaceutical composition comprising at least one *Nepenthes* enzyme. In one embodiment, the at least one *Nepenthes* enzyme is nepenthesin I, nepenthesin II, neprosin, variant thereof, or a mixture thereof, so as to attenuate or prevent a manifestation of celiac disease.

In one aspect, this invention is directed to a method for improving digestibility of a protein from a food in a mammal with an intestinal disorder, which method comprises administering to the mammal an effective amount of a pharmaceutical composition comprising at least one *Nepenthes* enzyme. In one embodiment, the at least one *Nepenthes* enzyme is nepenthesin I, nepenthesin II, neprosin, variant thereof, or a mixture thereof, under conditions wherein the protein in the food is degraded by the pharmaceutical composition. In one embodiment, degradation of the protein improves absorption of the protein in the intestine. In one embodiment, at least one symptom of the disorder is attenuated or prevented. In one embodiment, the intestinal disorder is Crohn's disease, irritable bowel syndrome, or colitis. In one embodiment, protein absorption from the food is increased.

In one aspect, this invention is directed to a method for treating insufficiency of pancreatic enzymes in a patient in need thereof, comprising administering to the patient an effective amount of a pharmaceutical composition comprising at least one *Nepenthes* enzyme. In one embodiment, the at least one *Nepenthes* enzyme is nepenthesin I, nepenthesin II, neprosin, variant thereof, and a mixture thereof. In one embodiment, one or more pancreatic enzymes in administered. The one or more pancreatic enzymes may be administered concurrently with the pharmaceutical composition, or at a different time. In one embodiment, the pancreatic enzyme is a lipase, an amylase, a protease, or a mixture thereof. In one embodiment, the insufficiency of pancreatic enzymes is due to pancreatitis, cystic fibrosis, Shwachman-Bodian-Diamond syndrome, gallstones, lupus, celiac sprue, pancreatic cancer, or pancreatic surgery. In one embodiment, the pancreatitis is chronic pancreatitis.

In one embodiment, the *Nepenthes* enzyme is concentrated, isolated, or extracted from the pitcher fluid of a *Nepenthes* plant. In one embodiment, the *Nepenthes* enzyme comprises recombinant nepenthesin I, recombinant nepenthesin II, recombinant neprosin, a variant thereof, or a mixture thereof.

In one embodiment, the variant thereof comprises a protein, the amino acid sequence of which has at least 85% sequence homology to the amino acid sequence selected from the group consisting of SEQ ID NO.:1, SEQ ID NO.: 5, SEQ ID NO.: 6, SEQ ID NO.: 7, SEQ ID NO.: 8, SEQ ID NO.: 9, SEQ ID NO.: 20, and SEQ ID NO.: 21. In one embodiment, the variant thereof comprises a protein, the amino acid sequence of which has at least 85% sequence homology to the amino acid encoded by the cDNA selected from the group consisting of SEQ ID NO.:2, SEQ ID NO.:4, and SEQ ID NO.:14.

In one embodiment, the food is a liquid. In one aspect, the food is a solid. In a preferred embodiment, the pharmaceutical composition is orally administered.

Even when a patient adheres to a strict gluten-free diet, gluten is hard to avoid. Numerous foods, particularly processed foods, are contaminated with small amounts of gluten. Consumption of even minute amounts of gluten can lead to a recurrence of symptoms in a patient with celiac disease. Such is also true of other potentially immunogenic foods.

In one embodiment, the pharmaceutical composition is administered irrespective of whether the patient has ingested (e.g., knowingly ingested) a food containing a potentially immunogenic protein. In one embodiment, the pharmaceutical composition is administered on an as-needed basis, e.g., before, during, and/or after a meal that might be contaminated by a potentially immunogenic protein, or in which the potentially immunogenic protein content is unknown. In one embodiment, the pharmaceutical composition is administered on a regular basis. In one embodiment, the pharmaceutical composition is administered at least one time per day. In one embodiment, the pharmaceutical composition is administered two, three, four, or more times per day. In one embodiment, the pharmaceutical composition is administered in conjunction with (e.g., before, during, or after) each meal and/or snack. In one embodiment, the pharmaceutical composition is included as part of a sustained release formulation where there is a continuous release of enzyme(s) to allow for intermittent snacking, etc. without regard to the antigenic protein content of the food.

In one embodiment, the pharmaceutical composition is maintained in an aqueous system at about pH 2 wherein the free amino groups of said enzyme are charged. In one embodiment, the composition is maintained at neutral pH prior to contact with acids in the stomach. In one embodiment, the pharmaceutical composition comprises a pharmaceutically acceptable buffer, such that the pH of the composition remains at pH 5 or 6 upon contact with acids in the stomach.

In one embodiment, the effective amount of pharmaceutical composition is between about 1 mg and about 1 g. In one embodiment, the effective amount of pharmaceutical composition is between about 1 mg and about 1 g per 1 g substrate (e.g., gluten or other potentially immunogenic protein). In one embodiment, the pharmaceutical composition comprises more than one of nepenthesin I, nepenthesin II, neprosin, or a variant thereof.

In one embodiment, the mammal is a human. In one aspect, the human suffers from gluten sensitivity or celiac disease. In one aspect, it is contemplated that intestinal antigen protein sensitivity correlates, directly or indirectly, with attention deficit hyperactivity disorder, autism, rheumatoid arthritis, fibromyalgia, and/or dermatitis herpetiformis. It is further contemplated that removing such antigenic intestinal proteins from the intestine using compositions of this invention will have a positive effect on attention deficit hyperactivity disorder, autism, rheumatoid arthritis, fibromyalgia, and/or dermatitis herpetiformis. In a preferred embodiment, the human suffers from celiac disease.

In one aspect, this invention is directed to a pharmaceutical composition comprising nepenthesin I, nepenthesin II, neprosin, variant thereof, or a mixture thereof. In a preferred embodiment, the pharmaceutical composition comprises neprosin or a variant and/or salt thereof. In a further preferred embodiment, the pharmaceutical composition further comprises at least one additional *Nepenthes* enzyme. In one embodiment, the additional *Nepenthes* enzyme comprises nepenthesin I, nepenthesin II, a variant thereof, and/or a salt thereof.

Without being bound by theory, it is believed that nepenthesin I, nepenthesin II, and neprosin are less active or substantially inactive at neutral to basic pH. This can be important where there is a potential for undesirable digestion by the enzyme(s). For example, where the pharmaceutical composition is administered orally, buffering of the composition to pH 6.5 or greater may result in a less active form of the enzyme(s) such that the oral mucosa, esophageal mucosa, and other cells that may come into contact with the composition will not be digested by the enzyme(s) therein. Likewise, when the composition is added to a food, the buffered enzyme(s) will be unable to (or less able to) digest the food before it is consumed. In such situations, introduction of the composition to the acidic environment of the stomach will result in a decrease in the pH and activation of enzyme(s).

In one embodiment, the pharmaceutical composition is buffered to about pH 6.5 or higher. In a preferred embodiment, the composition is buffered to about pH 6.5 to about pH 8.5. In one embodiment, the composition is in liquid form. In one embodiment, the composition is in solid form. In one embodiment, the pH of the composition is adjusted in liquid form and the composition is dried to form a solid.

In one embodiment, the pharmaceutical composition comprises one or more additional proteases. In one embodiment, the one or more additional protease is an aspartic protease, a serine protease, a threonine protease, a cysteine protease, a glutamic acid protease, or a metalloprotease. In one embodiment, the pharmaceutical composition comprises one or more additional exoproteases, such as, leucine aminopeptidases and carboxypeptidases. In one embodiment, the one or more additional protease is trypsin. In a preferred embodiment, the one or more additional protease is active at acidic pH (e.g., pH 2-6).

In one aspect, the invention is directed to a formulation comprising the pharmaceutical composition of the invention, wherein the enzyme(s) is present in a delayed release vehicle such that the enzyme(s) is released continuously while the formulation is present in the stomach. In one embodiment, the formulation has a pH of greater than about 5 prior to contact with acids in the stomach. In one embodiment, the formulation comprises a biologically acceptable buffer, such that the pH of the composition remains at about pH 5 or 6 for at least a period of time upon contact with acids in the stomach.

In one embodiment, the invention is directed to a unit dose formulation of the pharmaceutical composition. For example and without limitation, the unit dose may be present in a tablet, a capsule, and the like. The unit dose may be in solid, liquid, powder, or any other form. Without being bound by theory, it is envisioned that a unit dose formulation of the pharmaceutical composition will allow for proper dosing (e.g., based on the amount of immunogenic protein ingested) while avoiding potential negative side effects of administering an excessive amount of the composition.

In one embodiment, the invention is directed to a proenzyme form of the nepenthesin I, nepenthesin II, neprosin, and/or variant thereof. In one embodiment, a propeptide is present on the enzyme. In a preferred embodiment, the propeptide is removed by acidic pH, thereby activating the enzyme. In one embodiment, the propeptide comprises the naturally-occurring propeptide amino acid sequence for the enzyme. In one embodiment, the propeptide is an artificial propeptide or a meterologous propeptide (i.e., an acid-labile propeptide from a different protein and/or species).

BRIEF DESCRIPTION OF THE DRAWINGS

FIG. 1 shows an alignment of the protein sequences for nepenthesin I from *Nepenthes mirabilis* (SEQ ID NO.: 5), *Nepenthes alata* (SEQ ID NO.: 6), *Nepenthes gracilis* (SEQ ID NO.: 7), *Zea mays* (SEQ ID NO.: 10), and *Oryza sativa* (SEQ ID NO.: 11), and nepenthesin II from *Nepenthes mirabilis* (SEQ ID NO.: 8), *Nepenthes gracilis* (SEQ ID NO.: 9), *Oryza sativa* (SEQ ID NO.: 12), and *Zea mays* (SEQ ID NO.: 13).

FIG. 9 shows cleavage preferences at (A) the P1 or N-terminal side of the cleavage site and at (B) the P1' or C-terminal side of the cleavage site for the indicated enzymes. Left bars for each residue indicate digestion with Nepenthes extract, the middle bars indicate digestion with purified Nepenthes extract, and the right bars with recombinant nepenthesin I. The % cleavage represents the number of observed cleavages at the given residue, relative to the total number of peptides present. Data were obtained from digests of gliadin.

FIG. 15A shows a sampling of the portions of gliadin that are digested by neprosin, as detected by data-dependent LC-MS/MS (SEQ ID NO: 22).

FIG. 16 shows the location of polymorphisms in the amino acid sequence of neprosin from different species of Nepenthes (SEQ ID NO: 1).

DETAILED DESCRIPTION OF THE PREFERRED EMBODIMENTS

Figure 2:
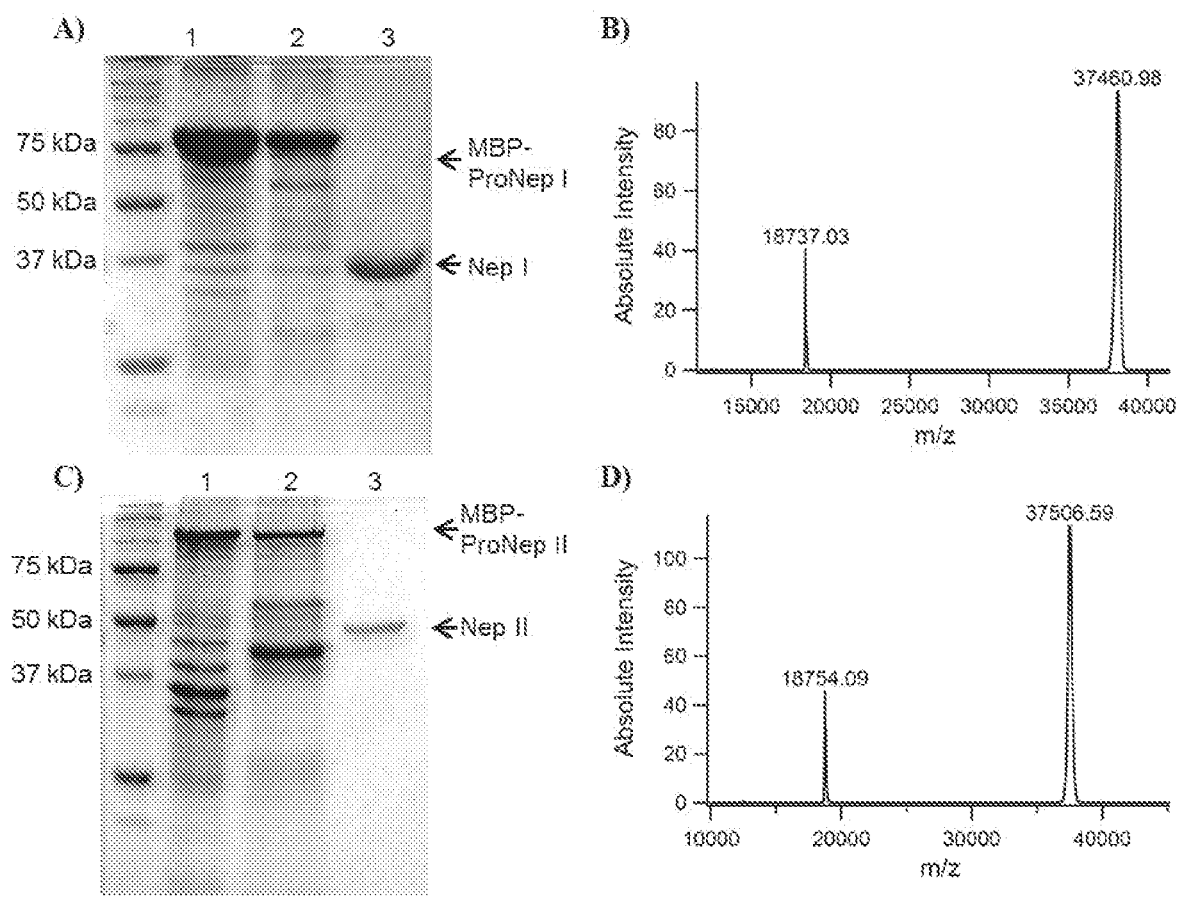
FIG. 2 indicates the sizes of recombinant nepenthesin proteins. A: Coomassie-stained gel of nepenthesin I. B: MALDI-TOF MS analysis of acid activated nepenthesin I. C: Coomassie-stained gel of nepenthesin II. D: MALDI-TOF MS analysis of acid activated nepenthesin II.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section.

I. Definitions

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

As used in the specification and claims, the singular form "a", "an" and "the" include plural references unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, a "potentially antigenic food or protein" is any food or protein that can cause an immune and/or inflammatory response in the intestine of a sensitive individual. In a preferred embodiment, the individual is a human and the food is a food intended for human consumption. Potentially antigenic foods include, without limitation, wheat, rye, barley, peanuts, nuts and seeds. In one embodiment, potentially antigenic proteins from these foods include prolamin proteins, 2S albumins, non-specific lipid transfer proteins, bifunctional α-amylase/protease inhibitors, soybean hydrophobic protein, indolines, gluten, serpins, purinins, alpha-amylase/protease inhibitors, globulins, and farinins. In a preferred embodiment, the potentially antigenic protein (or peptide) is rich in proline and/or glutamine residues. In an especially preferred embodiment, the potentially antigenic protein is gluten. In another preferred embodiment, the potentially antigenic protein is a wheat protein.

As used herein, the term "gluten" generally refers to the proteins present in wheat or related grain species, including barley and rye, which have potential harmful effect to certain individuals. Gluten proteins include gliadins such as α-gliadins, β-gliadins, γ-gliadins and ω-gliadins, which are monomeric proteins, and glutenins, which are highly heterogeneous mixtures of aggregates of high-molecular-weight and low-molecular-weight subunits held together by disulfide bonds. Many wheat gluten proteins have been characterized. See, for example, Woychik et al., Amino Acid Composition of Proteins in Wheat Gluten, *J. Agric. Food Chem.*, 9(4), 307-310 (1961). The term gluten as used herein also includes oligopeptides that can be derived from normal human digestion of gluten proteins from gluten containing foods and cause the abnormal immune response. Some of these oligopeptides are resistant to normal digestive enzymes. Gluten, including the above-mentioned proteins and oligopeptides, is believed to act as an antigen for T cells (e.g., IELs) in patients with gluten intolerance (e.g., celiac sprue). The term gluten also refers to denatured gluten, such as would be found in baked products.

As used herein, the term "gluten sensitivity and related conditions" refers to any condition stemming from intolerance or sensitivity to gluten proteins or peptides. These include, without limitation, celiac sprue (celiac disease), wheat allergy, gluten sensitivity, gluten-sensitive enteropathy, idiopathic gluten sensitivity, and dermatitis herpetiformis. Related conditions also include, without limitation, autism, attention deficit hyperactivity disorder (ADHD), rheumatoid arthritis, fibromyalgia, Crohn's disease, nutrient maladsorption, and irritable bowel syndrome (IBS).

The term "neprosin" refers to a prolyl endoprotease with a molecular weight of approximately 29 kilo Daltons (kDa). Neprosin can be isolated from the pitcher secretions of Nepenthes species. Neprosin cleaves proteins carboxy-terminal to proline, with high specificity. The enzyme is active at about pH 2 to about pH 6. In one embodiment, neprosin has the amino acid sequence of SEQ ID NO.: 1. The neprosin amino acid sequence is not homologous to any other known protein. In one embodiment, neprosin is encoded by the cDNA sequence of SEQ ID NO.: 2. In one embodiment, neprosin comprises a signal sequence. In one embodiment, the signal sequence comprises the amino acid sequence of SEQ ID NO.: 3. In one embodiment, neprosin does not comprise a signal sequence.

Neprosin includes all isoforms, isotypes, and variants of neprosin, recombinant neprosin, and salts thereof. Salts refer to those salts formed by neprosin with one or more base or one or more acid which retain the biological effectiveness and properties of the free neprosin, and which are not biologically or otherwise undesirable. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, di cyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Acids that can form salts include, but are not limited to, inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

Examples of proteases include, without limitation, aspartic proteases, serine proteases, threonine proteases, cysteine proteases, glutamic acid proteases, and metalloproteases. Proteases that can be useful in the present invention include, without limitation, BACE, cathepsin D, cathepsin E, chymosin (or "rennin"), napsin, pepsin, plasmepsin, presenilin, renin, trypsin, chemotrypsin, elastase, and cysteine endoprotease (EP) B2 (also known as EPB2). Proteases include those described, for example, in U.S. Pat. Nos. 7,320,788; 7,303,871; 7,320,788; 7,628,985; 7,910,541; and 7,943,312; PCT Pat. Pub. Nos. 2005/107786; 2008/115428; 2008/115411; 2010/021752; 2010/042203; 2011/097266 each of which is expressly incorporated herein by reference. In a preferred embodiment, the at least one additional protease is active at acidic pH, such as that found in the stomach (e.g., pH 1.5 to 3.5).

The term "nepenthesin" refers to the aspartic protease having the Enzyme Commission number EC 3.4.23.12, and includes all isoforms, isotypes, and variants of nepenthesin such as nepenthesin I and nepenthesin II, nepenthesin isoforms, and recombinant nepenthesin, and salts thereof. Nepenthesin (EC 3.4.23.12) is an aspartic protease of plant origin that can be isolated or concentrated from a variety of plant sources, such as the pitcher secretions of Nepenthes, a carnivorous pitcher plant, commonly known as monkey cups in tropical regions. Nepenthesin is described in detail in U.S. patent application Ser. No. 13/843,369, filed Mar. 15, 2013, which is incorporated herein by reference in its entirety. Sequence alignment of the known nepenthesin protein sequences (and putative nepenthesin protein sequences) is shown in FIG. 1.

In one embodiment, "effective amount" refers to that amount of a composition that results in inhibition or amelioration of symptoms in a subject or a desired biological outcome, e.g., improved clinical signs, delayed onset of disease, etc. The effective amount can be determined by one of ordinary skill in the art. The selected dosage level can depend upon the severity of the condition being treated, and the condition and prior medical history of the mammal being treated. However, it is within the skill of the art to start doses of the composition at levels lower than required to achieve the desired therapeutic effect and to gradually increase the dosage until the desired effect is achieved.

The term "manifestations of celiac disease" refers to any of the symptoms or clinical presentations of celiac disease. Such manifestations include, without limitation, intestinal inflammation, "foggy mind", depression, anxiety, ADHD-like behavior, abdominal pain, bloating, diarrhea, constipation, headaches, migraines, bone or joint pain, chronic fatigue, small intestine damage, development of tissue transglutaminase (tTG) antibodies, severe acne, vomiting, weight loss, irritability, iron-deficiency anemia, arthritis, tingling numbness in the extremities, infertility, and canker sores of the mouth. Manifestations further include small intestinal mucosal villous atrophy with crypt hyperplasia, mucosal inflammation of the intestine, malabsorption of nutrients, abdominal distension, as well as a substantially enhanced risk for the development of osteoporosis and intestinal malignancies (lymphoma and carcinoma).

"Concurrent administration," or "co-treatment," as used herein includes administration of the agents together, or before or after each other.

The term "modulate," "attenuate" or "ameliorate" means any treatment of a disease or disorder in a subject, such as a mammal, including:

preventing or protecting against the disease or disorder, that is, causing the abnormal biological reaction or symptoms not to develop;

inhibiting the disease or disorder, that is, arresting or suppressing the development of abnormal biological reactions and/or clinical symptoms; and/or relieving the disease or disorder, that is, causing the regression of abnormal biological reactions and/or symptoms.

As used herein, the term "preventing" or "inhibiting" refers to the prophylactic treatment of a subject in need thereof. The prophylactic treatment can be accomplished by providing an appropriate dose of a therapeutic agent to a subject at risk of suffering from an ailment, thereby substantially averting onset of the ailment.

As used herein, the term "condition" refers to a disease state for which the compounds, compositions and methods provided herein are being used.

As used herein, the term "patient" or "subject" refers to mammals and includes humans and non-human mammals. In particular embodiments herein, the patient or subject is a human.

The term "about" when used before a numerical value indicates that the value may vary within a reasonable range: ±5%, ±1%, or ±0.2%.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. One alignment program is BLAST, using default parameters. Examples of the programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

II. Methods

In one aspect, this invention relates to methods for modulating a condition mediated by gluten intolerance in a patient, comprising administering to the patient an effective amount of a pharmaceutical composition comprising a *Nepenthes* enzyme. In a preferred embodiment, the condition is celiac disease or a wheat allergy.

In another aspect, this invention relates to a method for attenuating or preventing production and/or recruitment of IELs in the intestine due to the presence of a peptidic food antigen in an intestine of a mammal. In one embodiment, the method comprises administering to the mammal an effective amount of a pharmaceutical composition comprising a *Nepenthes* enzyme. In one embodiment, the gluten protein is degraded by the pharmaceutical composition so as to attenuate or prevent production and/or recruitment of IELs in the intestine.

In one aspect, this invention relates to a method for attenuating or preventing intestinal inflammation due to the presence of a peptidic food antigen in the intestine of a mammal. In one embodiment, the method comprises administering to the mammal an effective amount of a pharmaceutical composition comprising a *Nepenthes* enzyme. In one embodiment, the peptidic food antigen is degraded by the enzyme(s) so as to attenuate or prevent intestinal inflammation.

In one aspect, this invention relates to a method for attenuating or preventing intraepithelial lymphocytosis due to the presence of a peptidic food antigen in an intestine of a mammal. In one embodiment, the method comprises administering to the mammal an effective amount of a pharmaceutical composition comprising a *Nepenthes* enzyme. In one embodiment, the peptidic food antigen is degraded by the pharmaceutical composition so as to attenuate or prevent intraepithelial lymphocytosis in the intestine.

In one aspect, this invention relates to a method for attenuating or preventing villous atrophy due to the presence of a peptidic food antigen in an intestine of a mammal. In one embodiment, the method comprises administering to the mammal an effective amount of a pharmaceutical composition comprising a *Nepenthes* enzyme. In one embodiment, the peptidic food antigen is degraded by the pharmaceutical composition so as to attenuate or prevent villous atrophy in the intestine. In one embodiment, the villous atrophy is a result of inflammation of the intestine.

In one embodiment, the *Nepenthes* enzyme is nepenthesin I, nepenthesin II, neprosin, variant thereof, or a mixture thereof. In a preferred embodiment, the pharmaceutical formulation is a sustained release formulation.

In one embodiment, the variant is a protein having an amino acid sequence having at least 85% sequence homology to the amino acid sequence of SEQ ID NO.: 1, SEQ ID NO.: 5, SEQ ID NO.: 6, SEQ ID NO.: 7, SEQ ID NO.: 8, SEQ ID NO.: 9, SEQ ID NO.:20, or SEQ ID NO.:21. In one embodiment, the variant is a protein having an amino acid sequence having at least 85% sequence homology to the amino acid sequence of SEQ ID NO.: 1. In one embodiment, the variant is a protein having an amino acid sequence having at least 85% sequence homology to the amino acid sequence of SEQ ID NO.: 5. In one embodiment, the variant is a protein having an amino acid sequence having at least 85% sequence homology to the amino acid sequence of SEQ ID NO.: 6. In one embodiment, the variant is a protein having an amino acid sequence having at least 85% sequence homology to the amino acid sequence of SEQ ID NO.: 7. In one embodiment, the variant is a protein having an amino acid sequence having at least 85% sequence homology to the amino acid sequence of SEQ ID NO.: 8. In one embodiment, the variant is a protein having an amino acid sequence having at least 85% sequence homology to the amino acid sequence of SEQ ID NO.: 9. In one embodiment, the variant is a protein having an amino acid sequence having at least 85% sequence homology to the amino acid sequence of SEQ ID NO.: 20. In one embodiment, the variant is a protein having an amino acid sequence having at least 85% sequence homology to the amino acid sequence of SEQ ID NO.: 21.

In one embodiment, the pharmaceutical composition comprises an extract of *Nepenthes* pitcher fluid. In one embodiment, the pharmaceutical composition comprises nepenthesin I, nepenthesin II, and/or neprosin purified from an extract of *Nepenthes* pitcher fluid. In one embodiment, at least one of nepenthesin I, nepenthesin II, neprosin, or variant thereof is a recombinant protein. In one embodiment, the pharmaceutical composition is between about pH 5 and about pH 8 prior to administration. Pharmaceutical compositions for use in the methods described herein are discussed in more detail below.

In a preferred embodiment, the mammal is a human. In one embodiment, the human suffers from a disease selected from the group consisting of gluten intolerance, celiac disease, attention deficit hyperactivity disorder, autism, rheumatoid arthritis, fibromyalgia, and dermatitis herpetiformis. In one embodiment, the human suffers from a food allergy.

In one embodiment, the pharmaceutical composition is orally administered prior to, during, or immediately after consumption of a gluten-containing food.

In some embodiments, the pharmaceutical composition is administered to the subject prior to ingestion by the subject of the food comprising gluten or suspect of comprising gluten. In some embodiments, the pharmaceutical composition is administered within a period that the enzyme is at least partially effective (for example, at least about 10%, 20%, 50%, 70%, 90% of original activity) in degrading gluten in the food that the subject will ingest. In some embodiments, the pharmaceutical composition is administered not more than about 4 hours, 3 hours, 2 hours, 1 hour, or 30 minutes prior to ingestion of the food by the subject.

In some embodiments, the pharmaceutical composition is administered to the subject concurrently with ingestion by the subject of the potentially immunogenic food. In some embodiments, the enzyme composition is administered with the food. In some embodiments, the pharmaceutical composition is administered separately from the food.

In some embodiments, the pharmaceutical composition is administered to the subject shortly after ingestion by the subject of the potentially immunogenic food. In some embodiments, the pharmaceutical composition is administered within a period that at least part (for example, at least about 10%, 20%, 50%, 70%, 90%) of the antigen(s) in the food is still in the stomach of the subject. In some embodiments, the pharmaceutical composition is administered not more than 4 hours, 3 hours, 2 hours, 1 hour, or 30 minutes after ingestion of the food by the subject.

Typically, the pharmaceutical composition is administered in an amount that is safe and sufficient to produce the desired effect of detoxification of peptidic food antigen(s). The dosage of the pharmaceutical composition can vary depending on many factors such as the particular enzyme administered, the subject's sensitivity to the food, the amount and types of antigen-containing food ingested, the pharmacodynamic properties of the enzyme, the mode of administration, the age, health and weight of the recipient, the nature and extent of the symptoms, the frequency of the treatment and the type of concurrent treatment, if any, and the clearance rate of the enzyme. One of skill in the art can determine the appropriate dosage based on the above factors. The composition may be administered initially in a suitable dosage that may be adjusted as required, depending on the clinical response. In vitro assays may optionally be employed to help identify optimal dosage ranges. The precise dose to be employed in the formulation will also depend on the route of administration and/or the seriousness of the disease or disorder, and should be decided according to the judgment of the practitioner and each subject's circumstances.

The dosage or dosing regimen of an adult subject may be proportionally adjusted for children and infants, and also adjusted for other administration or other formats, in proportion for example to molecular weight or immune response. Administration or treatments may be repeated at appropriate intervals, at the discretion of the physician.

Generally, the pharmaceutical composition is administered when needed, such as when the subject will be or is consuming or has consumed a food comprising an antigenic protein or suspected of comprising an antigenic protein. In any case, it can be administered in dosages of about 0.001 mg to about 1000 mg of enzyme per kg body weight per day, or about 1 mg to about 100 g per dose for an average person. In some embodiments, the enzyme can be administered at 0.001, 0.01, 0.1, 1, 5, 10, 50, 100, 500, or 1000 mg/kg body weight per day, and ranges between any two of these values (including endpoints). In some embodiments, the enzyme can be administered at 1 mg, 10 mg, 100 mg, 200 mg, 500 mg, 700 mg, 1 g, 10 g, 20 g, 50 g, 70 g, 100 g per dose, and ranges between any two of these values (including endpoints). In some embodiments, it may be administered once, twice, three times, etc. a day, depending on the number of times the subject ingests a food comprising an antigenic protein and/or how much of such food is consumed. The amount of enzyme recited herein may relate to total enzyme or each enzyme in the composition.

In some embodiments, the amount of pharmaceutical composition administered is dependent on the amount (or approximate amount) of substrate (e.g., gluten and/or other protein or potentially antigenic protein) consumed/to be consumed. In one embodiment, about 1 mg to about 1 g of enzyme is administered per 1 g of substrate. In one embodiment, about 5 mg to about 1 g of enzyme is administered per 1 g of substrate. In one embodiment, about 10 mg to about 1 g of enzyme is administered per 1 g of substrate. In one embodiment, about 100 mg to about 1 g of enzyme is administered per 1 g of substrate. In one embodiment, about 1 mg to about 500 mg of enzyme is administered per 1 g of substrate. In one embodiment, about 1 mg to about 250 mg of enzyme is administered per 1 g of substrate. In one embodiment, about 1 mg to about 100 mg of enzyme is administered per 1 g of substrate. In one embodiment, about 1 mg to about 10 mg of enzyme is administered per 1 g of substrate. This includes any values with these ranges (including endpoints), and subranges between any two of these values.

In one embodiment, the ratio of substrate to enzyme administered is between about 1:1 and about 10000:1. In a preferred embodiment, the ratio of substrate to enzyme is between about 10:1 and about 1000:1. In one embodiment, the ratio of substrate to enzyme is between about 10:1 and about 100:1.

The pharmaceutical composition of this invention can be administered as the sole active agent or they can be administered in combination with other agents (simultaneously, sequentially or separately, or through co-formulation), including other compounds that demonstrate the same or a similar therapeutic activity and that are determined to safe and efficacious for such combined administration.

In some embodiments, the pharmaceutical composition is administered with an additional enzyme, such as a gastric protease, an aspartic protease (such as pepsin, pepsinogen or those described by Chen et al., Aspartic proteases gene family in rice: Gene structure and expression, predicted protein features and phylogenetic relation, *Gene* 442:108-118 (2009)), and enzymes such as another prolyl endopeptidase (PEP), dipeptidyl peptidase IV (DPP IV), and dipeptidyl carboxypeptidase (DCP) or cysteine proteinase B (described in U.S. Pat. No. 7,910,541). In one embodiment, the other enzyme is administered in the form of bacteria that produce and/or secrete the additional enzyme. In one embodiment, the bacteria are engineered to produce and/or secrete nepenthesin I, nepenthesin II, neprosin, and/or a variant thereof.

In some embodiments, the pharmaceutical composition is administered to the subject with another agent. Non-limiting examples of agents that can be administered with the pharmaceutical composition include inhibitors of tissue transglutaminase, anti-inflammatory agents such as amylases, glucoamylases, endopeptidases, HMG-CoA reductase inhibitors (e.g., compactin, lovastatin, simvastatin, pravastatin and atorvastatin), leukotriene receptor antagonists (e.g., montelukast and zafirlukast), COX-2 inhibitors (e.g., celecoxib and rofecoxib), p38 MAP kinase inhibitors (e.g., BIRB-796); mast cell-stabilizing agents such as sodium chromoglycate (chromolyn), pemirolast, proxicromil, repirinast, doxantrazole, amlexanox nedocromil and probicromil, anti-ulcer agents, anti-allergy agents such as anti-histamine agents (e.g., acrivastine, cetirizine, desloratadine, ebastine, fexofenadine, levocetirizine, loratadine and mizolastine), inhibitors of transglutaminase 2 (TG2), anti-TNFα agents, and antibiotics. In one embodiment, the additional agent is a probiotic. Probiotics include, without limitation, *lactobacillus*, yeast, *bacillus*, or *bifidobacterium* species and strains. In one embodiment, the other agent is elafin. In one embodiment, the other agent is administered in the form of bacteria that produce and/or secrete the additional agent.

In some embodiments, the other agent comprises an enzyme (e.g., protease) that is active in the intestine. Without being limited by theory, it is believed that such enzymes may act synergistically with the enzyme(s) of the pharmaceutical composition to further degrade immunogenic proteins.

Also provided herein is the use of an enzyme composition comprising nepenthesin I, nepenthesin II, neprosin, a variant thereof, and/or a salt thereof in the manufacture of a medicament for the treatment or prevention of one of the aforementioned conditions and diseases.

III. Pharmaceutical Compositions

The pharmaceutical composition can be administered in a variety of compositions alone or with appropriate, pharmaceutically acceptable carriers, excipients, or diluents.

Accordingly, in another aspect, provided herein is a composition comprising nepenthesin I, nepenthesin II, neprosin, a variant thereof, and/or a salt thereof. In some embodiments, the composition is a pharmaceutical composition. The compositions may be formulated into solid, semi-solid, or liquid forms, such as tablets, capsules, powders, granules, ointments, solutions, injections, gels, and microspheres. Administration of the composition can be achieved in various ways, for example, by oral administration.

In some embodiments, the pharmaceutical composition comprises a therapeutically effective amount of nepenthesin I, nepenthesin II, neprosin, variant thereof, or mixture thereof and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, incorporated in its entirety by reference herein. Such compositions will contain a therapeutically effective amount of the enzyme(s), preferably in purified form, together with a suitable amount of carrier so as to provide the form for proper administration to the subject. The formulation should suit the mode of administration.

For oral administration, the pharmaceutical composition can be used alone or in combination with appropriate additives to make tablets, powders, granules, capsules, syrups, liquids, suspensions, etc. For example, solid oral forms of the composition can be prepared with conventional additives, disintegrators, lubricants, diluents, buffering agents, moistening agents, preservatives and flavoring agents. Non-limiting examples of excipients include lactose, mannitol, corn starch, potato starch, crystalline cellulose, cellulose derivatives, acacia, corn starch, sodium carboxymethylcellulose, talc, magnesium stearate, flavors and colors. In some embodiments, the formulation releases the enzyme(s) in the stomach of the subject so that the peptidic food antigen(s) can be degraded by the enzyme(s).

The composition can be lyophilized from an aqueous solution optionally in the presence of appropriate buffers (e.g. phosphate, citrate, histidine, imidazole buffers) and excipients (e.g. cryoprotectants such as sucrose, lactose, trehalose). Lyophilized cakes can optionally be blended with excipients and made into different forms.

In another aspect, provided are methods for treating gluten intolerance or an associated condition, such as celiac disease, wheat allergy, gluten sensitivity and dermatitis herpetiformis, in a patient in need thereof, comprising treating a food comprising gluten or suspected of comprising gluten with an effective amount of the composition prior to consumption by the patient. In some embodiments, the food is combined with an effective amount of the composition during its preparation. In one embodiment, the composition is added after any heating steps in the food preparation. In one embodiment, the composition is added before one or more heating steps in the food preparation.

Nepenthesin I, nepenthesin II, and neprosin occur as proenzymes in *Nepenthes* prior to activation. That is, the protein includes a propeptide that is cleaved in order to activate the enzyme in the pitcher fluid. In one embodiment, the composition comprises nepenthesin I, nepenthesin II, neprosin, a variant thereof, and/or a salt thereof comprising a propeptide. In one embodiment, the propeptide is adjacent to the N terminus of the enzyme. In one embodiment, the propeptide is the naturally-occurring propeptide for the enzyme. In one embodiment, the propeptide is a heterologous propeptide (e.g., from a different protein or species, or synthetic). In one embodiment, the propeptide is cleaved by acidic conditions. In one embodiment, the propeptide is cleaved by an enzyme. In one embodiment, the presence of the propeptide results in delayed activity of the enzyme in the stomach (e.g., due to the time required to remove the propeptide and produce the mature enzyme). In one embodiment, the propeptide is engineered to be removed more slowly in order to delay activity of the enzyme in the stomach. In one embodiment, the propeptide is engineered to be removed more quickly in order to speed up activity of the enzyme in the stomach.

In a preferred embodiment, the formulation is a controlled release formulation. The term "controlled release formulation" includes sustained release and time-release formulations. Controlled release formulations are well-known in the art. These include excipients that allow for sustained, periodic, pulse, or delayed release of the drug. Controlled release formulations include, without limitation, embedding of the drug into a matrix; enteric coatings; micro-encapsulation; gels and hydrogels; and any other formulation that allows for controlled release of a drug.

In some embodiments, the composition is administered as a food additive together with a food comprising or suspected of comprising a potentially antigenic food protein. In one embodiment, the food comprises or is suspected of comprising gluten, for example bread, pasta, cereal, and the like, made from wheat, rye and barley, etc. In some embodiments, the composition is added as an ingredient in such food. In some embodiments, the composition is dispersed into a food prior to consumption, optionally at a pH where it is inactive, such as a pH of about or above 5. In some embodiments, the composition can be made or incorporated into a powder, a spread, a spray, a sauce, a dip, a whipped cream, etc., that can be applied to the food when the food is being consumed by a patient. In some embodiments, the composition can be made into forms that appeal to one's appetite, such as candies, chewing gums, dietary supplement chews, syrup, etc. for easy administration. In some embodiments, the composition can be mixed with common food items, such as sugar, salt, salad dressing, spices, cheese, butter, margarines, spreads, butter, frying shortenings, mayonnaises, dairy products, nut butters, seed butters, kernel butters, peanut butter, etc. Preferably, the food items or additives comprising the composition do not require heating before being ingested by a patient so that possible loss of activity of the enzyme(s) due to elevated temperature can be minimized.

In one embodiment, the enzyme(s) in the composition is activated upon contact with acid (i.e., in the stomach).

In another aspect, provided is a food product comprising neprosin, nepenthesin I, nepenthesin II, a variant thereof, or a combination thereof. In some embodiments, the food product comprises gluten or is suspected of comprising gluten, such as bakery products (e.g., cakes, muffins, donuts, pastries, rolls, and bread), pasta, crackers, tortilla chips, cereal etc. made from wheat, rye and barley. In some embodiments, the food product can be consumed with another food product comprising gluten or suspected of comprising gluten. Non-limiting examples of such food include a powder, a spread, a spray, a sauce, a dip, a whipped cream, candies, chewing gums, syrup, sugar, salt, salad dressing, spices, cheese, butter, margarines, spreads, butter, frying shortenings, mayonnaises, dairy products, nut butters, seed butters, kernel butters, peanut butter, etc.

In some embodiments, the composition comprising neprosin, nepenthesin I, nepenthesin II, a variant thereof, or a combination thereof is admixed with food, or used to pre-treat foodstuffs containing glutens. The composition present in foods can be enzymatically active to reduce the level of gluten in the food prior to or during ingestion.

In one aspect of the invention, a composition comprising neprosin, nepenthesin I, nepenthesin II, a variant thereof, or a combination thereof is added to food before the food is consumed. In one embodiment, the invention is directed to a dispenser comprising an inner excipient and an effective amount of the pharmaceutical composition to digest gluten. In one embodiment, the pharmaceutical composition and/or inner excipient are added to food before the food is consumed. In one embodiment, the food comprises gluten or is suspected to comprise gluten. In one embodiment, the inner excipient comprises sodium chloride or sodium iodide, or a mixture thereof. In one embodiment, the pharmaceutical composition and/or inner excipient are in granular form, sized to efficiently dispense from said dispenser.

In some embodiments, the composition (such as pharmaceutical composition or edible composition) or food product comprises from about 0.1% to about 99%, from about 0.5% to about 95%, from about 1% to about 95%, from about 5% to about 95%, from about 10% to about 90%, from about 20% to about 80%, from about 25% to about 75% of the enzyme(s). In some embodiments, the amount of enzyme in the composition (such as pharmaceutical composition or edible composition) or food product is about 0.01%, about 0.1%, about 0.5%, about 1%, about 5%, about 10%, about 20%, about 25%, about 30%, about 35%, about 40%, about 45%, about 50%, about 55%, about 60%, about 65%, about 70%, about 75%, about 80%, about 85%, about 90%, or about 95% of the total composition or food product, or a range between any two of the values (including end points).

In some embodiments, the composition comprises neprosin and nepenthesin, or a variant thereof. In some embodiments, the nepenthesin is nepenthesin I and/or nepenthesin II, or a variant thereof. In some embodiments, the nepenthesin is recombinant nepenthesin I and/or recombinant nepenthesin II, or a variant thereof. In some embodiments, the nepenthesin is recombinant nepenthesin I and recombinant nepenthesin II, or a variant of each thereof. In some embodiments, the neprosin is recombinant neprosin, or a variant thereof. In a preferred embodiment, the composition comprises nepenthesin I, nepenthesin II, and/or neprosin comprising the amino acid sequence(s) of nepenthesin I, nepenthesin II, and/or neprosin from a *Nepenthes* species, or a variant(s) thereof.

Nepenthesin I mRNA/cDNA sequences have been described from several *Nepenthes* species, for example, *Nepenthes mirabilis* (GenBank Accession No. JX494401), *Nepenthes gracilis* (GenBank Accession No. AB114914), and *Nepenthes alata* (GenBank Accession No. AB266803). Nepenthesin II mRNA/cDNA sequences have been described from several *Nepenthes* species, for example, *Nepenthes mirabilis* (GenBank Accession No. JX494402), and *Nepenthes gracilis* (GenBank Accession No. AB114915).

Nepenthesin I protein sequences have been described from several *Nepenthes* species, for example, *Nepenthes mirabilis* (GenBank Accession No. AFV26024; SEQ ID NO.: 5), *Nepenthes gracilis* (GenBank Accession No. BAD07474; SEQ ID NO.: 7), and *Nepenthes alata* (GenBank Accession No. BAF98915; SEQ ID NO.: 6). Nepenthesin II protein sequences have been described from several *Nepenthes* species, for example, *Nepenthes mirabilis* (GenBank Accession No. AFV26025; SEQ ID NO.: 8), and *Nepenthes gracilis* (GenBank Accession No. BAD07475; SEQ ID NO.: 9). The sequences are also found in U.S. Patent Application Publication No. 2014/0186330, which is incorporated herein by reference in its entirety.

Each of the sequences represented by the GenBank Accession Nos. provided herein are incorporated herein by reference in their entireties.

In some embodiments, the nepenthesin is a variant of nepenthesin having at least about 85% sequence homology to an amino acid sequence of nepenthesin I (e.g., SEQ ID NO.: 5; SEQ ID NO.: 6; SEQ ID NO.: 7; or SEQ ID NO.: 21). In some embodiments, the variant has at least about 90% sequence homology to an amino acid sequence of nepenthesin I. In some embodiments, the variant has at least about 95% sequence homology to an amino acid sequence of nepenthesin I. In some embodiments, the variant has at least about 96% sequence homology to an amino acid sequence of nepenthesin I. In some embodiments, the variant has at least about 97% sequence homology to an amino acid sequence of nepenthesin I. In some embodiments, the variant has at least about 98% sequence homology to an amino acid sequence of nepenthesin I. In some embodiments, the variant has at least about 99% sequence homology to an amino acid sequence of nepenthesin I. In one embodiment, the nepenthesin comprises the amino acid sequence of SEQ ID NO.: 5; SEQ ID NO.: 6; SEQ ID NO.: 7; or SEQ ID NO.: 21.

In some embodiments, the nepenthesin is a variant of nepenthesin having at least about 85% sequence homology to an amino acid sequence of nepenthesin II (e.g., SEQ ID NO.: 8; SEQ ID NO.: 9; or SEQ ID NO.: 22). In some embodiments, the variant has at least about 90% sequence homology to an amino acid sequence of nepenthesin II. In some embodiments, the variant has at least about 95% sequence homology to an amino acid sequence of nepenthesin II. In some embodiments, the variant has at least about 96% sequence homology to an amino acid sequence of nepenthesin II. In some embodiments, the variant has at least about 97% sequence homology to an amino acid sequence of nepenthesin II. In some embodiments, the variant has at least about 98% sequence homology to an amino acid sequence of nepenthesin II. In some embodiments, the variant has at least about 99% sequence homology to an amino acid sequence of nepenthesin II. In one embodiment, the nepenthesin comprises the amino acid sequence of SEQ ID NO.: 8; SEQ ID NO.: 9; or SEQ ID NO.: 22.

In one aspect of the invention, the ratio of neprosin to nepenthesin I and/or II in the composition is such that the peptidic food antigen is cleaved into sufficiently small and/or innocuous fragments so as to prevent gluten intolerance, celiac disease, wheat allergy, or dermatitis herpetiformis, inflammation, IEL proliferation or recruitment, intraepithelial lymphocytosis, and/or villous atrophy, or any symptom thereof, in an intestine of the subject. In some embodiments, the neprosin:nepenthesin ratio is between about 1:100 to about 100:1.

In some embodiments, the composition comprises a ratio of neprosin to nepenthesin (nepenthesin I and/or II) of at least about 100:1. In some embodiments, the composition comprises a ratio of neprosin to nepenthesin of at least about 90:1. In some embodiments, the composition comprises a ratio of neprosin to nepenthesin of at least about 70:1. In some embodiments, the composition comprises a ratio of neprosin to nepenthesin of at least about 60:1. In some embodiments, the composition comprises a ratio of neprosin to nepenthesin of at least about 50:1. In some embodiments, the composition comprises a ratio of neprosin to nepenthesin of at least about 40:1. In some embodiments, the composition comprises a ratio of neprosin to nepenthesin of at least about 30:1. In some embodiments, the composition comprises a ratio of neprosin to nepenthesin of at least about 20:1. In some embodiments, the composition comprises a ratio of neprosin to nepenthesin of at least about 10:1. In some embodiments, the composition comprises a ratio of neprosin to nepenthesin of at least about 5:1. In some embodiments, the composition comprises a ratio of neprosin to nepenthesin of at least about 4:1. In some embodiments, the composition comprises a ratio of neprosin to nepenthesin of at least about 3:1. In some embodiments, the composition comprises a ratio of neprosin to nepenthesin of at least about 2:1. In some embodiments, the composition comprises a ratio of neprosin to nepenthesin of at least about 1:1. In some embodiments, the composition comprises a ratio of neprosin to nepenthesin of at least about 1:2. In some embodiments, the composition comprises a ratio of neprosin to nepenthesin of at least about 1:3. In some embodiments, the composition comprises a ratio of neprosin to nepenthesin of at least about 1:4. In some embodiments, the composition comprises a ratio of neprosin to nepenthesin of at least about 1:5. In some embodiments, the composition comprises a ratio of neprosin to nepenthesin of at least about 1:10. In some embodiments, the composition comprises a ratio of neprosin to nepenthesin of at least about 1:20. In some embodiments, the composition comprises a ratio of neprosin to nepenthesin of at least about 1:30. In some embodiments, the composition comprises a ratio of neprosin to nepenthesin of at least about 1:40. In some embodiments, the composition comprises a ratio of neprosin to nepenthesin of at least about 1:50. In some embodiments, the composition comprises a ratio of neprosin to nepenthesin of at least about 1:60. In some embodiments, the composition comprises a ratio of neprosin to nepenthesin of at least about 1:70. In some embodiments, the composition comprises a ratio of neprosin to nepenthesin of at least about 1:80. In some embodiments, the composition comprises a ratio of neprosin to nepenthesin of at least about 1:90. In some embodiments, the composition comprises a ratio of neprosin to nepenthesin of at least about 1:100.

In one aspect of the invention, the ratio of nepenthesin I to nepenthesin II in the composition is such that the peptidic food antigen is cleaved into sufficiently small and/or innocuous fragments so as to prevent inflammation, IEL proliferation or recruitment, intraepithelial lymphocytosis, and/or villous atrophy in an intestine of the subject. In some embodiments, the nepenthesin I:nepenthesin II ratio is between about 1:100 to about 100:1.

In some embodiments, the composition comprises a ratio of nepenthesin I to nepenthesin II of at least about 100:1. In some embodiments, the composition comprises a ratio of nepenthesin I to nepenthesin II of at least about 90:1. In some embodiments, the composition comprises a ratio of nepenthesin I to nepenthesin II of at least about 70:1. In some embodiments, the composition comprises a ratio of nepenthesin I to nepenthesin II of at least about 60:1. In some embodiments, the composition comprises a ratio of nepenthesin I to nepenthesin II of at least about 50:1. In some embodiments, the composition comprises a ratio of nepenthesin I to nepenthesin II of at least about 40:1. In some embodiments, the composition comprises a ratio of nepenthesin I to nepenthesin II of at least about 30:1. In some embodiments, the composition comprises a ratio of nepenthesin I to nepenthesin II of at least about 20:1. In some embodiments, the composition comprises a ratio of nepenthesin I to nepenthesin II of at least about 10:1. In some embodiments, the composition comprises a ratio of nepenthesin I to nepenthesin II of at least about 5:1. In some embodiments, the composition comprises a ratio of nepenthesin I to nepenthesin II of at least about 4:1. In some embodiments, the composition comprises a ratio of nepenthesin I to nepenthesin II of at least about 3:1. In some embodiments, the composition comprises a ratio of nepenthesin I to nepenthesin II of at least about 2:1. In some embodiments, the composition comprises a ratio of nepenthesin I to nepenthesin II of at least about 1:1. In some embodiments, the composition comprises a ratio of nepenthesin I to nepenthesin II of at least about 1:2. In some embodiments, the composition comprises a ratio of nepenthesin I to nepenthesin II of at least about 1:3. In some embodiments, the composition comprises a ratio of nepenthesin I to nepenthesin II of at least about 1:4. In some embodiments, the composition comprises a ratio of nepenthesin I to nepenthesin II of at least about 1:5. In some embodiments, the composition comprises a ratio of nepenthesin I to nepenthesin II of at least about 1:10. In some embodiments, the composition comprises a ratio of nepenthesin I to nepenthesin II of at least about 1:20. In some embodiments, the composition comprises a ratio of nepenthesin I to nepenthesin II of at least about 1:30. In some embodiments, the composition comprises a ratio of nepenthesin I to nepenthesin II of at least about 1:40. In some embodiments, the composition comprises a ratio of nepenthesin I to nepenthesin II of at least about 1:50. In some embodiments, the composition comprises a ratio of nepenthesin I to nepenthesin II of at least about 1:60. In some embodiments, the composition comprises a ratio of nepenthesin I to nepenthesin II of at least about 1:70. In some embodiments, the composition comprises a ratio of nepenthesin I to nepenthesin II of at least about 1:80. In some embodiments, the composition comprises a ratio of nepenthesin I to nepenthesin II of at least about 1:90. In some embodiments, the composition comprises a ratio of nepenthesin I to nepenthesin II of at least about 1:100.

IV. Methods of Preparation

It is contemplated that nepenthesin and/or neprosin can be concentrated (or extracted) or purified by methods known in the art, for example (but not limited to) filtration or affinity purification based on immobilized pepstatin, from a natural source, including pitcher secretions of plants such as *Nepenthes*. Classical protein chromatography, such as size exclusion chromatography (also known as gel permeation chromatography) and/or chromatofocusing chromatography, may also be used to concentrate (or extract) or purify nepenthesin and/or neprosin. Chromatofocusing may be used prior to or after size exclusion. Nepenthesin I, nepenthesin II, and neprosin are found in relatively small quantity in natural plant secretions. Production of nepenthesin I, nepenthesin II, and/or neprosin can be increased, for example, using bioengineering technologies to create transgenic plants that express and/or secrete increased amounts of the desired enzyme(s), or a variant thereof.

Besides being isolated from a plant source, the *Nepenthes* enzyme or variant thereof may be prepared by chemical synthesis. Chemical synthesis can be achieved by coupling of the amino acids according to the sequence of the desired enzyme or variant. Various peptide coupling methods and commercial peptide synthetic apparatuses are available to synthesis peptide or proteins, for example, automated synthesizers by Applied Biosystems, Inc., Foster City, Calif., Beckman, and other manufacturers.

In another aspect, provided is a method of preparing *Nepenthes* enzyme or variant thereof using recombinant production systems by transforming or transfecting a cell with the DNA (e.g., cDNA) and/or messenger RNA of the enzyme(s) so that the cell is capable of producing the enzyme(s). For example, nepenthesin can be produced by establishing host-vector systems in organisms such as *Escherichia coli, Saccharomyces cerevisiae, Pichia pastoris, Lactobacillus*, Bacilli, Aspergilli, and plant cell cultures, such as tobacco cells, etc.

Vectors and host cells, such as *E. coli*, comprising polynucleotides and compositions containing any of the polynucleotides or polypeptides as described herein are also provided.

In another aspect, provided is a method for producing recombinant *Nepenthes* enzyme (nepenthesin I, nepenthesin II, and/or neprosin, or a variant thereof) comprising expressing in a chosen host organism a nucleic acid sequence which encodes said enzyme, and inserting the nucleic acid sequence into an appropriately designed vector. In one aspect, the recombinant enzyme is nepenthesin I or a variant thereof. In one aspect, the recombinant enzyme is nepenthesin II or a variant thereof. In one aspect, the recombinant enzyme is neprosin or a variant thereof. In one aspect, the recombinant enzyme is a mixture of nepenthesin I, nepenthesin II, and/or neprosin or variant thereof.

In another aspect, provided is a composition comprising recombinant nepenthesin such as nepenthesin I and/or nepenthesin II or a variant thereof. In one aspect, the recombinant nepenthesin is nepenthesin I or a variant thereof. In one aspect, the recombinant nepenthesin is nepenthesin II or a variant thereof. In one aspect, the recombinant nepenthesin is a mixture of nepenthesin I and nepenthesin II or variants thereof.

In one aspect, this invention relates to a cDNA as described herein. In one embodiment, this invention relates to a vector comprising a cDNA as described herein. In a preferred embodiment, the vector is an expression vector. In one embodiment, this invention relates to a cell expressing recombinant nepenthesin I, recombinant nepenthesin II, recombinant neprosin, a variant or mixture thereof.

In some embodiments, biosynthesis of *Nepenthes* enzyme(s) can be achieved by transforming a cell with a vector comprising a cDNA that encodes nepenthesin I, for example the nucleotide sequence of SEQ ID NO. 4, SEQ ID NO. 5, SEQ ID NO.: 6, GenBank Accession No. JX494401, GenBank Accession No. AB114914, or GenBank Accession No. AB266803. In some embodiments, biosynthesis of nepenthesin can be achieved by transforming a cell with a vector comprising a sequence homologous to a cDNA which encodes nepenthesin I, which sequence encodes a protein with protease activity. The sequence may have at least about 60% homology to a cDNA that encodes nepenthesin I. The sequence may have at least about 70% homology to a cDNA that encodes nepenthesin I. The sequence may have at least about 80% homology to a cDNA that encodes nepenthesin I. The sequence may have at least about 85% homology to a cDNA that encodes nepenthesin I. The sequence may have at least about 90% homology to a cDNA that encodes nepenthesin I. The sequence may have at least about 95% homology to a cDNA that encodes nepenthesin I. The sequence may have at least about 96% homology to a cDNA that encodes nepenthesin I. The sequence may have at least about 97% homology to a cDNA that encodes nepenthesin I. The sequence may have at least about 98% homology to a cDNA that encodes nepenthesin I. The sequence may have at least about 99% homology to a cDNA that encodes nepenthesin I. In a preferred embodiment, the sequence encodes a variant of nepenthesin I that retains glutenase activity. In a particularly preferred embodiment, the sequence encodes a variant of nepenthesin I that degrades at least one toxic gluten peptide.

In some embodiments, biosynthesis of *Nepenthes* enzyme(s) can be achieved by transforming a cell with a vector comprising a cDNA that encodes nepenthesin II, for example the nucleotide sequence of SEQ ID NO.: 8, SEQ ID NO.: 9, GenBank Accession No. JX494402 or GenBank Accession No. AB114915. In some embodiments, biosynthesis of nepenthesin can be achieved by transforming a cell with a vector comprising a sequence homologous to a cDNA which encodes nepenthesin II, which sequence encodes a protein with protease activity. The sequence may have at least about 60% homology to a cDNA that encodes nepenthesin II. The sequence may have at least about 70% homology to a cDNA that encodes nepenthesin II. The sequence may have at least about 80% homology to a cDNA that encodes nepenthesin II. The sequence may have at least about 85% homology to a cDNA that encodes nepenthesin II. The sequence may have at least about 90% homology to a cDNA that encodes nepenthesin II. The sequence may have at least about 95% homology to a cDNA that encodes nepenthesin II. The sequence may have at least about 96% homology to a cDNA that encodes nepenthesin II. The sequence may have at least about 97% homology to a cDNA that encodes nepenthesin II. The sequence may have at least about 98% homology to a cDNA that encodes nepenthesin II. The sequence may have at least about 99% homology to a cDNA that encodes nepenthesin II. In a preferred embodiment, the sequence encodes a variant of nepenthesin II that retains glutenase activity. In a particularly preferred embodiment, the sequence encodes a variant of nepenthesin II that degrades at least one toxic gluten peptide.

In some embodiments, biosynthesis of *Nepenthes* enzyme(s) can be achieved by transforming a cell with a vector comprising a cDNA that encodes neprosin, for example the nucleotide sequence of SEQ ID NO.: 2. In some embodiments, biosynthesis of neprosin can be achieved by transforming a cell with a vector comprising a sequence homologous to a cDNA which encodes neprosin, which sequence encodes a protein with protease activity. The sequence may have at least about 60% homology to a cDNA that encodes neprosin. The sequence may have at least about 70% homology to a cDNA that encodes neprosin. The sequence may have at least about 80% homology to a cDNA that encodes neprosin. The sequence may have at least about 85% homology to a cDNA that encodes neprosin. The sequence may have at least about 90% homology to a cDNA that encodes neprosin. The sequence may have at least about 95% homology to a cDNA that encodes neprosin. The sequence may have at least about 96% homology to a cDNA that encodes neprosin. The sequence may have at least about 97% homology to a cDNA that encodes neprosin. The sequence may have at least about 98% homology to a cDNA that encodes neprosin. The sequence may have at least about 99% homology to a cDNA that encodes neprosin. In a preferred embodiment, the sequence encodes a variant of neprosin that retains prolyl endoprotease activity. In an especially preferred embodiment, the sequence encodes a variant of neprosin that retains glutenase activity. In a particularly preferred embodiment, the sequence encodes a variant of neprosin that degrades at least one toxic gluten peptide.

Without being bound by theory, it is believed that inflammatory response to gluten in the intestines of affected individuals is due to the incomplete hydrolysis of gluten proteins, leading to the formation of toxic (immunotoxic) gluten peptides. Several immunotoxic and/or potentially immunotoxic gluten peptides are known. These include, but are not limited to, the 33-mer (SEQ ID NO.: 15, LQLQPF (PQPQLPY)$_3$PQPQPF) and p31-49 (SEQ ID NO.: 16, LGQQQPFPPQQPYPQPQPF) from α-gliadin; Gly-156 (SEQ ID NO.: 17, QQQQPPFSQQQQSPFSQQQQ) from low molecular weight glutenin; and the nonapeptide repeat (SEQ ID NO.: 18, GYYPTSPQQ) and hexapeptide repeat (SEQ ID NO.: 19, PGQGQQ) from high molecular weight glutenin.

In some embodiments, nepenthesin I, nepenthesin II, neprosin and/or a variant thereof is synthesized by transfecting, infecting, or transforming a cell with one or more vectors comprising a cDNA sequence of each desired enzyme. That is, a single cell, cell line, or organism may be engineered so as to produce two or more enzymes. In some embodiments, the desired enzymes are synthesized by separate cells and combined in the pharmaceutical composition. In a preferred embodiment, the recombinant nepenthesin I, nepenthesin II, neprosin and/or a variant thereof is not glycosylated. In one embodiment, the recombinant nepenthesin I, nepenthesin II, neprosin and/or a variant thereof has a different glycosylation pattern than the natural enzyme (i.e., nepenthesin I, nepenthesin II, or neprosin isolated from a *Nepenthes* plant).

The synthetic (e.g., recombinant) *Nepenthes* enzyme(s) can be concentrated or purified according to known methods, such as those for isolating *Nepenthes* enzyme(s) from the plant pitcher liquid.

In some embodiments, the protein product isolated from a natural source or a synthetic (e.g., recombinant) source comprises at least 20% by weight of at least one *Nepenthes* enzyme or a variant thereof. In some embodiments, the isolated protein product comprises at least about 50%, about 75%, about 90%, about 95% by weight of the *Nepenthes* enzyme or variant thereof. In some embodiments, the isolated protein product comprises at least 99% by weight of the *Nepenthes* enzyme or variant thereof.

In some embodiments, the recombinant *Nepenthes* enzyme or variant thereof comprises substantially only recombinant nepenthesin or variant thereof. In some embodiments, the recombinant nepenthesin or variant thereof comprises substantially only recombinant nepenthesin I or variant thereof. In some embodiments, the recombinant nepenthesin or variant thereof comprises substantially only nepenthesin II or variant thereof. In some embodiments, the recombinant nepenthesin or variant thereof comprises nepenthesin I and nepenthesin II, or variant thereof. In some embodiments, the recombinant nepenthesin or variant thereof comprises a ratio of nepenthesin I to nepenthesin II (or variant of each thereof) of at least about 100:1. In some embodiments, the recombinant nepenthesin comprises a ratio of nepenthesin I to nepenthesin II of at least about 90:1. In some embodiments, the recombinant nepenthesin comprises a ratio of nepenthesin I to nepenthesin II of at least about 70:1. In some embodiments, the recombinant nepenthesin comprises a ratio of nepenthesin I to nepenthesin II of at least about 60:1. In some embodiments, the recombinant nepenthesin comprises a ratio of nepenthesin I to nepenthesin II of at least about 50:1. In some embodiments, the recombinant nepenthesin comprises a ratio of nepenthesin I to nepenthesin II of at least about 40:1. In some embodiments, the recombinant nepenthesin comprises a ratio of nepenthesin I to nepenthesin II of at least about 30:1. In some embodiments, the recombinant nepenthesin comprises a ratio of nepenthesin I to nepenthesin II of at least about 20:1. In some embodiments, the recombinant nepenthesin comprises a ratio of nepenthesin I to nepenthesin II of at least about 10:1. In some embodiments, the recombinant nepenthesin comprises a ratio of nepenthesin I to nepenthesin II of at least about 5:1. In some embodiments, the recombinant nepenthesin comprises a ratio of nepenthesin I to nepenthesin II of at least about 4:1. In some embodiments, the recombinant nepenthesin comprises a ratio of nepenthesin I to nepenthesin II of at least about 3:1. In some embodiments, the recombinant nepenthesin comprises a ratio of nepenthesin I to nepenthesin II of at least about 2:1. In some embodiments, the recombinant nepenthesin comprises a ratio of nepenthesin I to nepenthesin II of at least about 1:1. In some embodiments, the recombinant nepenthesin comprises a ratio of nepenthesin I to nepenthesin II of at least about 1:2. In some embodiments, the recombinant nepenthesin comprises a ratio of nepenthesin I to nepenthesin II of at least about 1:3. In some embodiments, the recombinant nepenthesin comprises a ratio of nepenthesin I to nepenthesin II of at least about 1:4. In some embodiments, the recombinant nepenthesin comprises a ratio of nepenthesin I to nepenthesin II of at least about 1:5. In some embodiments, the recombinant nepenthesin comprises a ratio of nepenthesin I to nepenthesin II of at least about 1:10. In some embodiments, the recombinant nepenthesin comprises a ratio of nepenthesin I to nepenthesin II of at least about 1:20. In some embodiments, the recombinant nepenthesin comprises a ratio of nepenthesin I to nepenthesin II of at least about 1:30. In some embodiments, the recombinant nepenthesin comprises a ratio of nepenthesin I to nepenthesin II of at least about 1:40. In some embodiments, the recombinant nepenthesin comprises a ratio of nepenthesin I to nepenthesin II of at least about 1:50. In some embodiments, the recombinant nepenthesin comprises a ratio of nepenthesin I to nepenthesin II of at least about 1:60. In some embodiments, the recombinant nepenthesin comprises a ratio of nepenthesin I to nepenthesin II of at least about 1:70. In some embodiments, the recombinant nepenthesin comprises a ratio of nepenthesin I to nepenthesin II of at least about 1:80. In some embodiments, recombinant nepenthesin comprises a ratio of nepenthesin I to nepenthesin II of at least about 1:90. In some embodiments, the recombinant nepenthesin comprises a ratio of nepenthesin I to nepenthesin II of at least about 1:100.

In some embodiments, the recombinant *Nepenthes* enzyme or variant thereof comprises substantially only recombinant neprosin or variant thereof. In some embodiments, the recombinant *Nepenthes* enzyme or variant thereof comprises neprosin and nepenthesin or variant thereof. In some embodiments, the recombinant *Nepenthes* enzyme or variant thereof comprises neprosin and nepenthesin I or variant thereof. In some embodiments, the recombinant *Nepenthes* enzyme or variant thereof comprises neprosin and nepenthesin II or variant thereof. In some embodiments, the recombinant *Nepenthes* enzyme or variant thereof comprises neprosin, nepenthesin I and nepenthesin II, or variant thereof. In some embodiments, the recombinant *Nepenthes* enzyme or variant thereof comprises a ratio of neprosin to nepenthesin (or variant of each thereof) of at least about 100:1. In some embodiments, the recombinant *Nepenthes* enzyme comprises a ratio of neprosin to nepenthesin of at least about 90:1. In some embodiments, the recombinant *Nepenthes* enzyme comprises a ratio of neprosin to nepenthesin of at least about 70:1. In some embodiments, the recombinant *Nepenthes* enzyme comprises a ratio of neprosin to nepenthesin of at least about 60:1. In some embodiments, the recombinant *Nepenthes* enzyme comprises a ratio of neprosin to nepenthesin of at least about 50:1. In some embodiments, the recombinant *Nepenthes* enzyme comprises a ratio of neprosin to nepenthesin of at least about 40:1. In some embodiments, the recombinant *Nepenthes* enzyme comprises a ratio of neprosin to nepenthesin of at least about 30:1. In some embodiments, the recombinant *Nepenthes* enzyme comprises a ratio of neprosin to nepenthesin of at least about 20:1. In some embodiments, the recombinant *Nepenthes* enzyme comprises a ratio of neprosin to nepenthesin of at least about 10:1. In some embodiments, the recombinant *Nepenthes* enzyme comprises a ratio of neprosin to nepenthesin of at least about 5:1. In some embodiments, the recombinant *Nepenthes* enzyme comprises a ratio of neprosin to nepenthesin of at least about 4:1. In some embodiments, the recombinant *Nepenthes* enzyme comprises a ratio of neprosin to nepenthesin of at least about 3:1. In some embodiments, the recombinant *Nepenthes* enzyme comprises a ratio of neprosin to nepenthesin of at least about 2:1. In some embodiments, the recombinant *Nepenthes* enzyme comprises a ratio of neprosin to nepenthesin of at least about 1:1. In some embodiments, the recombinant *Nepenthes* enzyme comprises a ratio of neprosin to nepenthesin of at least about 1:2. In some embodiments, the recombinant *Nepenthes* enzyme comprises a ratio of neprosin to nepenthesin of at least about 1:3. In some embodiments, the recombinant *Nepenthes* enzyme comprises a ratio of neprosin to nepenthesin of at least about 1:4. In some embodiments, the recombinant *Nepenthes* enzyme comprises a ratio of neprosin to nepenthesin of at least about 1:5. In some embodiments, the recombinant *Nepenthes* enzyme comprises a ratio of neprosin to nepenthesin of at least about 1:10. In some embodiments, the recombinant *Nepenthes* enzyme comprises a ratio of neprosin to nepenthesin of at least about 1:20. In some embodiments, the recombinant *Nepenthes* enzyme comprises a ratio of neprosin to nepenthesin of at least about 1:30. In some embodiments, the recombinant *Nepenthes* enzyme comprises a ratio of neprosin to nepenthesin of at least about 1:40. In some embodiments, the recombinant *Nepenthes* enzyme comprises a ratio of neprosin to nepenthesin of at least about 1:50. In some embodiments, the recombinant *Nepenthes* enzyme comprises a ratio of neprosin to nepenthesin of at least about 1:60. In some embodiments, the recombinant *Nepenthes* enzyme comprises a ratio of neprosin to nepenthesin of at least about 1:70. In some embodiments, the recombinant *Nepenthes* enzyme comprises a ratio of neprosin to nepenthesin of at least about 1:80. In some embodiments, recombinant *Nepenthes* enzyme comprises a ratio of neprosin to nepenthesin of at least about 1:90. In some embodiments, the recombinant *Nepenthes* enzyme comprises a ratio of neprosin to nepenthesin of at least about 1:100.

In some embodiments, the protein product isolated from a natural source or a synthetic source comprises an amino acid that is at least about 70% homologous to the amino acid sequence of *Nepenthes* nepenthesin I (e.g., SEQ ID NO.: 5; SEQ ID NO.: 6; SEQ ID NO.: 7; SEQ ID NO.: 21). In one embodiment, the protein product retains protease activity. The protein may be at least about 80% homologous to *Nepenthes* nepenthesin I. The protein may be at least about 85% homologous to *Nepenthes* nepenthesin I. The protein may be at least about 90% homologous to *Nepenthes* nepenthesin I. The protein may be at least about 95% homologous to *Nepenthes* nepenthesin I. The protein may be at least about 96% homologous to *Nepenthes* nepenthesin I. The protein may be at least about 97% homologous to *Nepenthes* nepenthesin I. The protein may be at least about 98% homologous to *Nepenthes* nepenthesin I. The protein may be at least about 99% homologous to *Nepenthes* nepenthesin I.

In some embodiments, the protein product isolated from a natural source or a synthetic source comprises a protein that is at least about 70% homologous to *Nepenthes* nepenthesin II (e.g., SEQ ID NO.: 8; SEQ ID NO.: 9; SEQ ID NO.: 20). In one embodiment, the protein product retains protease activity. The protein may be at least about 80% homologous to *Nepenthes* nepenthesin II. The protein may be at least about 85% homologous to *Nepenthes* nepenthesin II. The protein may be at least about 90% homologous to *Nepenthes* nepenthesin II. The protein may be at least about 95% homologous to *Nepenthes* nepenthesin II. The protein may be at least about 96% homologous to *Nepenthes* nepenthesin II. The protein may be at least about 97% homologous to *Nepenthes* nepenthesin II. The protein may be at least about 98% homologous to *Nepenthes* nepenthesin II. The protein may be at least about 99% homologous to *Nepenthes* nepenthesin II.

In some embodiments, the protein product isolated from a natural source or a synthetic source comprises a protein that is at least about 70% homologous to *Nepenthes* neprosin (e.g., SEQ ID NO.: 1). In one embodiment, the protein product retains protease activity. The protein may be at least about 80% homologous to *Nepenthes* neprosin. The protein may be at least about 85% homologous to *Nepenthes* neprosin. The protein may be at least about 90% homologous to *Nepenthes* neprosin. The protein may be at least about 95% homologous to *Nepenthes* neprosin. The protein may be at least about 96% homologous to *Nepenthes* neprosin. The protein may be at least about 97% homologous to *Nepenthes* neprosin. The protein may be at least about 98% homologous to *Nepenthes* neprosin. The protein may be at least about 99% homologous to *Nepenthes* neprosin.

In some embodiments, the protein product isolated from a natural source or a synthetic source comprises nepenthesin or a variant thereof with at least about 10% of the original protease activity of *Nepenthes* nepenthesin I. In some embodiments, the protein product comprises nepenthesin or a variant thereof with at least about 20% of the original protease activity of nepenthesin I. In some embodiments, the protein product comprises nepenthesin or a variant thereof with at least about 30% of the original protease activity of nepenthesin I. In some embodiments, the protein product comprises nepenthesin or a variant thereof with at least about 40% of the original protease activity of nepenthesin I. In some embodiments, the protein product comprises nepenthesin or a variant thereof with at least about 50% of the original protease activity of nepenthesin I. In some embodiments, the protein product comprises nepenthesin or a variant thereof with at least about 60% of the original protease activity of nepenthesin I. In some embodiments, the protein product comprises nepenthesin or a variant thereof with at least about 70% of the original protease activity of nepenthesin I. In some embodiments, the protein product comprises nepenthesin or a variant thereof with at least about 80% of the original protease activity of nepenthesin I. In some embodiments, the protein product comprises nepenthesin or a variant thereof with at least about 90% of the original protease activity of nepenthesin I. In some embodiments, the protein product comprises nepenthesin or a variant thereof with greater than about 100% of the original protease activity of nepenthesin I.

In some embodiments, the protein product isolated from a natural source or a synthetic source comprises nepenthesin or a variant thereof with at least about 10% of the original protease activity of *Nepenthes* nepenthesin II. In some embodiments, the protein product comprises nepenthesin or a variant thereof with at least about 20% of the original protease activity of nepenthesin II. In some embodiments, the protein product comprises nepenthesin or a variant thereof with at least about 30% of the original protease activity of nepenthesin II. In some embodiments, the protein product comprises nepenthesin or a variant thereof with at least about 40% of the original protease activity of nepenthesin II. In some embodiments, the protein product comprises nepenthesin or a variant thereof with at least about 50% of the original protease activity of nepenthesin II. In some embodiments, the protein product comprises nepenthesin or a variant thereof with at least about 60% of the original protease activity of nepenthesin II. In some embodiments, the protein product comprises nepenthesin or a variant thereof with at least about 70% of the original protease activity of nepenthesin II. In some embodiments, the protein product comprises nepenthesin or a variant thereof with at least about 80% of the original protease activity of nepenthesin II. In some embodiments, the protein product comprises nepenthesin or a variant thereof with at least about 90% of the original protease activity of nepenthesin II. In some embodiments, the protein product comprises nepenthesin or a variant thereof with greater than about 100% of the original protease activity of nepenthesin II.

In some embodiments, the protein product isolated from a natural source or a synthetic source comprises neprosin or a variant thereof with at least about 10% of the original protease activity of *Nepenthes* neprosin. In some embodiments, the protein product comprises neprosin or a variant thereof with at least about 20% of the original protease activity of neprosin. In some embodiments, the protein product comprises neprosin or a variant thereof with at least about 30% of the original protease activity of neprosin. In some embodiments, the protein product comprises neprosin or a variant thereof with at least about 40% of the original protease activity of neprosin. In some embodiments, the protein product comprises neprosin or a variant thereof with at least about 50% of the original protease activity of neprosin. In some embodiments, the protein product comprises neprosin or a variant thereof with at least about 60% of the original protease activity of neprosin. In some embodiments, the protein product comprises neprosin or a variant thereof with at least about 70% of the original protease activity of neprosin. In some embodiments, the protein product comprises neprosin or a variant thereof with at least about 80% of the original protease activity of neprosin. In some embodiments, the protein product comprises neprosin or a variant thereof with at least about 90% of the original protease activity of neprosin. In some embodiments, the protein product comprises neprosin or a variant thereof with greater than about 100% of the original protease activity of neprosin.

Unless stated otherwise, the abbreviations used throughout the specification have the following meanings:
g=gram
kDa=kiloDalton
kg=kilogram
L=liter
LC=liquid chromatography
mg=milligram
min=minute
mL=milliliter
mM=millimolar
MS=mass spectrometry
nM=nanomolar
pM=picomolar
s.d.=standard deviation
µCi=microcurie
µg microgram
µL=microliter
µM=micromolar
µm=micrometer
° C.=degree Celsius These one-letter symbols have the following meaning when representing amino acids:
A=Alanine
R=Arginine
N=Asparagine D=Aspartic acid
C=Cysteine
E=Glutamic acid
Q=Glutamine
G=Glycine
H=Histidine
I=Isoleucine
L=Leucine
K=Lysine
M=Methionine
F=Phenylalanine
P=Proline
S=Serine
T=Threonine
W=Tryptophan
Y=Tyrosine
V=Valine

EXAMPLES

Example 1. Nepenthesin Extract Preparation

Chemicals

Water and acetonitrile, HPLC grade form Burdick and Jackson, were purchased from VWR. Formic acid, Tris, and glycine were purchased from Sigma Aldrich.

Plant Culture

Transplants of *Nepenthes rafflesiana, Nepenthes ampularia, Nepenthes mirabilis,* and *Nepenthes globosa* were purchased from Keehns Carnivores (www.keehnscarnivores.ca). These were potted with wood bark, perlite, peat moss and humus (40, 35, 10, 5% respectively). Growth conditions involved 14 hours of light per day, 80% humidity and temperature in the 23° C. to 28° C. range with 2 to 3 waterings a week. Upon pitcher maturity, plants were fed with one or two *Drosophila* per pitcher and the pitcher fluid harvested one week later. Pitchers and their secretions were left to recover for one week prior to a second round of feeding and extraction.

Extract Preparation

Pitcher fluid was collected from all four species of plants and combined. The crude pitcher fluid was first clarified through a 0.22 µm filter, then concentrated 80 to 100 fold using an Amicon Ultra centrifugal 10 kDa molecular weight cut-off filter (both from Millipore). Prior to use in digestions, the concentrate was acid-activated with 100 mM Glycine HCl (pH 2.5) for 3 hours, then washed 3× with 100 mM Glycine-HCl (pH 2.5) in the filtration device, using 10× fluid volume for each wash. The final isolate was then rediluted to an 11× concentration based on the original sampling of pitcher fluid.

Characterization of Pitcher Fluid Extract

The fluidic secretions of the pitcher plant were concentrated and the digestion enzymes activated by pH reduction (pH 2.5). The impact of the enrichment process and the activation on the fluid proteome was determined using proteomics methods. First, to confirm the presence of nepenthesin enzyme, the inactive concentrate was separated by SDS-PAGE. Seven contiguous gel zones with very faint coomassie staining were digested with trypsin and analyzed by nanoLC-MS/MS using standard methods. This is not expected to be a complete catalog of the activated fluid proteome, but the analysis confirmed the presence of the aspartic protease nepenthesin I/II, as well as a glucanase, chitinase, carboxypeptidase and peroxidase of plant origin, plus modest levels of *drosophila* and bacterial contamination. The low complexity of the fluid proteome is consistent with recent analyses, Hatano N, Hamada T (2012) Proteomic analysis of secreted protein induced by a component of prey in pitcher fluid of the carnivorous plant *Nepenthes alata. Journal of Proteomics* 3; 75(15):4844-52 (Epub Jun. 15, 2012), but nepenthesin-I was found distributed over a much wider mass range in this analysis (40-70 kDa).

The acid-activated fluid was then processed and analyzed in a similar fashion. The activation process reduced the overall protein yield, and also appeared to simplify the composition. Aside from nepenthesin-I, only minor contamination from keratin and actin were in evidence. These analyses point to the low complexity of the enriched fluid, where nepenthesin is the major component. The total protein concentration of the activated and 80× enriched fluid was measured by a BCA assay to be 22 ng/µL. This value is consistent with an earlier study describing enrichment of the fluid. Tokes Z A, et al., Digestive Enzymes Secreted by Carnivorous Plant *Nepenthes*-Macferlanei-L. *Planta* 119(1): 39-46 (1974).

Example 2: Nepenthesin Extract Purification

Purification of Extract

Sepharose-immobilized pepstatin in a 50×2 cm ID column was equilibrated in 20 mM Glycine-HCl, pH 2.5-3. The filtered pitcher fluid (prepared as described in Example 1) was cycled twice through the column, and the column washed with 100 mL equilibration buffer (20 mM glycine HCl, pH 2.5). The column was eluted with 100 mM ammonium bicarbonate pH 8.7 and fractions collected. In order to preserve maximum the enzyme activity, the pH was decreased to 4 right after fraction collection with 2 M glycine HCl, pH 2.5. Activity was verified using a digestion assay, and the most active fractions combined and concentrated to approximately 80×, based on original fluid volume.

The only endoproteases found at detectable levels in the *Nepenthes* fluid and/or extract are aspartic proteases and prolyl endoprotease.

Example 3: Recombinant Nepenthesin I

The gene for nepenthesin I (SEQ ID NO: 4; encoding amino acid residues 20-413, from *N. gracilis*, without the plant signal sequence) was prepared from nepenthesin I cDNA, and placed between NdeI and HindIII restriction sites. This sequence was cloned into pET21a, using T4 DNA ligase (1 U) (New England Bio, NEB), T4 DNA ligase buffer (NEB), ATP (0.5 mM) (NEB), 0.5 µg pET21a vector and 2 µg of the nepenthesin I cDNA. This was incubated at 18° C. for 4 hours. The ligation mixture (5 µL) was added to 200 µL of NovaBlue competent cells and incubated on ice for 15 minutes. Cells were transformed by heat shock (45 seconds at 42° C., then immediately on ice, with 1 ml of LB medium) and incubated for 1 hour at 37° C., and plated with antibiotics (tetracycline and ampicillin). After confirming gene presence in several white colonies, a representative colony was chosen for maxiprep. The resulting recombinant plasmid pET21a/R.NepI was transformed into *E. coli* C41 by heat-shock as above, for expression under induction by IPTG. Here, cells were grown up to an $OD_{660}$ of 0.6 and induced with 0.1 mM IPTG for four hours at 37° C. The expressed protein went to inclusion bodies.

Inclusion bodies were isolated as follows. Cells were centrifuged, sucrose lysis buffer was added (25% saccharose, 50 mM TrisCl pH 7.4, 1 mM EDTA, 1 mM $NaN_3$, and protease inhibitors), and the cells were subjected to four rounds of freeze/thaw and sonication. This was followed by the addition of DNAse and RNAse for a 30 min. incubation at room temperature. The preparation was centrifuged (~15 min. at 5000×g) to pellet the inclusion bodies and membrane fragments. This pellet was resuspended in Triton buffer (50 mM TrisCl pH 7.4, 10 mM NaCl, 1 mM β-mercaptoethanol, 1 mM NaN$_3$, 0.5% Triton X100+protease inhibitors) and sonication performed on ice. This was once again centrifuged, to pellet the inclusion bodies, and the pellet was washed twice on ice (with mixing and sonication) in a buffer free of Triton (50 mM TrisCl pH 7.4, 10 mM NaCl, 1 mM β-mercaptoethanol, 1 mM NaN$_3$, protease inhibitors).

The protein pellet was then subjected to refolding. One g of inclusion bodies was suspended into 1 L of 50 mM CAPS pH 10.5, 8 M urea, 1 mM EDTA, 1 mM glycine, 500 mM NaCl, 300 mM β-mercaptoethanol and shaken for 1 hr. The suspension was dialysed against 50 mM Tris, pH 11, twice for 1 hour at a time, followed by one day of dialysis against 50 mM Tris, pH 7.5, and finally, dialysis against phosphate buffer with 300 mM NaCl, pH 7.0.

The solution was centrifuged at high speed (10000×g for 15 min.) to remove any un-refolded protein, and the supernatant filtered through a 0.22 µm membrane. Nepenthesin I was activated at pH 2.5 (glycine-HCl) overnight at 4° C. Yields range from 10 to 100 mg of folded, activated protein, starting from 1 L of cell culture.

Example 4: Recombinant Nepenthesin II

The cDNA of nepenthesin II (see SEQ ID NO.: 14) from *N. gracilis*, without the plant signal sequence) was used to prepare nepenthesin II cDNA. This sequence was cloned into pET21a between NdeI and HindIII restriction sites, using T4 DNA ligase (1 U) (New England Bio, NEB), T4 DNA ligase buffer (NEB), ATP (0.5 mM) (NEB), 0.5 µg pET21a vector and 2 µg of the nepenthesin II cDNA. This was incubated at 18° C. for 4 hours. The ligation mixture (5 µL) was added to 200 µL of NovaBlue competent cells and incubated on ice for 15 minutes. Cells were transformed by heat shock (45 seconds at 42° C., then immediately on ice, with 1 ml of LB medium) and incubated for 1 hour at 37° C., and plated with antibiotics (tetracycline and ampicillin). After confirming gene presence in several white colonies, a representative colony was chosen for maxiprep. The resulting recombinant plasmid pET21a/R.NepI was transformed into *E. coli* C41 by heat-shock as above, for expression under induction by IPTG. Here, cells were grown up to an OD$_{660}$ of 0.6 and induced with 0.1 mM IPTG for four hours at 37° C. The expressed protein went to inclusion bodies.

Inclusion bodies were isolated as follows. Cells were centrifuged, sucrose lysis buffer was added (25% saccharose, 50 mM TrisCl pH 7.4, 1 mM EDTA, 1 mM NaN$_3$, and protease inhibitors), and the cells were subjected to four rounds of freeze/thaw and sonication. This was followed by the addition of DNAse and RNAse for a 30 min. incubation at room temperature. The preparation was centrifuged (~15 min. at 5000×g) to pellet the inclusion bodies and membrane fragments. This pellet was resuspended in Triton buffer (50 mM TrisCl pH 7.4, 10 mM NaCl, 1 mM β-mercaptoethanol, 1 mM NaN$_3$, 0.5% Triton X100+protease inhibitors) and sonication performed on ice. This was once again centrifuged, to pellet the inclusion bodies, and the pellet was washed twice on ice (with mixing and sonication) in a buffer free of Triton (50 mM TrisCl pH 7.4, 10 mM NaCl, 1 mM β-mercaptoethanol, 1 mM NaN$_3$, protease inhibitors).

The protein pellet was then subjected to refolding. One g of inclusion bodies was suspended into 1 L of 50 mM CAPS pH 10.5, 8 M urea, 1 mM EDTA, 1 mM glycine, 500 mM NaCl, 300 mM β-mercaptoethanol and shaken for 1 hr. The suspension was dialysed against 50 mM Tris pH 11 twice for 1 hour at a time, followed by one day of dialysis against 50 mM Tris pH 7.5, and finally, dialysis against phosphate buffer with 300 mM NaCl, pH 7.0.

The solution was centrifuged at high speed (10000×g for 15 min.) to remove any un-refolded protein, and the supernatant filtered through a 0.22 µm membrane. Nepenthesin II was activated at pH 2.5 (glycine-HCl) overnight at 4° C. Yields range from 10 to 100 mg of folded, activated protein, starting from 1 L of cell culture.

Example 5. Glycosylation of *Nepenthes* Enzymes

Recombinant production of nepenthesin I (A) and II (C) from refolding of purified *E. coli* inclusion bodies is shown in FIG. 2. Each step of the refolding procedure was monitored and is shown as: total solubilized protein from purified *E. coli* inclusion bodies (Lane 1), refolded nepenthesin after final dialysis (lane 2), 24-hour acid activation (100 mM glycine-HCl, pH 2.5) of refolded product (lane 3). MALDI-TOF MS analysis was performed on the 24-hour acid activated nepenthesin I (B) and II (D) enzymes. LC-MS/MS analyses of in-gel digests of the acid-activated bands (A and C, lanes 3) confirmed the presence of pure nepenthesin I and II respectively.

Figure 3:
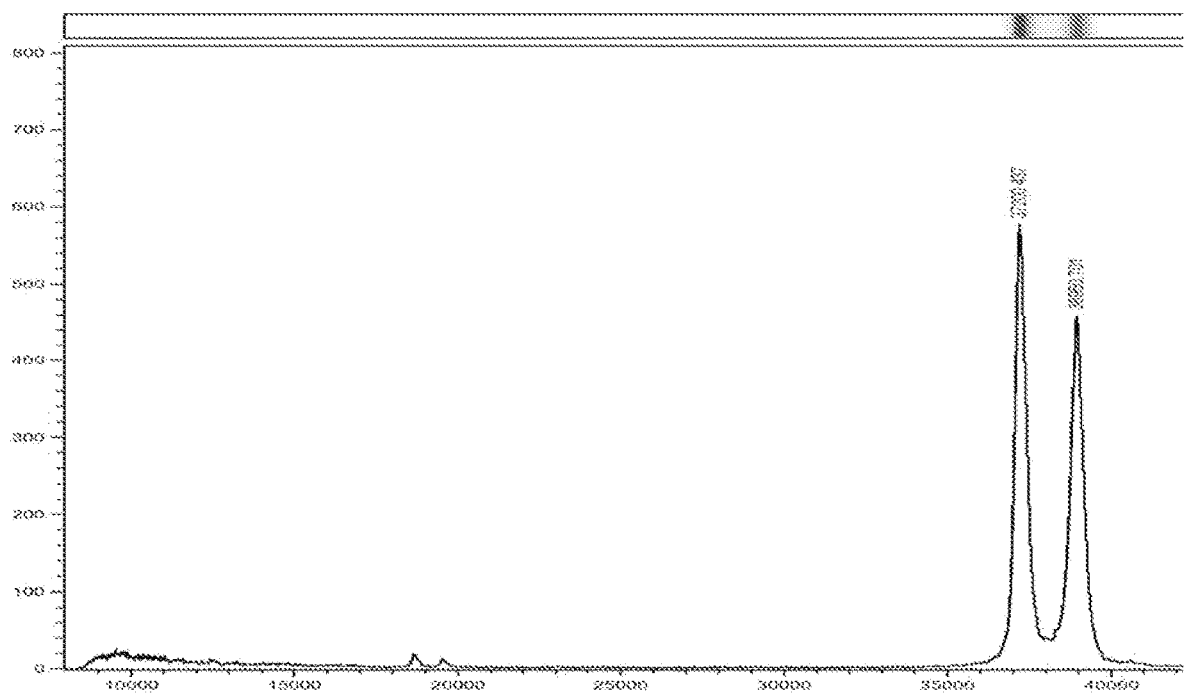
FIG. 3 indicates the sizes of natural nepenthesin I and nepenthesin II (pooled from 2-3 species) by MALDI-TOF MS.

MALDI-TOF analyses of natural nepenthesins (pooled from 2-3 species) was performed. Results are shown in FIG. 3. The mass at 37,200 is believed to be nepenthesin II and the mass at 38,951 to be nepenthesin I. Either way, they are different than the masses of the recombinant enzymes, as shown in Table 1.

TABLE 1

Mass of Recombinant v. Natural Nepenthesins

| Nepenthesin 1 | Mass (Daltons)* | Nepenthesin II | Mass (Daltons)* |
|---|---|---|---|
| recombinant | 37,460 | recombinant | 37,506 |
| natural | 38,949 | natural | 37,199 |
| Difference: | 1,489 | | −307 |

*1 Dalton is subtracted for the proton added by MALDI.

Without being bound by theory, we believe that this confirms nepenthesin I is glycosylated in nature. The active, mature enzyme of recombinant nepenthesin II is larger than what exists in nature. It remains possible that natural nepenthesin II is even smaller in protein sequence but has some minor glycosyation. The masses of the natural enzymes reported herein differ from Athauda et al. likely because mass spec is a more accurate technique than SDS PAGE for determining the mass of a molecule.

Example 6. Comparison of *Nepenthes* Enzymes with Pepsin

Figure 4:
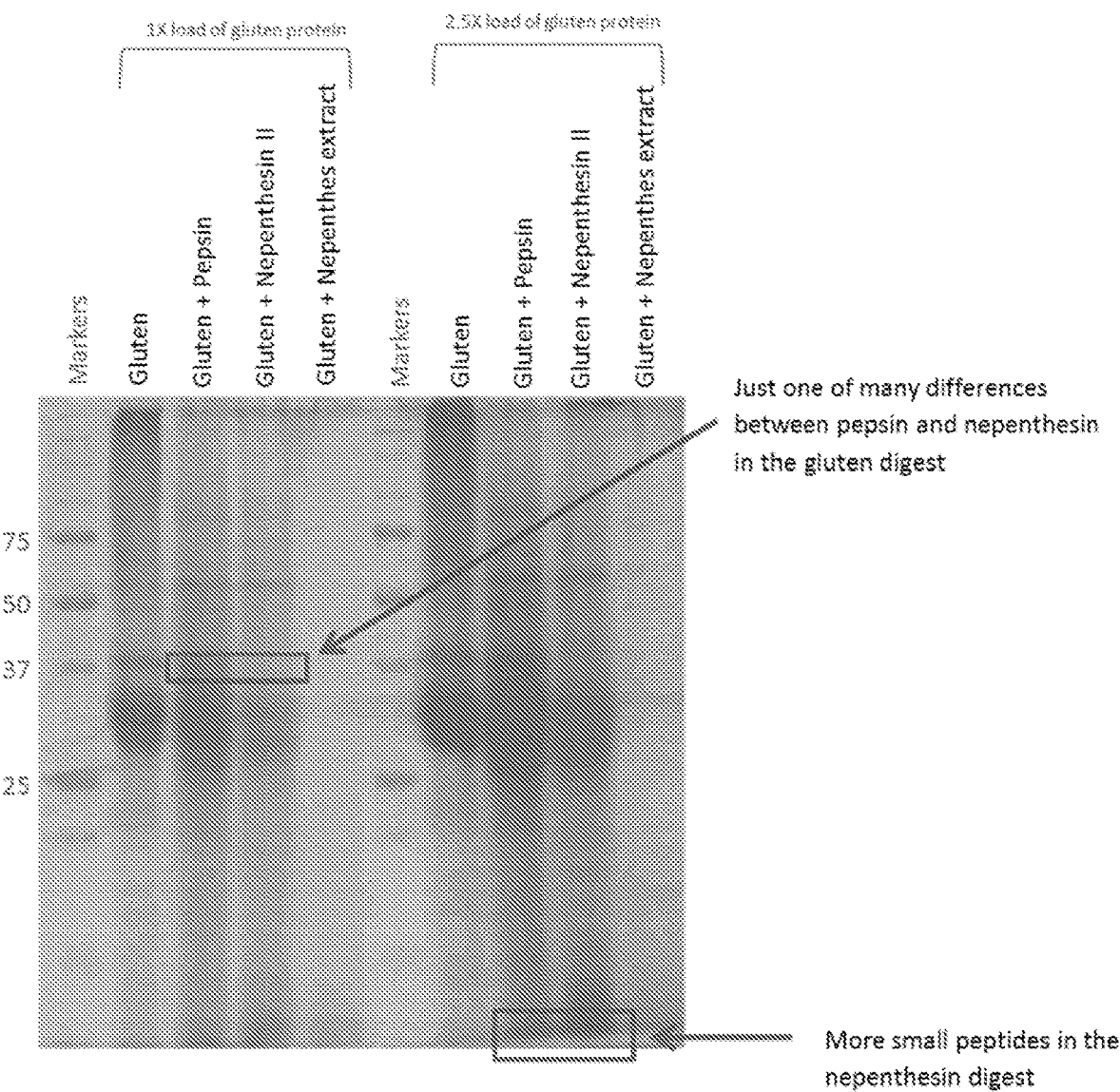
FIG. 4 is a photograph of a Coomassie-stained gel SDS-PAGE gel indicating the molecular weights of gluten fragments after digestion with recombinant nepenthesin II, *Nepenthes* extract, or pepsin.

SDS-PAGE was performed on gliadin digested by the indicated enzyme. SDS-PAGE roughly profiles proteins according to molecular weight. Gliadin digestion with pepsin, purified *Nepenthes* extract, or recombinant nepenthesin II was performed at a substrate to enzyme ratio of approximately 100:1. Gliadin (5 mg) was incubated with the indicated preparation at 37° C. for 2 hr. FIG. 4 shows an SDS-PAGE gel of gliadin digestion by recombinant nepenthesin II, *Nepenthes* extract, or pepsin. The gel shows that digestion of gliadin by recombinant nepenthesin II results in a different digestion pattern and digestion into smaller peptides than does pepsin. This is particularly noticeable in the boxed areas of the gel. *Nepenthes* extract is so efficient at degrading gliadin that no residual gliadin protein is observed in this region.

Table 2 indicates preferred, low probability, and forbidden residues for C-terminal cleavage by pepsin, recombinant nepenthesin I and II, and *Nepenthes* extract. C-terminal cleavage specificity, the classic way enzymes are classified, is summarized based on a large collection of protein substrates. The nepenthesins are quite different from pepsin in cleavage specificity, indicating that nepenthesin and pepsin are very different enzymes. The pepsin data provided in Table 2 is summarized from the literature (e.g. "Determining the Specificity of Pepsin for Proteolytic Digestion", a thesis by Melissa Palashoff available at: books.google.ca/books?id=7O1nU4-6T-wC&printsec=frontcover#v=onepage&q&f=false). *Nepenthes* enzyme data is summarized from digestions studies such as that described in U.S. Patent Application Publication No. 2014/0186330, which is incorporated herein by reference in its entirety.

TABLE 2

C-terminal Cleavage

|  | Pepsin | Nepenthesin I and II | *Nepenthes* extract |
| --- | --- | --- | --- |
| Preferred | F, L, M | F, L, M, K, R, D, E, C, Y, A | F, L, M, K, R, D, E, C, Y |
| Low probability | W, C, Y, D, E, G, Q, N, S, T | W, G, N, Q, V, T | H, I, A, P, N, Q |
| "Forbidden" | I, V, K, R, P, H, G | G, I, S, P | G, S, T, W, V |

LC-MS assay was performed to determine the ability of each enzyme to cleave the 33-mer toxic gluten peptide. 33-mer was incubated with the indicated enzyme for 0.5 h at a 100:1 ratio (substrate:enzyme), and the amount of undigested 33-mer determined relative to a standard, following common practice. Data is provided as percent of the control (33-mer with no enzyme added).

Table 3 provides the digestion of the pepsin-resistant fragment from gluten protein that is called the "33-mer" (LQLQPFPQPQLPYPQPQLPYPQPQLPYPQPQPF) SEQ ID. 15. This sequence is strongly linked to celiac disease and is often termed a toxic gluten peptide. Like the whole gluten proteins themselves, the 33-mer is rich in Q, P and L amino acids. Extended digestion times using just pepsin did not have much of an effect on this peptide—it was very resistant to pepsin digestion. In contrast, nepenthesin I, nepenthesin II and the high molecular weight fraction (>approx. 10 kDa) of *Nepenthes* extract (fluid) exhibited the ability to digest this peptide. Data are provided as % of control (33-mer with no enzyme).

TABLE 3

33-mer Digestion

| Enzyme for Digestion | Relative Peak Area (%) |
| --- | --- |
| Control | 100.0 |
| *Nepenthes* fluid | 0.0 |
| Nepenthesin I | 78.7 |
| Nepenthesin II | 34.0 |
| Pepsin | 93.2 |

Figure 5A:
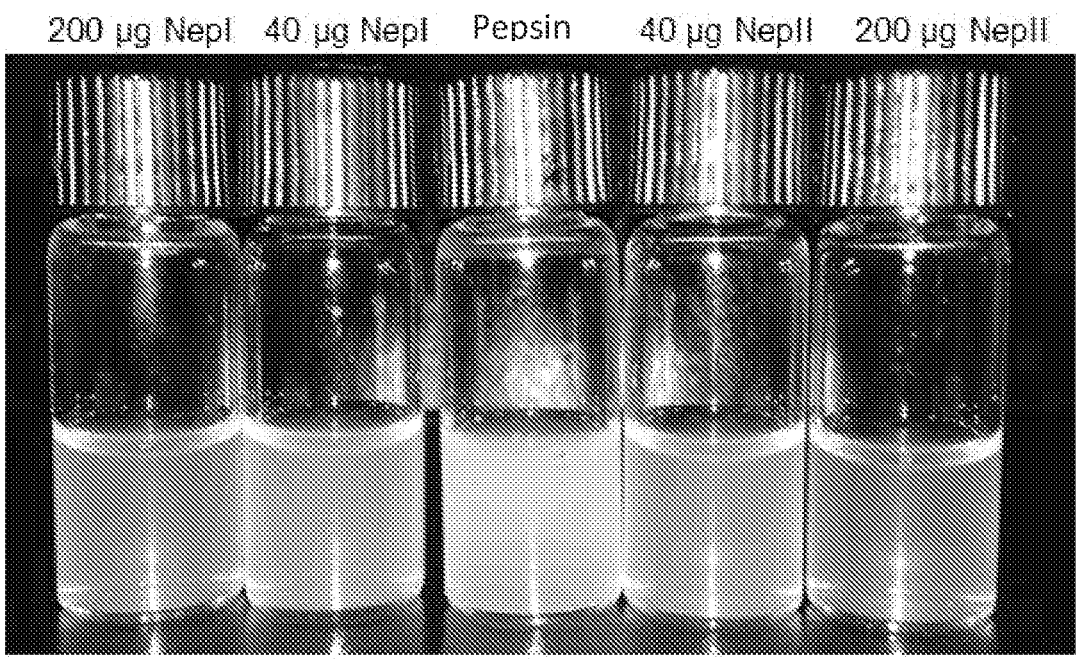
FIG. 5A is a photograph of vials containing a slurry of gluten protein digested with pepsin (40 µg) or the indicated amount of recombinant nepenthesin I or recombinant nepenthesin II.
Figure 5B:
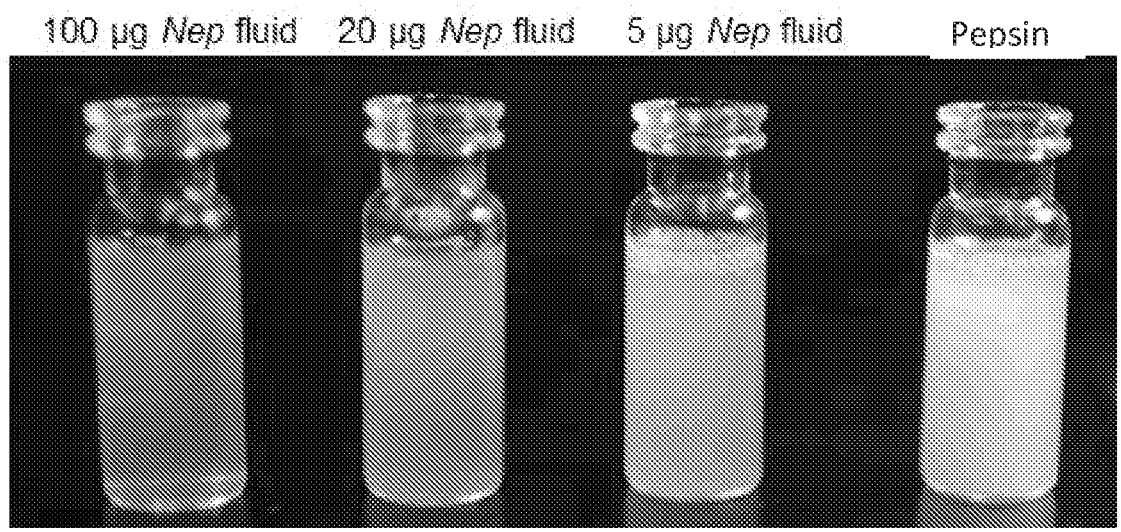
FIG. 5B is a photograph of vials containing a slurry of gluten protein digested with pepsin (40 µg) or the indicated amount of *Nepenthes* extract. The vials incubated with nepenthesin or *Nepenthes* extract are less cloudy than the pepsin vial, showing more vigorous digestion of gluten.

Gliadin protein slurry (5 mg gluten) was incubated with 40 or 200 µg of recombinant nepenthesin I or recombinant nepenthesin II, or 40 µg of pepsin and examined for degree of digestion (as determined by the degree of cloudiness of the relative solutions). Increasing amounts of pepsin have no effect on the cloudiness of the slurry (data not shown). FIG. 5A is an image of vials containing gliadin slurry and the indicated amount of recombinant nepenthesin I, recombinant nepenthesin II, or pepsin. FIG. 5B is similar, but used 5, 20, or 100 µg of *Nepenthes* extract. The vials incubated with nepenthesin or *Nepenthes* extract were less cloudy than the pepsin vial, showing more vigorous digestion of gliadin.

These data show that the gliadin protein digests are different between *Nepenthes* enzymes and pepsin at the gel level (which shows the "larger" digestion products), the peptide level (processing of the 33-mer), and at the slurry level (clarifying the solution). Pepsin, neprosin, and nepenthesin are very different proteins with distinct cleavage specificities, particularly with regard to gluten proteins. Simply put, pepsin does not adequately digest gluten in a manner to avoid gluten toxicity whereas the *Nepenthes* enzymes do.

Example 7. Digestion of Gliadin by *Nepenthes* Extract

Digestions of gliadin by nepenthesin were performed in solution using a LEAP HTX-PAL autosampler and dispensing system designed for hydrogen/deuterium exchange (HDX) applications. Data were collected using an AB Sciex Triple-TOF 5600 QqTOF mass spectrometer. Peptides were identified using Mascot (v2.3) from MS/MS data. Briefly, 12 pmol of crude gliadin (purchased from Sigma Aldrich) were mixed with 2 µL of 100× concentrated extract, produced as described in Example 1. After digestion the entire volume was injected into a reversed-phase LC system connected to the mass spectrometer. The peptides were trapped on a 7 cm, 150 µm i.d. Magic C18 column and eluted with an acetonitrile gradient from 10% to 40% in 10 or 30 minutes. Peptides detected in these analyses were selected for CID fragmentation in multiple information-dependent acquisitions of MS/MS spectra. Spectra were searched against a miniature database containing the sequences for all identified wheat gliadin (α, β, γ, ω) proteins plus the low and high molecular weight glutenin.

Figure 6:
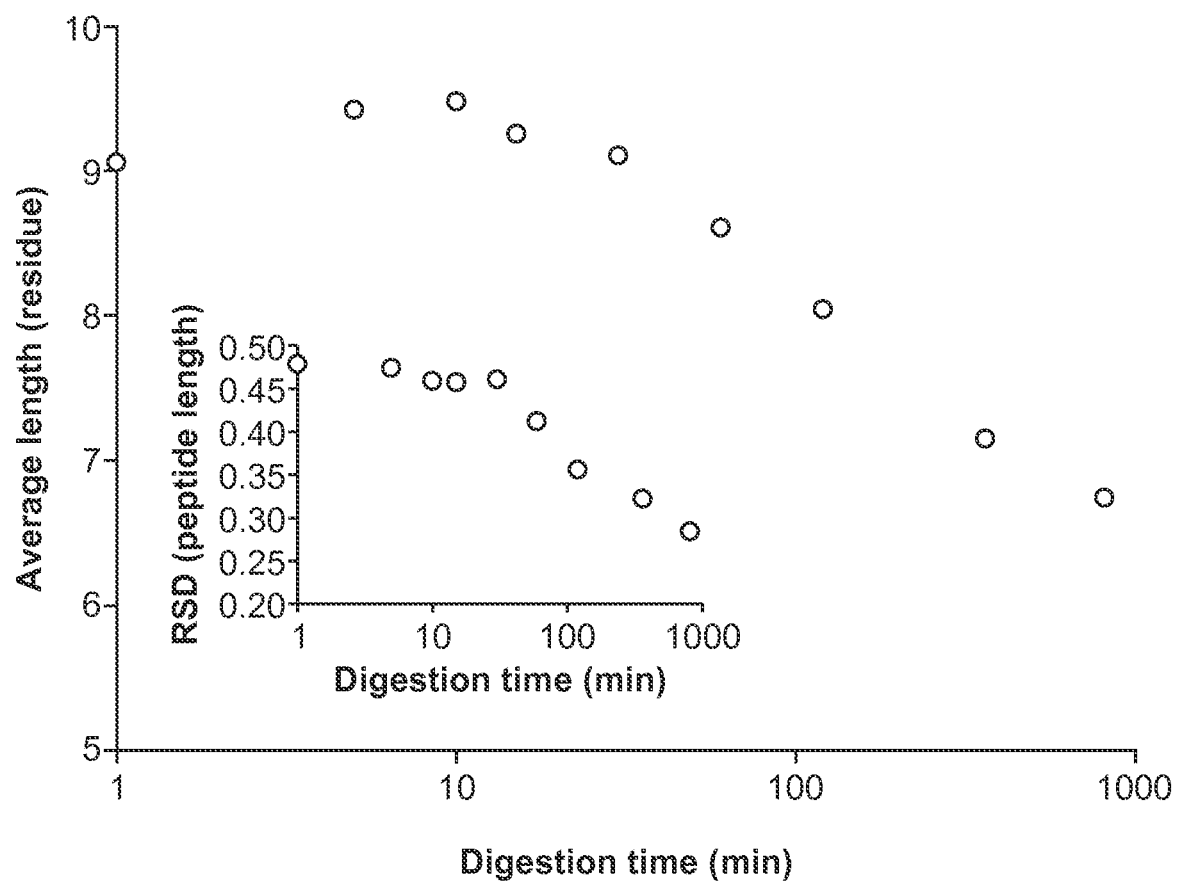
FIG. 6 shows the average length of all peptides identified from digestion of gliadin from wheat with enriched *Nepenthes* fluid, using LC-MS/MS, after 1, 5, 10, 15, 30, 60, 130, 360 or 810 minutes at 37° C. A 95% confidence cut-off ($p<0.05$) on the scores were used to REDUCE false positive identification. Relative standard deviation of the peptide length is shown in the inset figure.

FIG. 6 shows the average length of all peptides identified from the *nepenthes* extract digestion of gliadin from wheat, using LC-MS/MS, after 1, 5, 10, 15, 30, 60, 130, 360 or 810 minutes at 37° C. A 95% confidence cut-off (p<0.05) on the scores were used to reduce false positive identifications. Relative standard deviation of the peptide length is shown in the inset figure.

Figure 7:
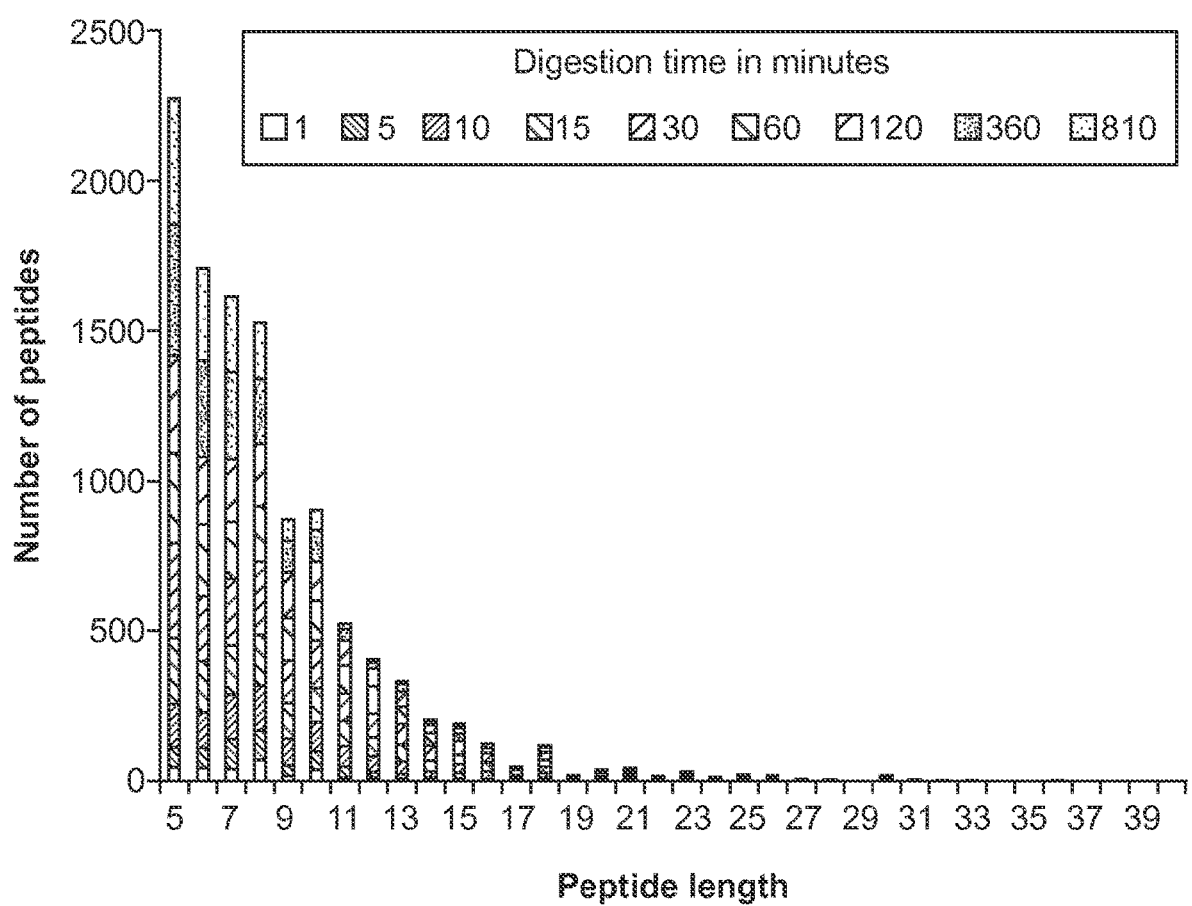
FIG. 7 displays the number of peptides identified by LC-MS/MS after 1, 5, 10, 15, 30, 60, 130, 360 or 810 minutes digestion at 37° C., grouped by length. Data as in FIG. 6.

FIG. 7 displays the number of peptides identified by LC-MS/MS after 1, 5, 10, 15, 30, 60, 130, 360 or 810 minutes digestion at 37° C., grouped by length. Data as in FIG. 6.

Figure 8:
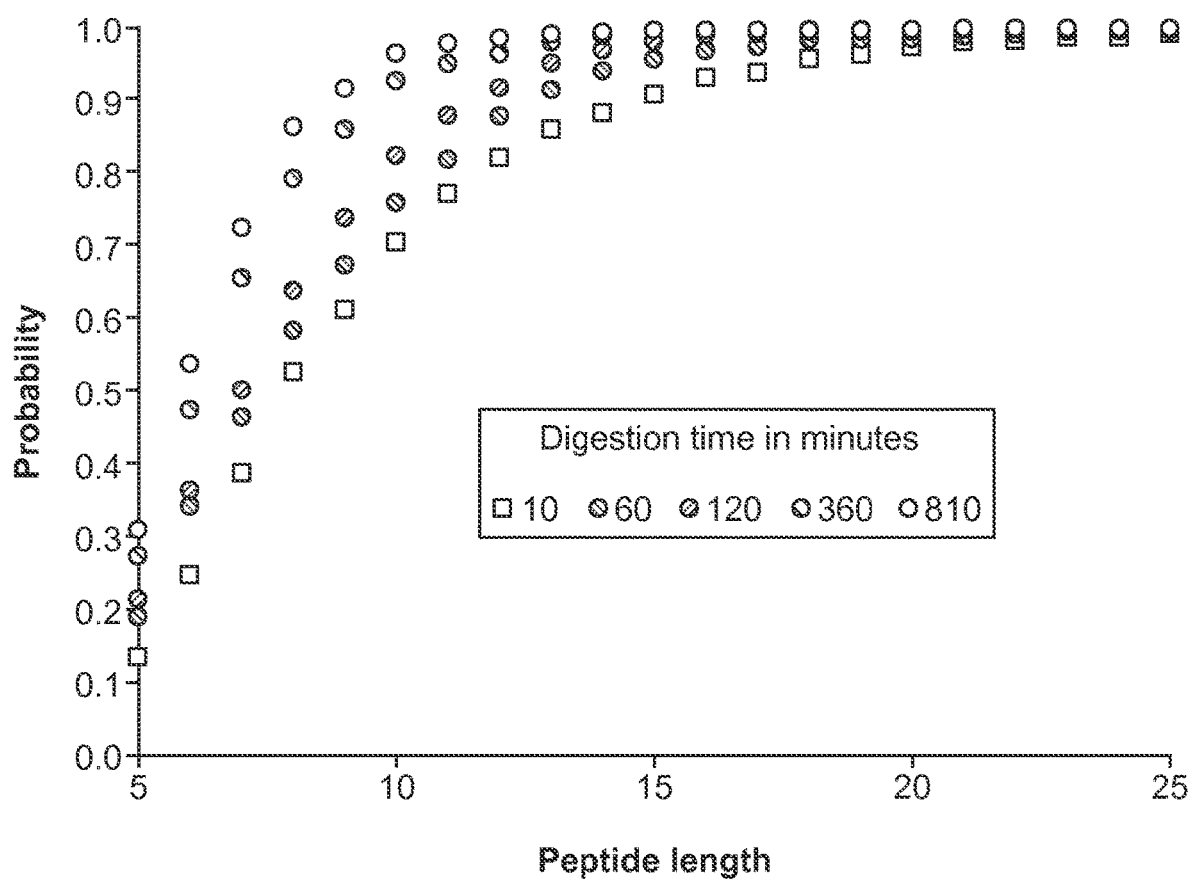
FIG. 8 displays the same data as in FIG. 6, as a cumulative probability of obtaining a certain length after 10, 60, 120, 360 or 810 minutes digestion at 37° C.

FIG. 8 displays the same data as in FIG. 6, as a probability of obtaining a certain length after 10, 60, 120, 360 or 810 minutes digestion at 37° C.

For digest mapping, gliadin digestion was performed as described above, except that the substrate to enzyme ratio was approximately 1000:1. Gliadin was digested at 37° C. for 2 hr with nepenthesin extract, purified nepenthesin extract, or recombinant nepenthesin I.

The P1 cleavage preference of recombinant nepenthesin I is very similar to that of the concentrated fluid extract, as well as the purified fraction of the extract (FIG. 9A). Surprisingly, the extract showed a higher preference for glutamine than either the purified extract or recombinant nepenthesin I.

The P1' cleavage preference of recombinant nepenthesin I is very similar to that of the concentrated fluid extract, as well as the purified fraction of the extract (FIG. 9B). Surprisingly, the extract showed a higher preference for proline than either the purified extract or recombinant nepenthesin I.

The extract contains nepenthesin I, nepenthesin II, and neprosin, but the purification strategy recovers more nepenthesin I than the other two enzymes. Without wishing to be bound by theory, it is believed that the heightened cleavage at the P1 glutamine position and the P1' proline position by the extract are due to neprosin, nepenthesin II, and/or synergy between two or more of the enzymes.

Example 8. Preparation of Neprosin Extract

Neprosin was extracted from *Nepenthes* sp. digesting fluid. The fluid was collected from the plant pitcher 5 days after feeding with frozen fruit flies. The collected liquid was filtered to removed dead insects and repeatedly washed with 20 mM ammonium acetate pH 5.0 by multiple concentration/filtration cycles through a 10 kDa molecular weight cut-off membrane.

Figure 10:
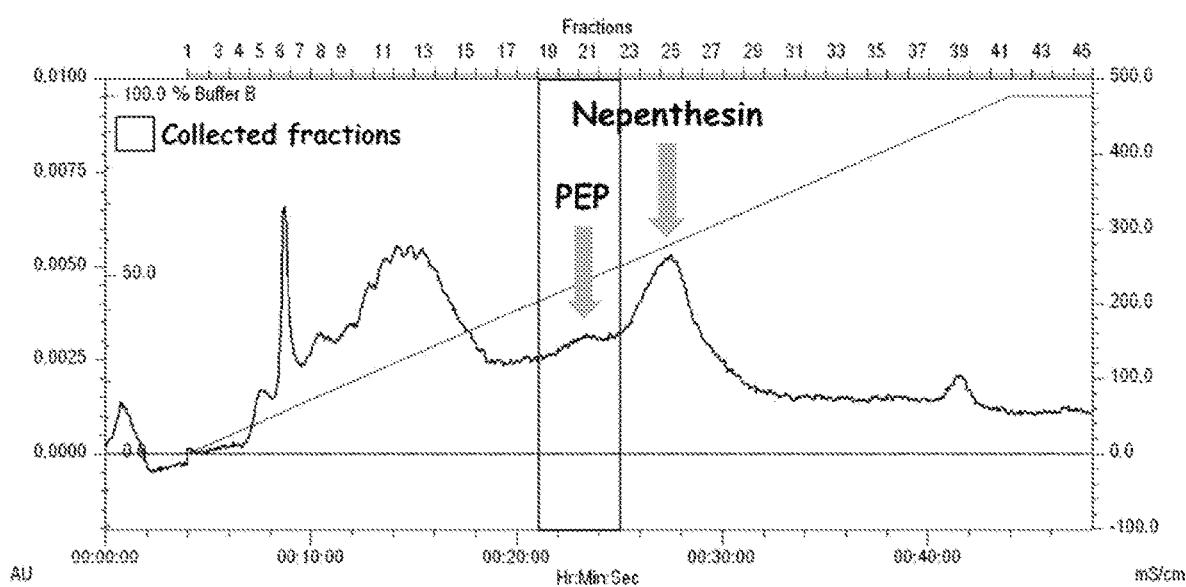
FIG. 10 shows the ion exchange purification profile for Nepenthes fluid. Peaks corresponding to neprosin and nepenthesin are indicated by arrows. The boxed region indicates the collected fractions.

Neprosin was partially purified away from nepenthesin on a mono P 5/50 GL column. 5 mL of 1.5× concentrated fluid was injected onto the mono P column equilibrated at low ionic strength (20 mM Ammonium acetate pH 6). The proteins were eluted with a 40 min NaCl gradient (0 to 1M) at 0.5 ml/min. The fractions were collected every 0.5 ml. Neprosin activity was tested in each fraction by digesting an intrinsically-disordered proline-rich protein, APLF. The peptides generated were separated on a C8 column and analyzed by LC-MS/MS on a tripleToF 5600 (AB Sciex). Fractions 19-22 were enriched for neprosin (FIG. 10) and are termed the crude neprosin extract; neprosin is distinct from nepenthesin, which was enriched in later fractions.

Example 9. Efficacy of *Nepenthes* Enzymes in Inhibiting Inflammation in the Intestines of Gluten-Intolerant Mice Objective:
To test the efficacy of in vitro digestion of gliadin using *Nepenthes* extract or recombinant nepenthesin II in preventing in vivo gliadin-induced damage using gliadin-sensitized NOD-DQ8 mice.

Experimental Design:
NOD DQ8 mice were sensitized with cholera toxin (CT) and gliadin to break oral tolerance to gliadin. Negative controls were treated with CT and gliadin, but left free of subsequent oral gliadin challenges. Gliadin challenges were performed with a porcine protease (pepsin) digest of gliadin containing a variety of toxic and immunogenic derived peptides. Treatment groups were challenged with gliadin predigested with *Nepenthes* extract or recombinant nepenthesin II (for 90 minutes at 37 degrees Celsius). It is hypothesized that *Nepenthes* extract- or recombinant nepenthesin II-gliadin digests will be less immunogenic in vivo than pepsin-gliadin digests.

Groups:
Positive Control (n=8):
Sensitized and gliadin challenged. Mice were sensitized with cholera toxin (CT) and pepsin gliadin (P-G) (1× per week for 3 weeks). During the experimental period, mice were gavaged with P-gliadin (3× per week for 3 weeks).

Negative Control (n=8):
Sensitized (then gliadin free). Mice were sensitized with cholera toxin (CT) and pepsin gliadin (P-G) (1× per week for 3 weeks). During the experimental period, mice were gavaged with vehicle (3× per week for 3 weeks).

Treatment 1 (n=8):
*Nepenthes* extract. Mice were sensitized with cholera toxin (CT) and pepsin gliadin (P-G) (1× per week for 3 weeks). During the experimental period, mice were gavaged with *Nepenthes* extract-digested gliadin (3× per week for 3 weeks).

Treatment 2 (n=8):
Mice were sensitized with cholera toxin (CT) and pepsin gliadin (P-G) (1× per week for 3 weeks). During the experimental period, mice were gavaged with nepenthesin II-digested gliadin (3× per week for 3 weeks)

Results:
All 4 groups of mice were sensitized with pepsin-gliadin digest plus cholera toxin. Negative controls were left free of gliadin challenge after sensitization. Positive controls and the treatment groups were orally challenged with gliadin after sensitization. The difference in the treated groups was that the gliadin challenge was pre-digested with *Nepenthes* extract or nepenthesin II. In this way, the "negative controls" were not totally naïve of gliadin (since they were exposed during sensitization phase), and thus mimicked the clinical situation of a celiac patient going into remission while adhering to a gluten-free diet.

Figure 11:
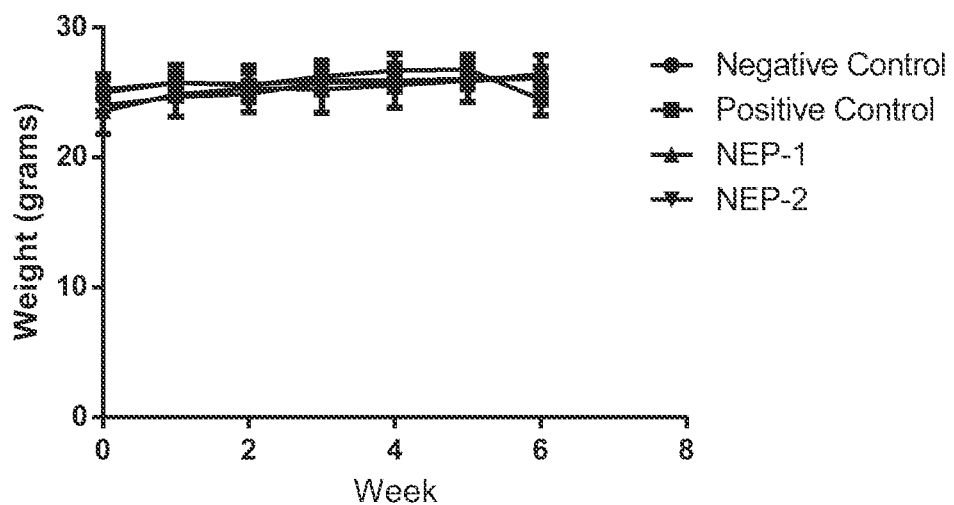
FIG. 11 shows body weights of mice during the course of treatment. Negative control (●) animals were not challenged with gliadin. Positive control (■) animals were challenged with gliadin digested by pepsin. Treatment 1 (▲) animals were challenged with gliadin digested with Nepenthes extract. Treatment 2 (▼) animals were challenged with gliadin digested with recombinant nepenthesin II.

Clinical/Toxic Effects:
Overall appearance of the mice (movement, eye opening, grooming) was evaluated. No ill effects were observed in any of the treatment or control groups. Body weights were recorded throughout the experiments and no weight loss was observed in any of the groups (FIG. 11).

Figure 12:
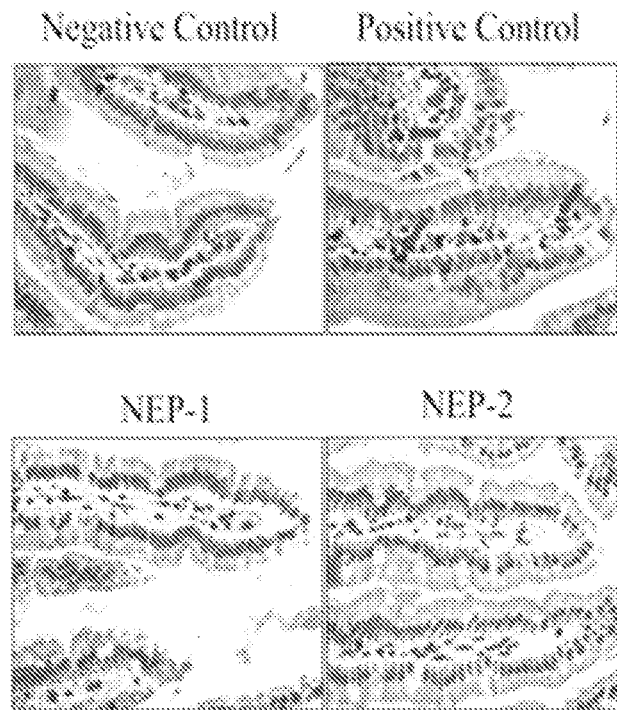
FIG. 12 is a photograph of the immunohistochemistry for CD3-positive IELs in the intestine of treated mice.
Figure 13:
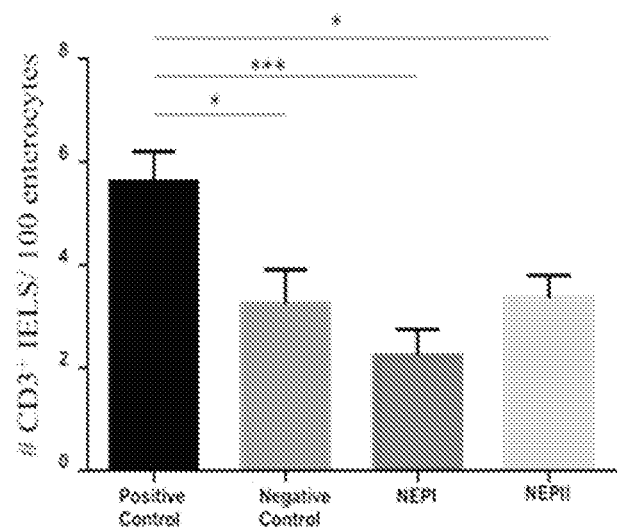
FIG. 13 shows the average number of CD3-positive intraepithelial lymphocytes (IELs) per 100 enterocytes in the intestine for each treatment group. $*p<0.05$; $***p<0.001$

Innate Immune Changes to Gliadin Challenge:
Immunohistochemistry for CD3+ intraepithelial lymphocytes was performed on the intestines of mice from each treatment group (FIG. 12). This is a quick and early innate immune marker of intestinal gliadin exposure in the model. Gliadin exposure resulted in increased IEL counts compared to negative control mice and to mice exposed to gliadin that was pre-digested with *Nepenthes* extract or nepenthesin II (FIG. 13). No differences in IEL counts were observed between *Nepenthes* extract and nepenthesin II treated groups.

Figure 14:
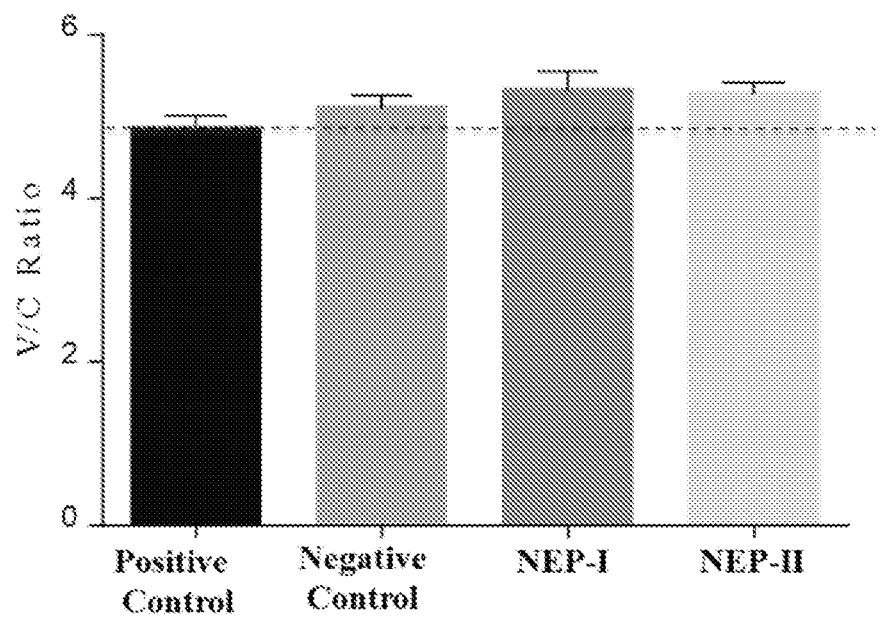
FIG. 14 shows the average villous to crypt ratios for each treatment group.

Villus to Crypt Ratios:
Non-significant trends were observed for lower villus/crypt (V/C) ratios in the positive control group (FIG. 14). *Nepenthes* extract and nepenthesin II treated groups had a trend for higher ratios compared to the positive and negative controls.

Interpretation/Discussion:
A three-week challenge with gliadin pre-digested with *Nepenthes* extract or nepenthesin II was safe and did not induce short-term decreases in body weight or any clinical adverse event in mice.

Oral gliadin challenges led to significant increases in small intestinal IEL counts in previously sensitized in mice.

The IEL increase was not observed in mice that were challenged with gliadin that had been pre-digested with *Nepenthes* extract or nepenthesin II. This suggests a lower luminal antigenicity of the gliadin treated with *Nepenthes* extract or nepenthesin II.

Reduction in V/C ratios was very mild in the positive control group. However, there were non-significant trends for higher V/C ratios in mice that were challenged with gliadin that was predigested with *Nepenthes* extract or nepenthesin II. Reduction in V/C ratios in this animal model is moderate and varies with the duration and dose of the gliadin challenge. The differences are more marked between positive and negative controls when the latter are completely naïve of gliadin/gluten (non-sensitized). It is believed that differences in V/C ratios using predigested *Nepenthes* extract or nepenthesin II in a more chronic setting and/or compared to mice that are completely naïve of gliadin (non-sensitized) would be more pronounced.

Overall Conclusion:

The results show an effect of pre-digestion of gliadin with *Nepenthes* extract or nepenthesin II to reduce the antigenicity of the gliadin peptides in the small intestinal tract of sensitized NOD/DQ8 mice.

Example 10. Gliadin Digestion by Neprosin

Figure 15B:
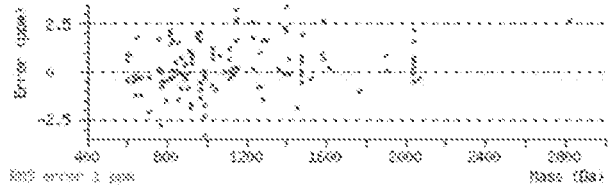
FIG. 15B shows the digestion profile of gliadin after digestion with neprosin. Periods indicate cleavage sites (SEQ ID NOS 23-150, respectively, in order of appearance).

Crude neprosin extract was incubated with gliadin at pH 2.5 and the resulting peptide fragments analyzed by MS. The results are shown in FIGS. 15A and 15B (a dot [.] indicates a cleavage site). The protein sequence coverage by the extract was 61%. Approximately 57% of the potential proline (P) cleavage sites (C-terminal) in gliadin were processed by the crude neprosin extract. Without being bound by theory, it is believed that at least a portion of the glutamine cleavage sites were due to a small amount of contamination of the extract with nepenthesin proteins.

What is claimed is:

1. A pharmaceutical composition comprising recombinant neprosin and a pharmaceutically acceptable buffering agent, wherein
the recombinant neprosin is a protein having at least 90% sequence identity to amino acids 25 to 380 of the amino acid sequence of SEQ ID NO: 1 and having prolyl endopeptidase activity, wherein the recombinant neprosin has a different glycosylation pattern than natural neprosin.

2. The pharmaceutical composition of claim 1, wherein the amino acid sequence of the neprosin comprises an amino acid sequence having at least 90% sequence identity to the amino acid sequence of SEQ ID NO: 1 and having prolyl endopeptidase activity.

3. The pharmaceutical composition of claim 2, further comprising at least one additional Nepenthes enzyme or variant thereof, wherein the at least one additional Nepenthes enzyme comprises the amino acid sequence of SEQ ID NO: 5, SEQ ID NO: 6, SEQ ID NO: 7, SEQ ID NO: 8, SEQ ID NO: 9, SEQ ID NO: 21, or SEQ ID NO: 22 or a variant thereof comprising at least 85% sequence identity to the amino acid sequence of SEQ ID NO: 5, SEQ ID NO: 6, SEQ ID NO: 7, SEQ ID NO: 8, SEQ ID NO: 9, SEQ ID NO: 21, or SEQ ID NO: 22 and having protease activity.

4. The pharmaceutical composition of claim 3, wherein the at least one additional Nepenthes enzyme or variant thereof is nepenthesin I, nepenthesin II, and/or a variant thereof.

5. The pharmaceutical composition of claim 1, wherein said composition is a sustained release formulation.

6. The pharmaceutical composition of claim 3, wherein the neprosin and/or Nepenthes enzyme(s) comprises a propeptide.

7. A solid pharmaceutical formulation comprising the composition of claim 1, wherein the neprosin is present in multiple layers such that the neprosin is released continuously while the formulation is present in the stomach.

8. The pharmaceutical composition of claim 1, wherein the pharmaceutical composition is formulated for oral administration.

9. The pharmaceutical composition of claim 1, wherein the neprosin comprises the amino acid sequence of SEQ ID NO: 1.

10. The pharmaceutical composition of claim 3, wherein the at least one additional Nepenthes enzyme or variant thereof is nepenthesin II.

11. The pharmaceutical composition of claim 3, wherein the at least one additional Nepenthes enzyme or variant thereof is nepenthesin I.

12. The pharmaceutical composition of claim 3, wherein the ratio of neprosin to the at least one additional Nepenthes enzyme or variant thereof is between 100:1 and 1:100.

13. The pharmaceutical composition of claim 1, wherein the pharmaceutical composition is in liquid form.

14. The pharmaceutical composition of claim 1, wherein the buffering agent maintains the pharmaceutical composition at a pH of 6.5 or above when the pharmaceutical composition is in liquid form prior to administration to a subject.

15. The pharmaceutical composition of claim 14, wherein the buffering agent maintains the composition at a pH of about 7.0 or above.

\* \* \* \* \*